United States Patent
Koh et al.

(10) Patent No.: US 6,511,978 B1
(45) Date of Patent: Jan. 28, 2003

(54) PYRROLE DERIVATIVES USEFUL FOR FARNESYL TRANSFERASE INHIBITORS AND THEIR PREPARATIONS

(75) Inventors: Jong-Sung Koh, Taejon (KR); Hyun-Il Lee, Taejon (KR); You-Seung Shin, Taejon (KR); Hak-Joong Kim, Seoul (KR); Jin-Ho Lee, Taejon (KR); Jong-Hyun Kim, Taejon (KR); Hyun-Ho Chung, Taejon (KR); Shin-Wu Jeong, Taejon (KR); Tae-Saeng Choi, Taejon (KR); Jung-Kwon Yoo, Taejon (KR); Chung-Mi Kim, Taejon (KR); Kwi-Hwa Kim, Taejon (KR); Sun-Hwa Lee, Taejon (KR); Sang-Kyun Lee, Taejon (KR)

(73) Assignee: LG Life Sciences, Ltd., Seoul (KR)

( * ) Notice: Subject to any disclaimer, the term of this patent is extended or adjusted under 35 U.S.C. 154(b) by 0 days.

(21) Appl. No.: 09/958,478

(22) PCT Filed: Apr. 11, 2000

(86) PCT No.: PCT/KR00/00334

§ 371 (c)(1),
(2), (4) Date: Oct. 11, 2001

(87) PCT Pub. No.: WO00/64891

PCT Pub. Date: Nov. 2, 2000

(30) Foreign Application Priority Data

Apr. 13, 1999 (KR) ............................. 99/12994
Aug. 10, 1999 (KR) ............................. 99/32814
Aug. 11, 1999 (KR) ............................. 99/32972

(51) Int. Cl.[7] ................... C07D 403/06; A61K 31/535
(52) U.S. Cl. ........................... 514/235.8; 514/254.05; 544/139; 544/141; 544/370; 544/372; 548/314.7
(58) Field of Search ................. 548/314.7; 544/139, 544/141, 370, 372; 514/254.05, 235.8

(56) References Cited

U.S. PATENT DOCUMENTS 6,268,363 B1 * 7/2001 Lee et al. ................ 514/235.8

* cited by examiner

Primary Examiner—Joseph K. McKane
Assistant Examiner—Kamal Saeed
(74) Attorney, Agent, or Firm—Peter F. Corless; Christine C. O'Day; Edwards & Angell, LLP

(57) ABSTRACT

The present invention relates to a novel pyrrole derivative which shows an inhibitory activity against farnesyl transferase or pharmaceutically acceptable salts or isomers thereof; to a process for preparation of said compound; and to a pharmaceutical composition such as anti-cancer composition, etc. comprising said compound as an active ingredient together with pharmaceutically acceptable carrier.

7 Claims, No Drawings

PYRROLE DERIVATIVES USEFUL FOR FARNESYL TRANSFERASE INHIBITORS AND THEIR PREPARATIONS

This is a 371 of PCT/KR00/00334 filed on Apr. 11, 2000

TECHNICAL FIELD

The present invention relates to a novel compound represented by the following formula (1) which has a pyrrole structure and shows an inhibitory activity against farnesyl transferase:

(1)

in which

A represents hydrogen, lower alkyl, or a structure selected from the following group:

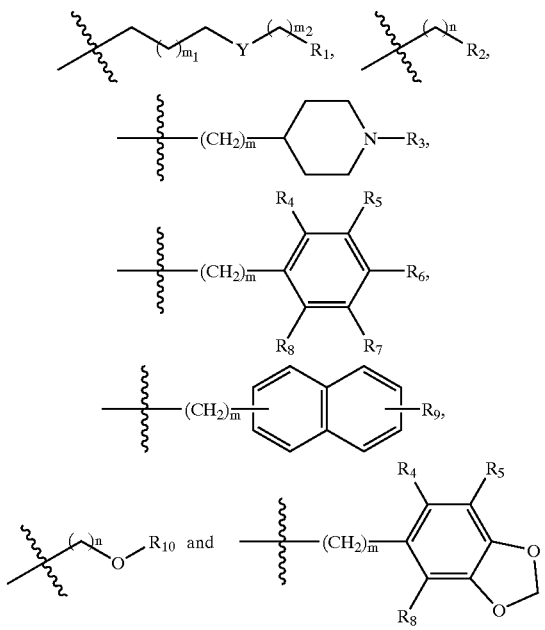

wherein $m_1$, $m_2$, m and n independently of one another denote an integer of 0 to 5, Y represents O, S, S=O or $SO_2$, $R_1$ represents hydrogen, or represents optionally saturated 3- to 6-membered heterocycle or bicyclo 9- to 10-membered aromatic heterocycle, each of which has one or more hetero atoms selected from a group consisting of nitrogen, sulfur and oxygen, or represents a structure selected from the following group:

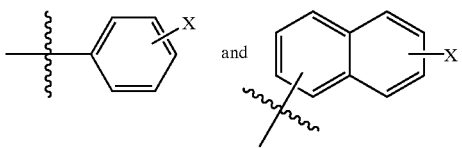

wherein,

X represents hydrogen, halogen, lower alkyl, lower alkoxy, nitro, cyano, hydroxy or phenoxy, $R_2$ represents optionally saturated 3- to 9-membered heterocycle or bicyclo 9- to 10-membered aromatic heterocycle, each of which has one or more hetero atoms selected from a group consisting of nitrogen, sulfur and oxygen, or represents a structure selected from the following group:

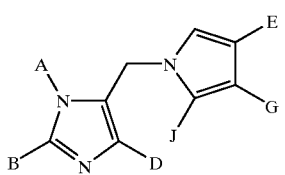

wherein, p denotes an integer of 1 to 3, Y is defined as previously described, $R_{11}$ and $R_{12}$ independently of one another represent lower alkyl optionally substituted by phenyl or naphthyl, or represent $C_3$–$C_7$-cycloalkyl, phenyl or naphthyl, $R_3$ represents lower alkyl, lower alkylcarbonyl, lower alkoxycarbonyl or lower alkylsulfonyl, each of which is optionally substituted by phenyl or naphthyl, or represents sulfonyl substituted by phenyl or naphthyl, $R_4$ and $R_8$ independently of one another represent hydrogen, lower alkyl, lower alkoxy or halogen, $R_5$ and $R_7$ independently of one another represent hydrogen, lower alkyl, lower alkoxy, halogen or hydroxy, $R_6$ represents hydrogen, lower alkyl, lower alkoxy, hydroxy, di(lower alkyl)amine, $C_3$–$C_6$-cycloalkyl, $C_3$–$C_6$-cycloalkyl-lower alkyl, halogen, phenyl or phenoxy, $R_9$ represents hydrogen or lower alkyl, $R_{10}$ represents aralkyl optionally substituted by lower alkyl or halogen, B represents hydrogen, lower alkyl, lower alkylthio or amino, D represents hydrogen, lower alkyl, halogen, lower alkylthio, nitro or amino, E represents phenyl, or naphthyl optionally substituted by halogen, G represents nitro or amino, or represents a structure of

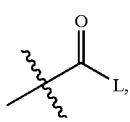

wherein

L represents a structure selected from the following group:

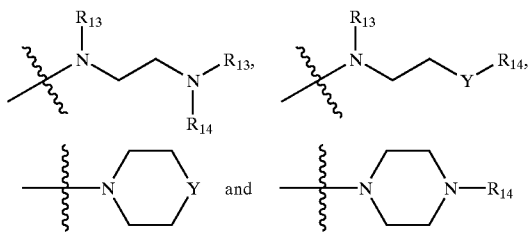

wherein
$R_{13}$ and $R_{14}$ independently of one another represent hydrogen, hydroxy, lower alkyl or lower alkoxy, Y is defined as previously described, J represents hydrogen, lower alkyl, lower alkylthio or phenyl, provided that A does not represent hydrogen, lower alkyl or any one structure selected from the following group:

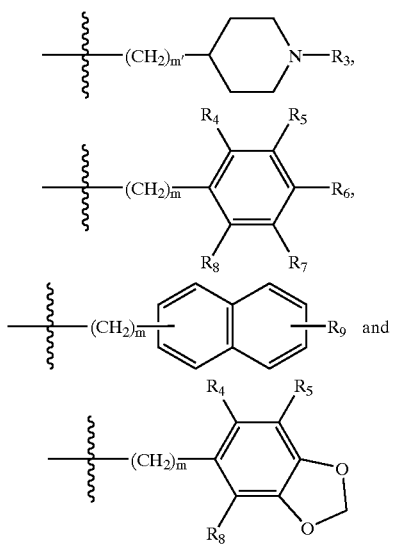

wherein m and $R_3$ to $R_9$ are defined as previously described, m' denotes an integer of 1 to 5, when B, J and D represent hydrogen at the same time and G does not represent nitro or amino, or pharmaceutically acceptable salts or isomers thereof.

The present invention also includes processes for the preparation of said compound of formula (1), and compositions useful for treating or preventing cancer, restenosis (Erick E. Brooks, et. al. *The Journal of Biological Chemistry*, 272 (14), 29207–29211, 1997), atherosclerosis (Russell Ross, *Nature*, 362, 801–809, 1993; Joseph L. Goldstein, et. al., *Nature*, 343, 425–430, 1990) or infections from viruses (James C. Otto, et. al., *The Journal of Biological Chemistry*, 272(9), 4569–4572, 1996), which comprise as an active ingredient the compound of formula (1) together with the pharmaceutically acceptable carrier. Therefore, those processes and compositions are subject matters of the present invention.

BACKGROUND ART

Ras is a 21 kDa protein which plays an important role in the events associated with cell growth and differentiation. It combines with guanine nucleotide, whereby catalyzes the hydrolysis reaction from guanosine triphosphate (GTP) to guanosine diphosphate (GDP). Further, this protein has been reported to act as a molecular switch regulating the specific GTPase cycle inside the cell (see: Bourne, H. R., Sanders, D. A., McCormick, F. *Nature* 1991, 349, 117).

The mammalian Ras protein is coded by three (3) types of ras gene and classified into four (4) types; i.e., K-Ras-4B consisting of 188 amino acid residues and H-Ras, K-Ras-4A and N-Ras consisting of 189 residues, respectively. Amino acids 12, 13 and 61 of Ras, positioned in the neighborhood of phosphoryl group of GTP, regulate the activity of GTPase by having a large effect on spacial position of a water molecule which participates in the GTP hydrolysis. In human cancers, mutations are observed at the above amino acid positions. Since Ras mutations inhibit its ability to regulate GTPase activity, GTP-binding state of Ras is maintained, and thus, growth signal is transduced abnormally to cause cancer. In particular, ras oncogene is related to pancreatic cancer, urinary bladder carcinoma, lung cancer and skin cancer, etc. (see: Bos, J. L., *Cancer Res.*, 1989, 49, 4682).

To be in its biologically activated state, Ras must be attached to cell membrane and for this reason, modification or carboxyl terminus of the protein is required after the transportation of protein. The modification process comprises the steps of farnesylation of Ras by Ras farnesyl transferase, displacement of AAX peptide consisting of 3 amino acids at the C-terminus of Ras by peptide cleavage enzyme, methyl esterification of Ras by methyl transferase and palmitoylation of Ras by palmitoyl transferase. Among the above-described steps of modifying carboxyl terminus of Ras, the farnesylation step is proceeded by farnesyl transferase (FTase), and substrate for the transferase is $CA_1A_2X$ peptide consisting of 4 amino acids at the C-terminus or Ras, where $A_1$ and $A_2$ are aliphatic amino acids having no charge and X is methionine, alanine or serine, etc. The farnesylation occurs at cysteine, and sulfur ether bond is formed. While, in H-Ras and N-Ras, palmitoylation occurs at another cysteine proximate to the C-terminus. The above-described farnesylation results in the enhancement of hydrophobicity of Ras, and hence its affinity for cell membrane increases. The farnesylated Ras is subjected to the cleavage of AAX peptide from the C-terminus thereof by the cleavage enzyme and methyl-esterified so that it can attach to the lipid layer of cell membrane or other receptors more easily. K-Ras-4B, differently from H-Ras or N-Ras, has a multiple lysine-arranged-region named polybasic domain, instead of having cysteine required for palmitoylation. It has been known that the polybasic domain facilitates Ras to bind to anionic lipid of cell membrane. All the above-described steps attribute to enhancing the attachment of Ras to cell membrane under the optimal condition, but only the farnesylation step is essentially required to express the biological activity of Ras. That is, if farnesylation step is inhibited, the resulting mutant Ras is prevented from being attached to cell membrane. Hence, inhibitors of farnesylation have been subjects of many studies (see: J. E. Buses et al., *Chemistry & Biology*, 1995, 2, 787).

As results of the studies, when farnesyl transferase is inhibited in a cell transformed by Ras, it is observed that the conditions of abnormal cells caused by mutant Ras are improved while growth of cells is inhibited.

Several inhibitors of farnesyl transferase are found to selectively inhibit intracellular prenyl group reaction of oncogenic Ras (see: Kohl, N. E. et al., *Proc. Natl. Acad. Sci. USA*, 91, 9141(1994); Kohl, N. E. et al., *Nature Medicine*, 1, 792(1995)). The inhibitors of farnesyl transferase being studied recently include peptide variants having cysteine thiol group imitating CAAX and improved inhibitors (see: U.S. Pat. No. 5,141,851; Kohl, N. E. et al., *Science*, 260, 1934(1993); Graham et al., PCT/US95/12224), peptides modified by phenyl group (see: Sebti, S. M., *J. Biol. Chem.*, 270, 26802, 1995), variants using benzodiazepin, a frame structure of positive psycopharmaceuticals, as turn-imitating structure of peptide (see: James, G. L. et al., *Science*, 260, 1937, 1993) and inhibitors having tricyclic organic compound frame deviating its peptide structure (see: Bishop, W. R. et al., *J. Biol. Chem.*, 270, 30611, 1995). In addition, a new type of inhibitor wherein (+) charge in the transition state is linked with the prenyl group has been reported. It was designed upon the notice that since the reaction mechanism in the transfer of prenyl group by farnesyl transferase is a type of electrophilic displacement, this reaction requires (+) charge in transition state (see: Poulter, C. D. et al., *J. Am. Chem. Soc.*, 118, 8761, 1996).

However, the activation of K-Ras has been found in most human cancers, and most of the prenyl transferase inhibitors developed hitherto are found to activate K-Ras. The existing inhibitors inhibit the growth of cells transformed with K-Ras less effectively than that with H-Ras or N-Ras. Therefore, new inhibitor having the capability of effectively inhibiting K-Ras activity is required.

Thus, the present inventors established a new evaluation system by which the inhibitory activity against enzyme action for K-Ras substrate and inhibitory activity against intracellular K-Ras prenylation can be determined. Then, we synthesized novel compounds inhibiting the farnesylation of H-Ras, N-Ras as well as K-Ras and screened them using said new system. As a result, we have found that the compound of formula (1) as defined above can be used as an effective anti-cancer agent, etc., and then completed the present invention. Particularly, the compound according to the present invention has a characteristic structure different from those of the existing inhibitors against farnesyl transferase and does not include any thiol group.

Therefore, the object of the present invention is to provide the compound of formula (1) having a superior anti-cancer effect and process for preparation thereof.

It is another object of the present invention to provide compositions for treating cancer, restenosis, atherosclerosis and viral infections, respectively, each of which comprises as an active ingredient the compound of formula (1) together with the pharmaceutically acceptable carrier.

DISCLOSURE OF INVENTION

The present invention relates to a compound of the following formula (1) which has a pyrrole structure and shows an inhibitory activity against farnesyl transferase:

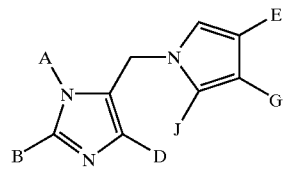

in which

A represents hydrogen, lower alkyl, or a structure selected from the following group:

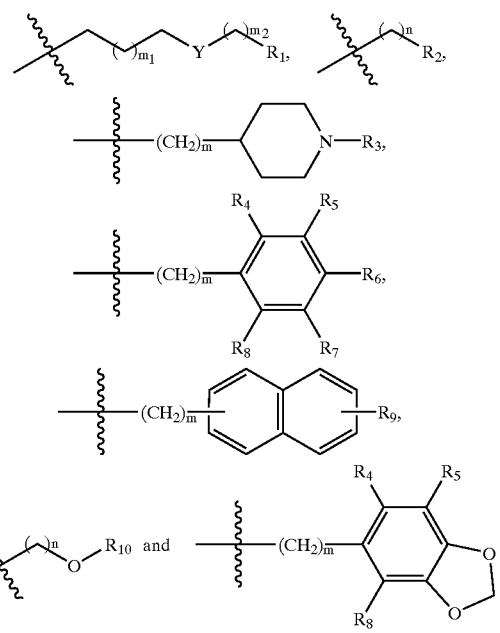

wherein
- $m_1$, $m_2$, m and n independently of one another denote an integer of 0 to 5,
- Y represents O, S, S=O or $SO_2$,
- $R_1$ represents hydrogen, or represents optionally saturated 3- to 6-membered heterocycle or bicyclo 9- to 10-membered aromatic heterocycle, each of which has one or more hetero atoms selected from a group consisting of nitrogen, sulfur and oxygen, or represents a structure selected from the following group:

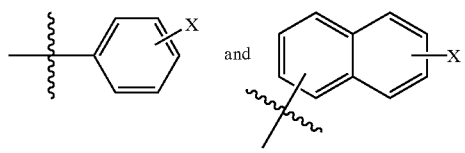

wherein,
- X represents hydrogen, halogen, lower alkyl, lower alkoxy, nitro, cyano, hydroxy or phenoxy,
- $R_2$ represents optionally saturated 3- to 9-membered heterocycle or bicyclo 9- to 10-membered aromatic heterocycle, each of which has one or more hetero atoms selected from a group consisting of nitrogen, sulfur and oxygen, or represents a structure selected from the following group:

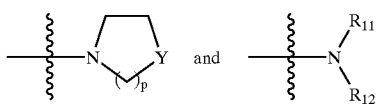

wherein,
- p denotes an integer of 1 to 3, Y is defined as previously described, $R_{11}$ and $R_{12}$ independently of one another represent lower alkyl optionally substituted by phenyl or naphthyl, or represent $C_3$–$C_7$-cycloalkyl, phenyl or naphthyl,
- $R_3$ represents lower alkyl, lower alkylcarbonyl, lower alkoxycarbonyl or lower alkylsulfonyl, each of which is optionally substituted by phenyl or naphthyl, or represents sulfonyl substituted by phenyl or naphthyl, $R_4$ and $R_8$ independently of one another represent hydrogen, lower alkyl, lower alkoxy or halogen, $R_5$ and $R_7$ independently of one another represent hydrogen, lower alkyl, lower alkoxy, halogen or hydroxy, $R_6$ represents hydrogen, lower alkyl, lower alkoxy, hydroxy, di(lower alkyl)amine, $C_3$–$C_6$-cycloalkyl, $C_3$–$C_6$-cycloalkyl-lower alkyl, halogen, phenyl or phenoxy, $R_9$ represents hydrogen or lower alkyl, $R_{10}$ represents aralkyl optionally substituted by lower alkyl or halogen, B represents hydrogen, lower alkyl, lower alkylthio or amino, D represents hydrogen, lower alkyl, halogen, lower alkylthio, nitro or amino, E represents phenyl, or naphthyl optionally substituted by halogen, G represents nitro or amino, or represents a structure of

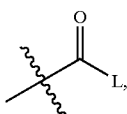

wherein

L represents a structure selected from the following group:

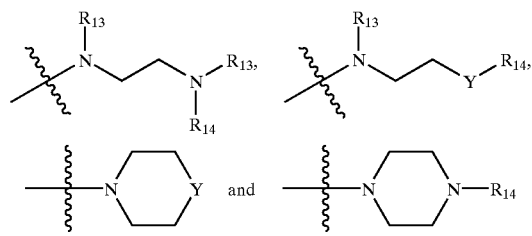

wherein $R_{13}$ and $R_{14}$ independently of one another represent hydrogen, hydroxy, lower alkyl or lower alkoxy, Y is defined as previously described, J represents hydrogen, lower alkyl, lower alkylthio or phenyl, provided that A does not represent hydrogen, lower alkyl or any one structure selected from the following group:

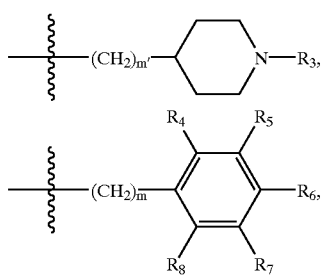

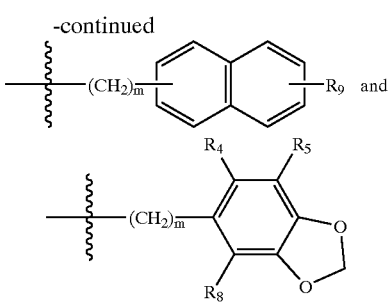

wherein m and $R_3$ to $R_9$ are defined as previously described, m' denotes an integer of 1 to 5, when B, J and D represent hydrogen at the same time and G does not represent nitro or amino, or pharmaceutically acceptable salts or isomers thereof.

Among the compound of formula (1) having a superior inhibitory activity against farnesyl transferase, the preferred compounds include those wherein A represents lower alkyl or a structure selected from the following group:

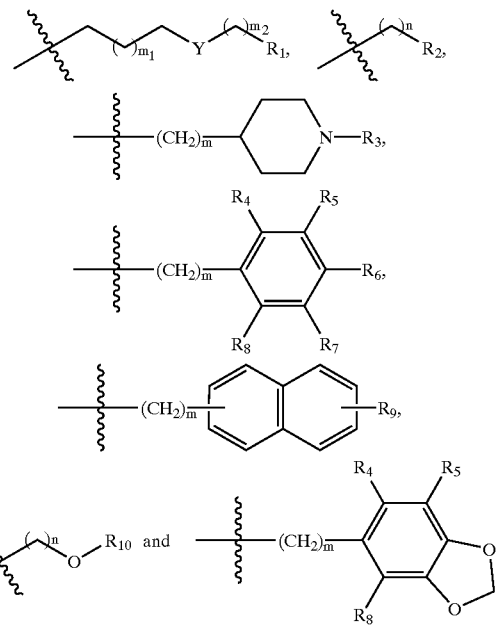

wherein $m_1$, $m_2$, m and n independently of one another denote an integer of 0 to 3, Y represents O or S, $R_1$ represents hydrogen, or represents a structure selected from the following group:

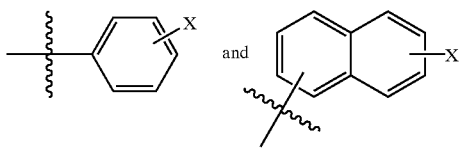

wherein,

X represents hydrogen, halogen, lower alkyl, lower alkoxy, nitro, cyano, hydroxy or phenoxy, $R_2$ represents optionally saturated 3- to 9-membered heterocycle having one or more hetero atoms selected from a group consisting of nitrogen, sulfur and oxygen, or represents a structure of

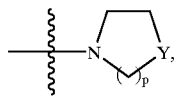

wherein,
p denotes an integer of 1 or 2 and Y represents O,
$R_3$ represents lower alkyl optionally substituted by phenyl or naphthyl,
$R_4$ and $R_8$ independently of one another represent hydrogen or lower alkoxy,
$R_5$ and $R_7$ independently of one another represent hydrogen, lower alkoxy or halogen,
$R_6$ represents hydrogen, lower alkyl, lower alkoxy or halogen,
$R_9$ represents hydrogen,
$R_{10}$ represents aralkyl optionally substituted by lower alkyl or halogen,
B represents hydrogen, lower alkyl, lower alkylthio or amino,
D represents hydrogen, lower alkyl, halogen, nitro or amino,
E represents naphthyl optionally substituted by halogen,
G represents nitro or amino, or represents a structure of

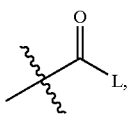

wherein
L represents a structure selected from the following group:

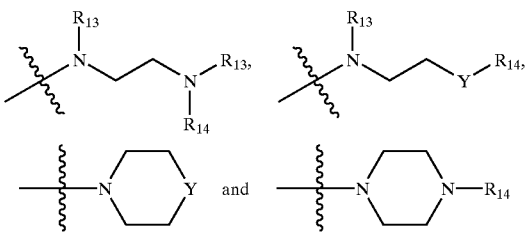

wherein
$R_{13}$ and $R_{14}$ independently of one another represent lower alkyl or lower alkoxy,
Y represents O or S,
J represents hydrogen, lower alkyl or lower alkylthio.

Typical examples of the compound of formula (1) according to the present invention are exemplified in the following (the numbers in the parenthesis represent the number of examples) with the structures of Table 1:

1-[1-(3-benzyloxypropyl)-1H-imidazol-5-yl]methyl-3-[N-(2-methoxy ethyl)-N-methyl]carbamoyl-4-(naphthalen-1-yl)-1H-pyrrole(1);
1-[1-(3-benzyloxypropyl)-1H-imidazol-5-yl]methyl-3-(morpholin-4-yl) carbonyl-4-(naphthalen-1-yl)-1H-pyrrole(2);
1-[1-(3-benzyloxypropyl)-1H-imidazol-5-yl]methyl-3-(4-methylpiperazin-1-yl)carbonyl-4-(naphthalen-1-yl)-1H-pyrrole(3);
3-[N-(2-methoxyethyl)-N-methyl]carbamoyl-4-(naphthalen-1-yl)-1-[1-(3-phenoxypropyl)-1H-imidazol-5-yl]methyl-1H-pyrrole(4);
3-[N-(2-methoxyethyl)-N-methyl]carbamoyl-4-(naphthalen-1-yl)-1-[1-(3-thiophenoxypropyl)-1H-imidazol-5-yl]methyl-1H-pyrrole(5);
3-(morpholin-4-yl)carbonyl-4-(naphthalen-1-yl)-1-[1-(3-phenoxypropyl)-1H-imidazol-5-yl]methyl-1H-pyrrole(6);
3-(4-methylpiperazin-1-yl)carbonyl-4-(naphthalen-1-yl)-1-[1-(3-phenoxypropyl)-1H-imidazol-5-yl]methyl-1H-pyrrole(7);
3-[N-(2-methoxyethyl)-N-methyl]carbamoyl-4-(naphthalen-1-yl)-1-[1-(3-thioethoxypropyl)-1H-imidazol-5-yl]methyl-1H-pyrrole(8);
3-[N-(2-methoxyethyl)-N-methyl]carbamoyl-1-{1-[3-(morpholin-4-yl) propyl]-1H-imidazol-5-yl}methyl-4-(naphthalen-1-yl)-1H-pyrrole(9);
3-[N-(2-methoxyethyl)-N-methyl]carbamoyl-4-(naphthalen-1-yl)-1-{1-[2-(thiophen-2-yl)ethyl]-1H-imidazol-5-yl}methyl-1H-pyrrole(10);
3-(4-methylpiperazin-1-yl)carbonyl-4-(naphthalen-1-yl)-1-{1-[2-(thiophen-2-yl)ethyl]-1H-imidazol-5-yl}methyl-1H-pyrrole(11);
1-[1-(furan-2-yl)methyl-1H-imidazol-5-yl]methyl-3-(4-methylpiperazin-1-yl)carbonyl-4-(naphthalen-1-yl)-1H-pyrrole(12);
1-[1-(1-benzylpiperidin-4-yl)-1H-imidazol-5-yl]methyl-3-[N-(2-methoxyethyl)-N-methyl]carbamoyl-4-(naphthalen-1-yl)-1H-pyrrole(13);
1-[1-(1-benzylpiperidin-4-yl)-1H-imidazol-5-yl]methyl-3-(morpholin-4-yl)carbonyl-4-(naphthalen-1-yl)-1H-pyrrole(14);
1-[2-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(15);
1-[4-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(16);
1-[2-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(17);
1-[1-(3,4-methylenedioxybenzyl)-2-methylthio-1H-imidazol-5-ylmethyl]-3-(4-methylpiperazin-1-yl)carbonyl-4-(naphthalen-1-yl)-1H-pyrrole(18);
1-[1-(3,4-methylenedioxybenzyl)-1H-imidazol-5-ylmethyl]-3-(4-methylpiperazin-1-yl)carbonyl-2-methylthio-4-(naphthalen-1-yl)-1H-pyrrole(19);
1-[4-iodo-1-(3,4-methylenedioxybenzyl)-1H-imidazol-5-ylmethyl]-3-(4-methylpiperazin-1-yl)carbonyl-4-(naphthalen-1-yl)-1H-pyrrole(20);
1-[1-(3,4-methylenedioxybenzyl)-4-nitro-1H-imidazol-5-ylmethyl]-3-(4-methylpiperazin-1-yl)carbonyl-4-(naphthalen-1-yl)-1H-pyrrole(21);
1-[4-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(22);
3-(4-methoxypiperazin-1-yl)carbonyl-1-[4-methyl-1-(3,4-methylenedioxybenzyl)-1H-imidazol-5-ylmethyl]-4-(naphthalen-1-yl)-1H-pyrrole(23);
2-methyl-1-[2-(3,4-methylenedioxybenzyl)-1H-imidazol-5-ylmethyl]-3-(4-methylpiperazin-1-yl)carbonyl-4-(naphthalen-1-yl)-1H-pyrrole(24);
2-ethylthio-1-[1-(3,4-methylenedioxybenzyl)-1H-imidazol-5-ylmethyl]-3-(4-methylpiperazin-1-yl)carbonyl-4-(naphthalen-1-yl)-1H-pyrrole(25);
1-[1-(2-methoxyphenethyl)-2-methyl-1H-imidazol-5-ylmethyl]-3-(4-methylpiperazin-1-yl)carbonyl-4-(naphthalen-1-yl)-1H-pyrrole(26);

1-[1-(3-ethoxypropyl)-2-methyl-1H-imidazol-5-ylmethyl]-3-(4-methyl piperazin-1-yl)carbonyl-4-(naphthalen-1-yl)-1H-pyrrole(27);

1-[1-(3-ethoxypropyl)-4-methyl-1H-imidazol-5-ylmethyl]-3-(4-methyl piperazin-1-yl)carbonyl-4-(naphthalen-1-yl)-1H-pyrrole(28);

1-[1-(3-benzyloxypropyl)-4-methyl-1H-imidazol-5-ylmethyl]-3-(4-methylpiperazin-1-yl)carbonyl-4-(naphthalen-1-yl)-1H-pyrrole(29);

1-[1-(3-benzyloxypropyl)-4-methyl-1H-imidazol-5-ylmethyl]-3-[N-(2-methoxyethyl)-N-methyl]carbamoyl-4-(naphthalen-1-yl)-1H-pyrrole(30);

1-{1-[3-(2-chlorobenzyloxy)propyl]-4-methyl-1H-imidazol-5-ylmethyl}-3-(4-methylpiperazin-1-yl)carbonyl-4-(naphthalen-1-yl)-1H-pyrrole(31);

1-{1-[3-(2-chlorobenzyloxy)propyl]-4-methyl-1H-imidazol-5-ylmethyl}-3-[N-(2-methoxyethyl)-N-methyl]carbamoyl-4-(naphthalen-1-yl)-1H-pyrrole (32);

1-[1-(3-benzyloxypropyl)-2-methyl-1H-imidazol-5-ylmethyl]-3-(4-methylpiperazin-1-yl)carbonyl-4-(naphthalen-1-yl)-1H-pyrrole(33);

1-[1-(3-benzyloxypropyl)-2-methyl-1H-imidazol-5-ylmethyl]-3-[N-(2-methoxyethyl)-N-methyl]carbamoyl-4-(naphthalen-1-yl)-1H-pyrrole(34);

1-[1-(phenethyl)-2-methyl-1H-imidazol-5-ylmethyl]-3-(4-methylpiperazin-1-yl)carbonyl-4-(naphthalen-1-yl)-1H-pyrrole(35);

1-[1-(3,4-methylenedioxybenzyl)-1H-imidazol-5-ylmethyl]-4-(naphthalen-1-yl)-3-nitro-1H-pyrrole(36);

1-[1-(4-chlorobenzyl)-1H-imidazol-5-ylmethyl]-4-(naphthalen-1-yl)-3-nitro-1H-pyrrole(37);

1-[1-(4-bromobenzyl)-1H-imidazol-5-ylmethyl]-4-(naphthalen-1-yl)-3-nitro-1H-pyrrole(38);

1-[1-(phenethyl)-1H-imidazol-5-ylmethyl]-4-(naphthalen-1-yl)-3-nitro-1H-pyrrole(39);

1-[1-(4-methylphenethyl)-1H-imidazol-5-ylmethyl]-4-(naphthalen-1-yl)-3-nitro-1H-pyrrole(40);

1-[1-(4-chlorophenethyl)-1H-imidazol-5-ylmethyl]-4-(naphthalen-1-yl)-3-nitro-1H-pyrrole(41);

1-[1-(4-fluorophenethyl)-1H-imidazol-5-ylmethyl]-4-(naphthalen-1-yl)-3-nitro-1H-pyrrole(42);

1-[1-(3-bromophenethyl)-1H-imidazol-5-ylmethyl]-4-(naphthalen-1-yl)-3-nitro-1H-pyrrole(43);

1-[1-(4-methoxyphenethyl)-1H-imidazol-5-ylmethyl]-4-(naphthalen-1-yl)-3-nitro-1H-pyrrole(44);

1-[1-(3-methoxyphenethyl)-1H-imidazol-5-ylmethyl]-4-(naphthalen-1-yl)-3-nitro-1H-pyrrole(45);

1-[1-(naphthalen-1-ylethyl)-1H-imidazol-5-ylmethyl]-4-(naphthalen-1-yl)-3-nitro-1H-pyrrole(46);

1-[1-(3-ethoxypropyl)-1H-imidazol-5-ylmethyl]-4-(naphthalen-1-yl)-3-nitro-1H-pyrrole(47);

1-[1-(methyl)-1H-imidazol-5-ylmethyl]-4-(naphthalen-1-yl)-3-nitro-1H-pyrrole(48);

1-[1-(naphthalen-2-ylmethyl)-1H-imidazol-5-ylmethyl]-4-(naphthalen-1-yl)-3-nitro-1H-pyrrole(49);

3-amino-1-[1-(4-chlorobenzyl)-1H-imidazol-5-ylmethyl]-4-(naphthalen-1-yl)-1H-pyrrole(50);

4-(3-bromonaphthalen-1-yl)-1-[4-methyl-1-(3,4-methylenedioxybenzyl)-1H-imidazol-5-ylmethyl]-3-(4-methylpiperazin-1-yl)carbonyl-1H-pyrrole(51);

4-(3-chloronaphthalen-1-yl)-1-[4-methyl-1-(3,4-methylenedioxybenzyl)-1H-imidazol-5-ylmethyl]-3-(4-methylpiperazin-1-yl)carbonyl-1H-pyrrole(52);

4-(3-bromonaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(53);

4-(3-chloronaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(54); and 1-[4-methyl-1-(naphthalen-2-yl)methyl-1H-imidazol-5-ylmethyl]-3-(4-methylpiperazin-1-yl)carbonyl-4-(naphthalen-1-yl)-1H-pyrrole(55).

TABLE 1a

| NO | COMPOUND STRUCTURE |
|----|--------------------|
| 1  | 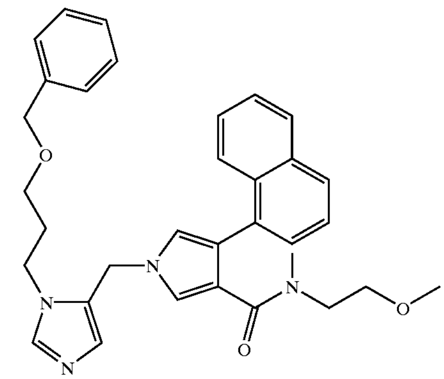                   |
| 2  | 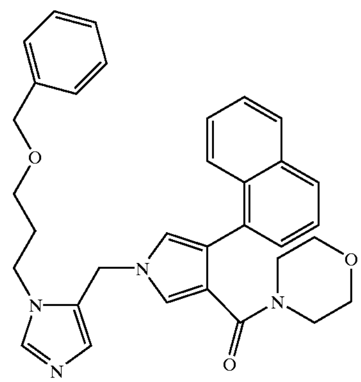                   |
| 3  | 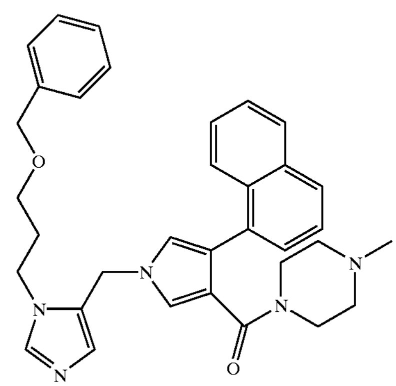                   |
| 4  | 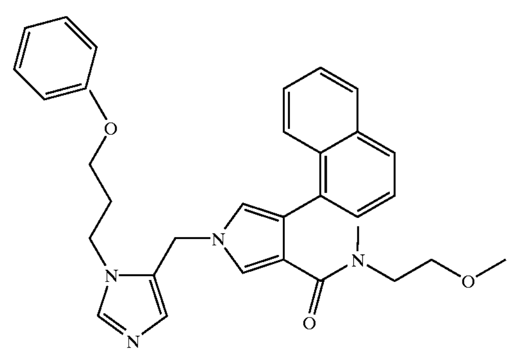                   |

TABLE 1a-continued

| NO | COMPOUND STRUCTURE |
|----|--------------------|
| 5  | 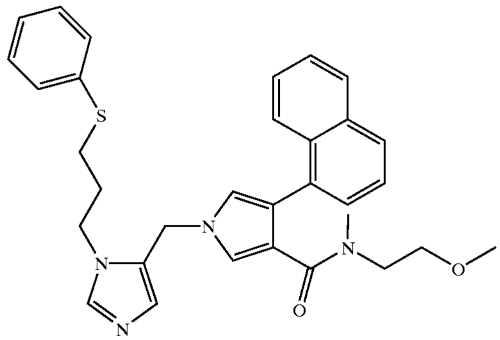                   |
| 6  | 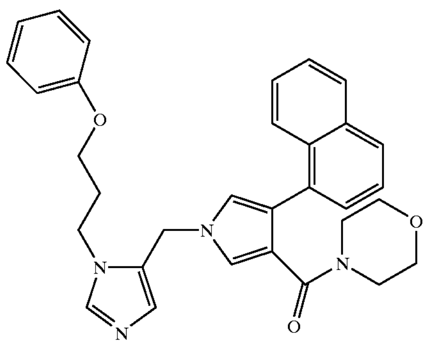                   |
| 7  | 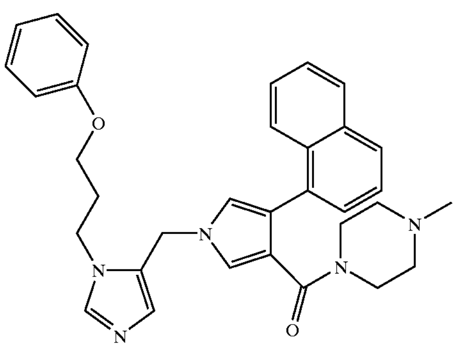                   |
| 8  | 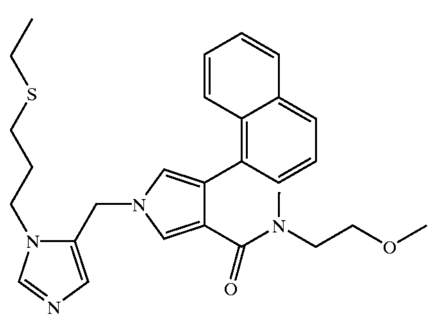                   |

TABLE 1b

| NO | COMPOUND STRUCTURE |
|----|--------------------|
| 9  | 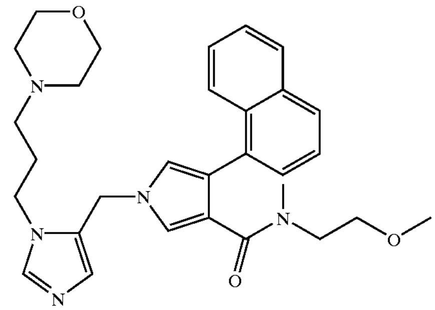                   |
| 10 | 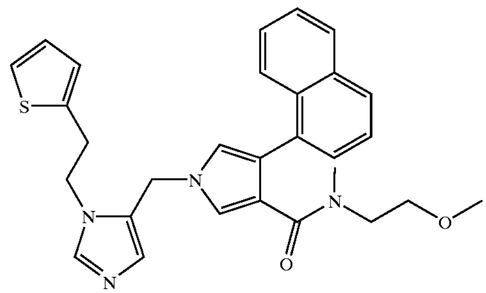                   |
| 11 | 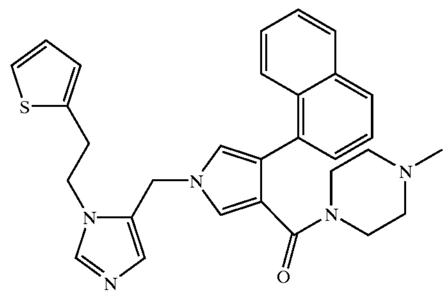                   |
| 12 | 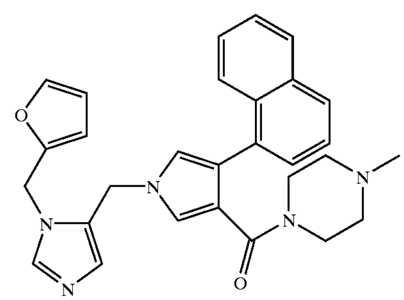                   |
| 13 | 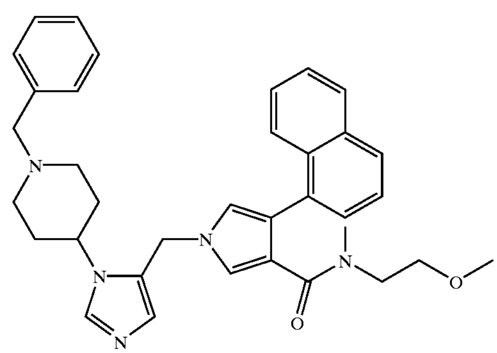                   |

TABLE 1b-continued

| NO | COMPOUND STRUCTURE |
|---|---|
| 14 | 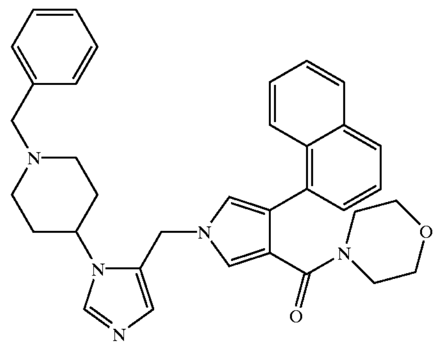 |
| 15 | 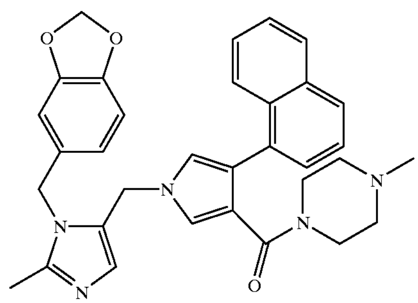 |
| 16 | 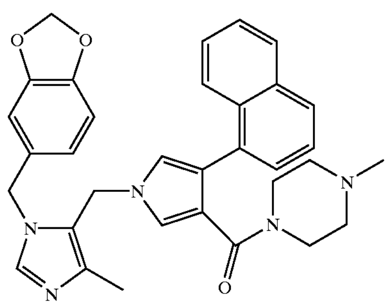 |

TABLE 1c

| NO | COMPOUND STRUCTURE |
|---|---|
| 17 | 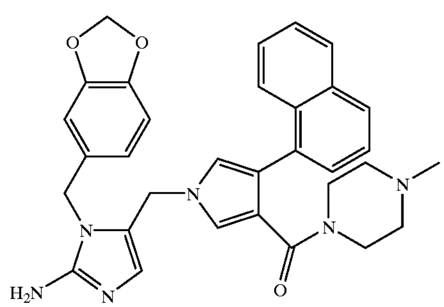 |

TABLE 1c-continued

| NO | COMPOUND STRUCTURE |
|---|---|
| 18 | 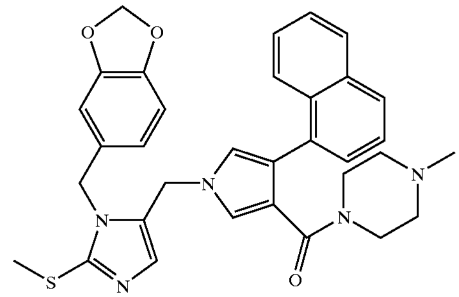 |
| 19 | 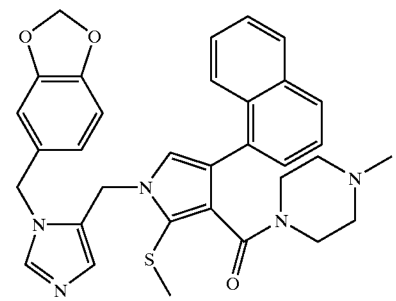 |
| 20 | 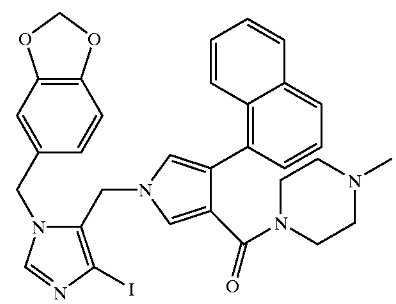 |
| 21 | 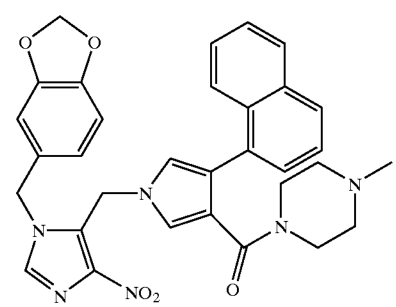 |
| 22 | 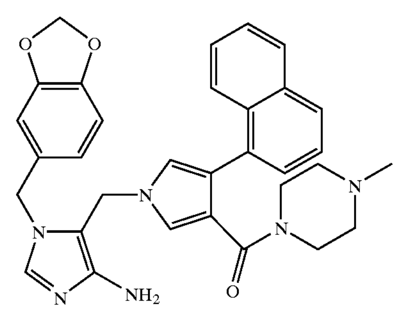 |

TABLE 1c-continued
| NO | COMPOUND STRUCTURE |
|----|--------------------|
| 23 | 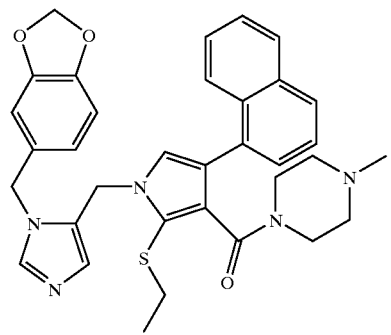 |
| 24 | 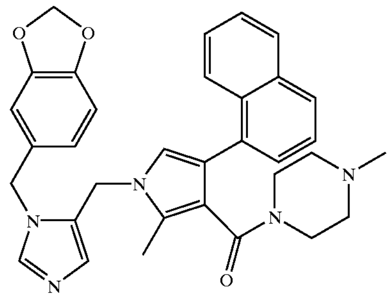 |
TABLE 1d
| NO | COMPOUND STRUCTURE |
|----|--------------------|
| 25 | 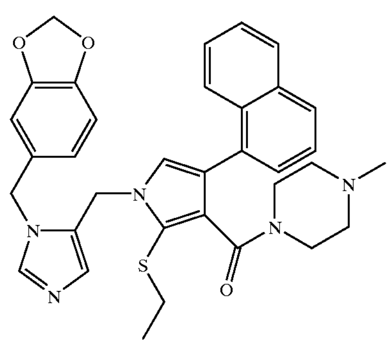 |
| 26 | 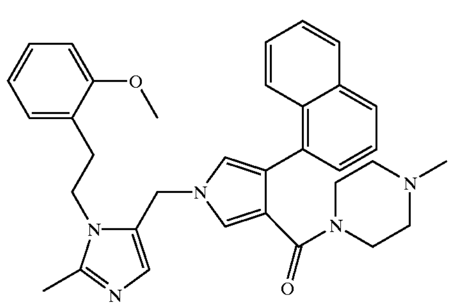 |
TABLE 1d-continued
| NO | COMPOUND STRUCTURE |
|----|--------------------|
| 27 | 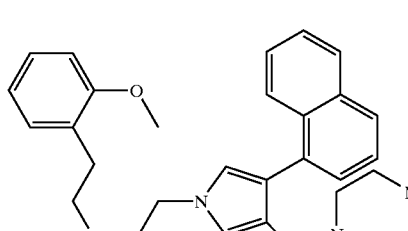 |
| 28 | 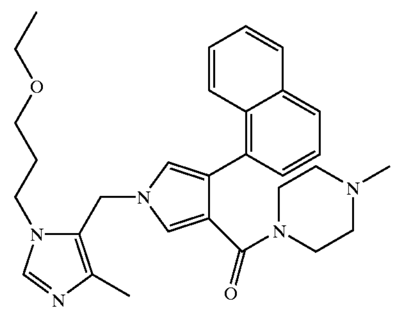 |
| 29 | 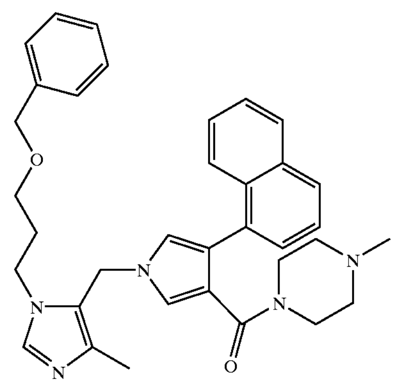 |
| 30 | 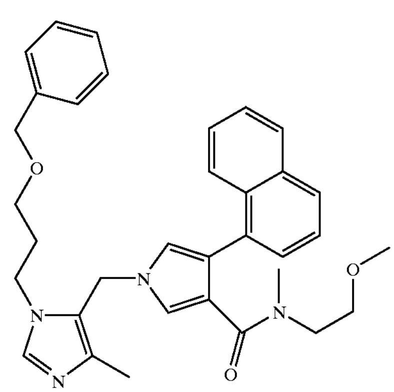 |

TABLE 1d-continued

| NO | COMPOUND STRUCTURE |
|---|---|
| 31 | 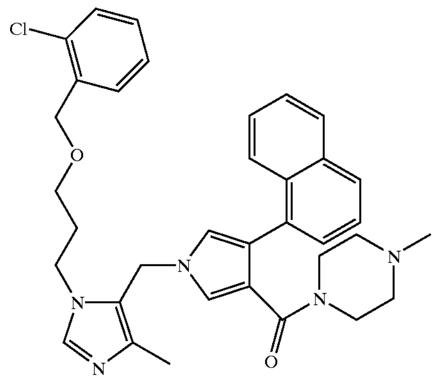 |
| 32 | 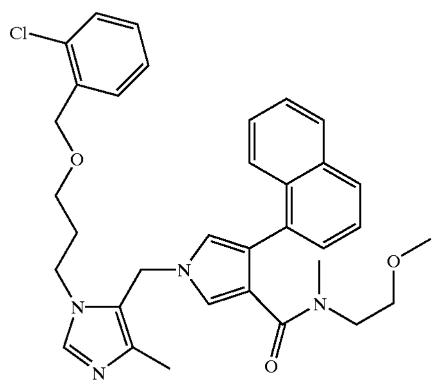 |

TABLE 1e

| NO | COMPOUND STRUCTURE |
|---|---|
| 33 | 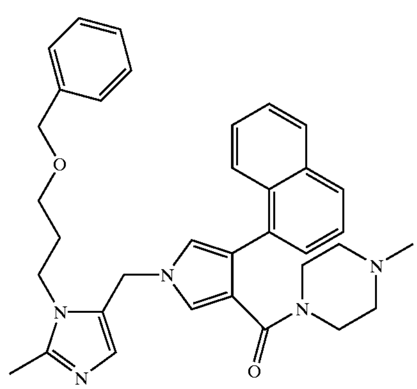 |

TABLE 1e-continued

| NO | COMPOUND STRUCTURE |
|---|---|
| 34 | 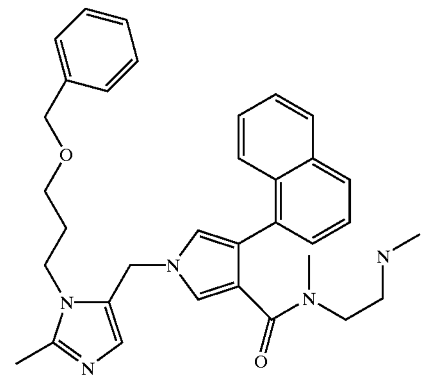 |
| 35 | 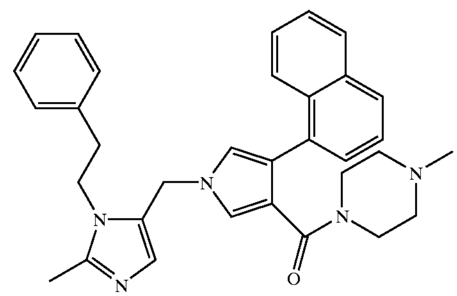 |
| 36 | 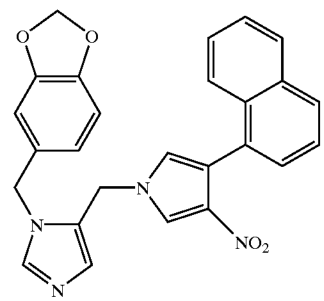 |
| 37 | 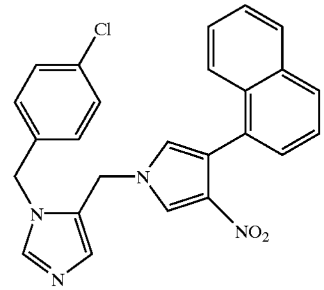 |
| 38 | 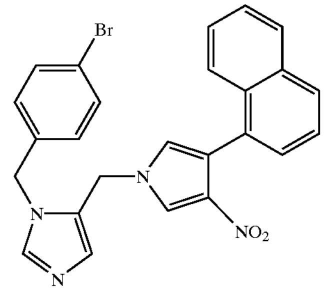 |

TABLE 1e-continued
| NO | COMPOUND STRUCTURE |
|----|--------------------|
| 39 | 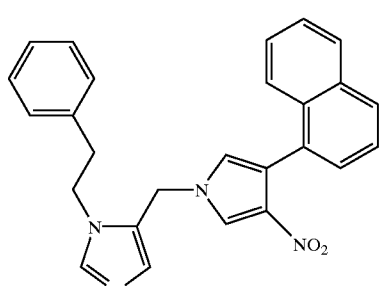 |
| 40 | 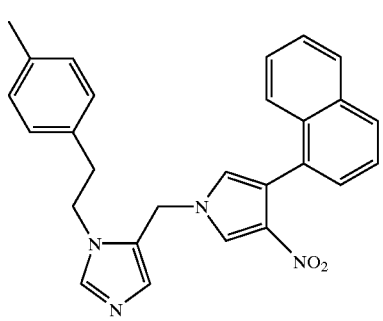 |
TABLE 1f
| NO | COMPOUND STRUCTURE |
|----|--------------------|
| 41 | 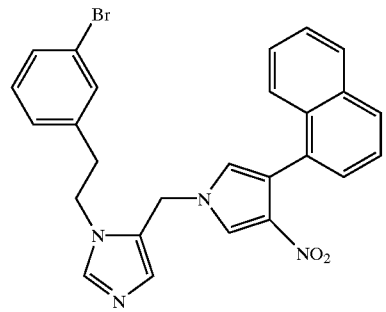 |
| 42 | 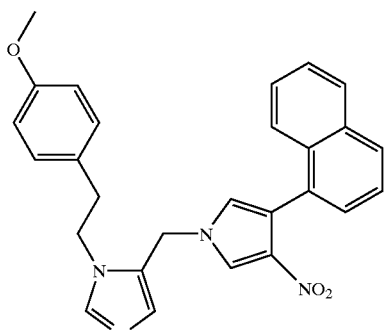 |
TABLE 1f-continued
| NO | COMPOUND STRUCTURE |
|----|--------------------|
| 43 | 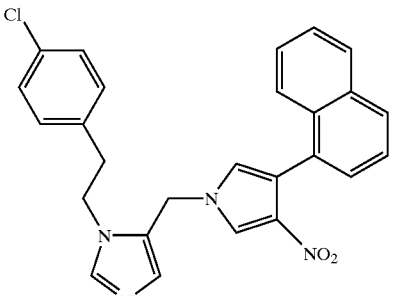 |
| 44 | 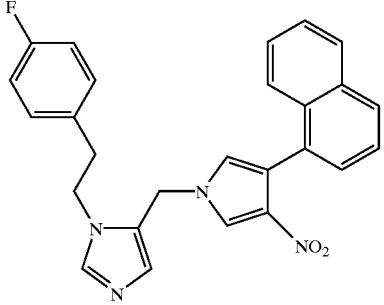 |
| 45 | 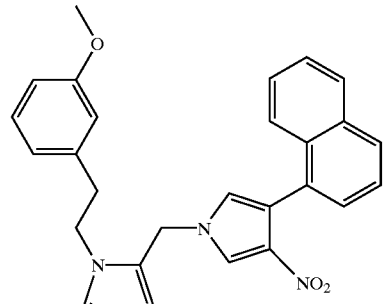 |
| 46 | 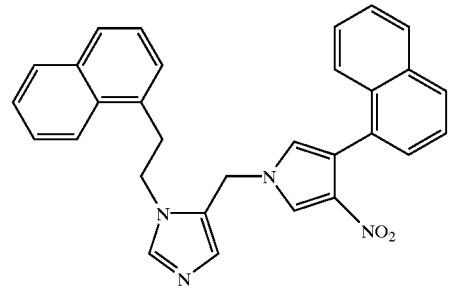 |

TABLE 1f-continued

| NO | COMPOUND STRUCTURE |
|----|--------------------|
| 47 | (structure) |
| 48 | (structure) |

TABLE 1g

| NO | COMPOUND STRUCTURE |
|----|--------------------|
| 49 | (structure) |
| 50 | (structure) |

TABLE 1g-continued

| NO | COMPOUND STRUCTURE |
|----|--------------------|
| 51 | (structure) |
| 52 | (structure) |
| 53 | (structure) |

TABLE 1g-continued

| NO | COMPOUND STRUCTURE |
|----|--------------------|
| 54 | 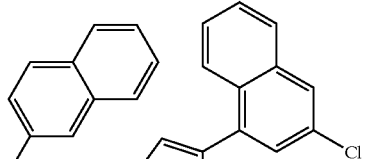 |

TABLE 1h

| NO | COMPOUND STRUCTURE |
|----|--------------------|
| 55 | 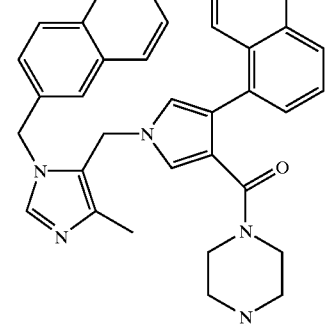 |

The compound of formula (1) as explained above can be prepared characterized by (a) coupling a compound represented by the following formula (2) with a compound represented by the following formula (3) to give the compound of formula (1);

(b) coupling a compound represented by the following formula (4a) with a compound represented by the following formula (5) to give a compound represented by the following formula (1a);

(c) coupling a compound represented by the following formula (4b) with a compound represented by the following formula (6) to give a compound represented by the following formula (1b);

(d) coupling a compound represented by the following formula (7) with a compound represented by the following formula (8) to give a compound represented by the following formula (1c);

or further introducing substituents in the presence of a base, or reducing. Therefore, these processes for preparing the compound of formula (1) are also subject matters to be provided by the present invention.

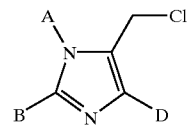

(2)

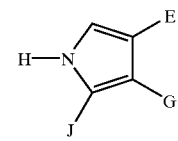

(3)

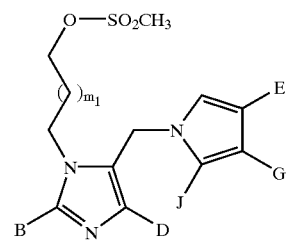

(4a)

(5)

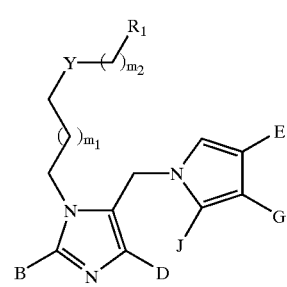

(1a)

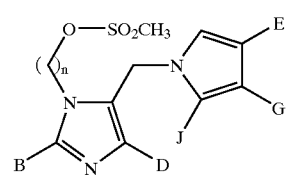

(4b)

(6)

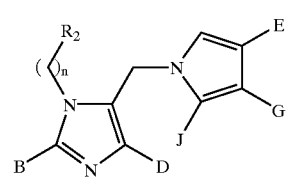

(1b)

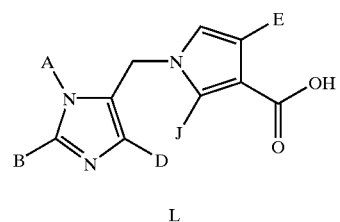

(7)

(8)

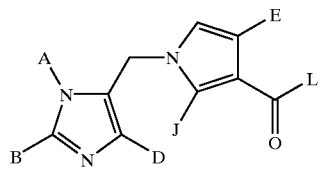

(1c)

in which

A, B, D, J, E, G, $m_1$, $m_2$, n, Y, $R_1$, $R_2$ and L are defined as previously described.

If desired, the coupling reactions in said process variants (a) to (d) for preparing the compound of formula (1) according to the present invention may be carried out in a solvent in the presence of a base. Any solvent which does not adversely affect the reaction may be used, but one or more selected from a group consisting of dimethylformamide, dichloromethane, tetrahydrofuran, chloroform and dimethylacetamide are preferable. As the base, one or more selected from a group consisting of sodium hydride, potassium t-butoxide, sodium bis(trimethylsilyl)amide, sodium amide and potassium bis(trimethylsilyl)amide can be mentioned.

The process variant (d) wherein carboxylic acid and hydroxy group are directly reacted with each other without using a reactive leaving group in the coupling reaction, may be preferably carried out particularly in the presence of a coupling agent. For example, coupling agents such as dicyclohexylcarbodiimide(DCC), 3-ethyl-3'-(dimethylamino)-propylcarbodiimide(EDC), bis-(2-oxo-3-oxazolidinyl)-phosphinic acid chloride (BOP-Cl), diphenylphosphorylazide(DPPA), isobutyl chloroformate, O-(7-azabenzotriazol-1-yl)-N,N,N',N'-tetramethyluronium hexafluorophosphate(HATU), etc. may be used together with 1-hydroxy benzotriazole (HOBT).

While the compounds used as starting materials in said processes for preparing the compound of formula (1) may be prepared according to the process depicted in the following Reaction Schemes 1 to 9.

First, as depicted in the following Reaction Scheme 1, the compound of formula (2) wherein 2-position of the imidazole ring is substituted by methyl group may be prepared by reacting an amine with dihydroxyacetone to give a thiolimidazole derivative, then by desulfurizing, methylating and halogenating (see: *J. Med. Chem.*, 33, 1312–1329, 1990). Further, the compound of formula (2) wherein 4-position of the imidazole ring is substituted may be prepared by the processes described in Reaction Scheme 2 or 3.

[Reaction Scheme 1]

When B is methyl and D is hydrogen:

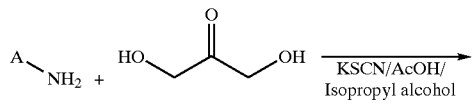

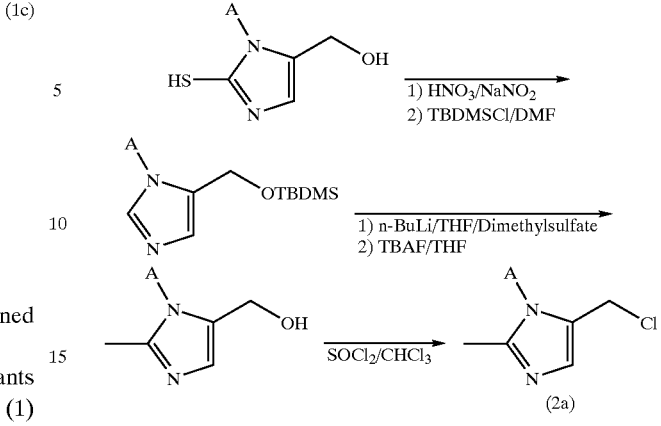

[Reaction Scheme 2]

When B is hydrogen and D is methyl:

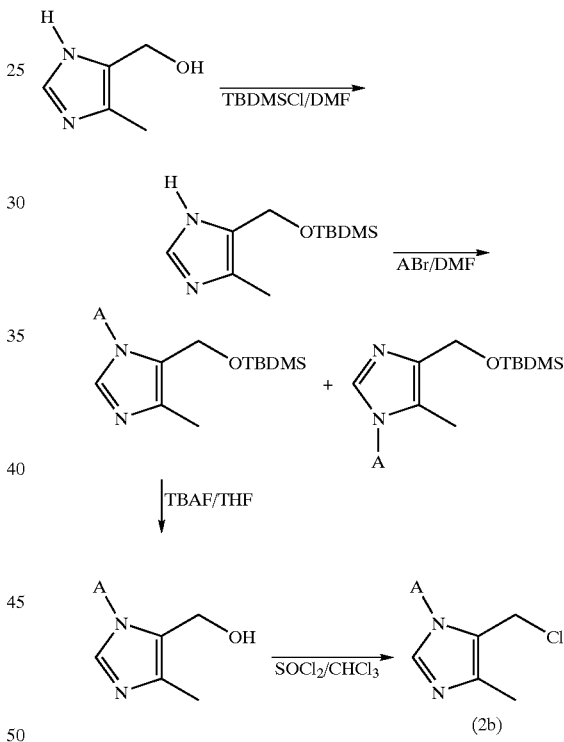

[Reaction Scheme 3]

When B is hydrogen an D is nitro:

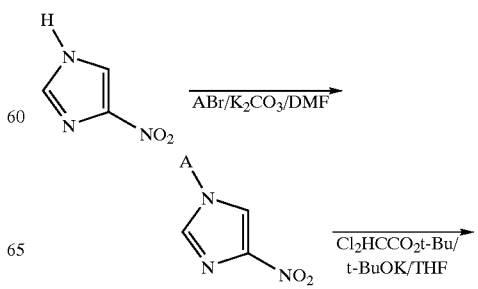

-continued

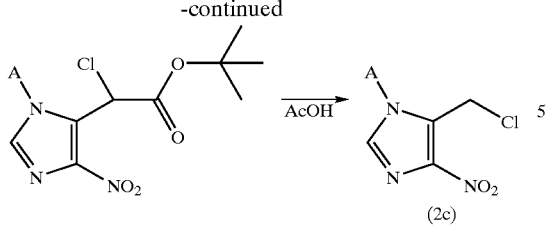

(2c)

In the above Reaction Schemes 1, 2, 3
A is defined as previously described,
TBDMS means t-butyldimethylsilyl,
TBAF means tetrabutylammoniumfluoride, and
they have the same meaning hereinafter.

The compound of formula (3) wherein J is hydrogen and G is the structure of

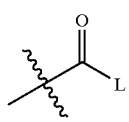

may be prepared from an aldehyde derivative of a formula E-CHO according to the process depicted in the following Reaction Scheme 4. The final step for giving the compound of formula (3a) from pyrrole carboxylic acid may be preferably carried out in the presence of the coupling agents as forementioned for process variants (a) to (d) (The preparation example for the starting compound of E-CHO where E is naphthyl substituted by halogen is described in Reaction Scheme 5). Further the compound of formula (3) wherein J is lower alkylthio or lower alkyl may be prepared by the processes described in the following Reaction Scheme 6 or 7, and the compound of same formula wherein G is nitro may be synthesized by the process described in the following Reaction Scheme 8.

[Reaction Scheme 4]

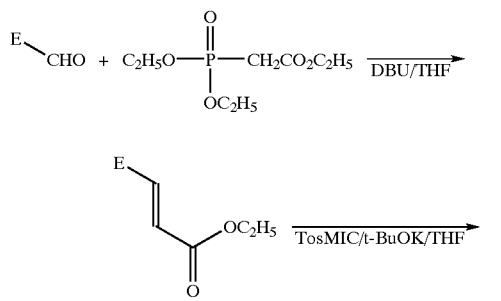

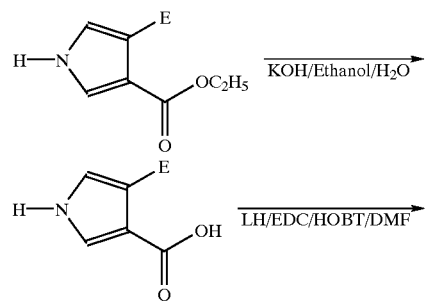

-continued

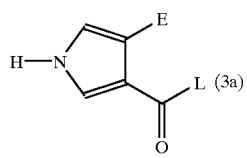

(3a)

[Reaction Scheme 5]

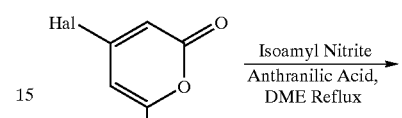

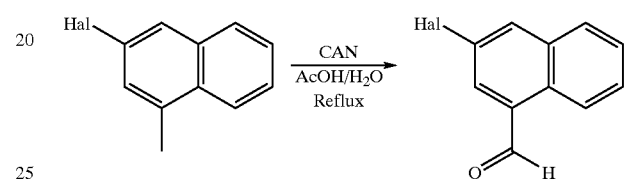

[Reaction Scheme 6]

When J is lower alkylthio (see: Tetrahedron Letter, 6155 (1992)):

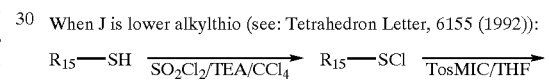

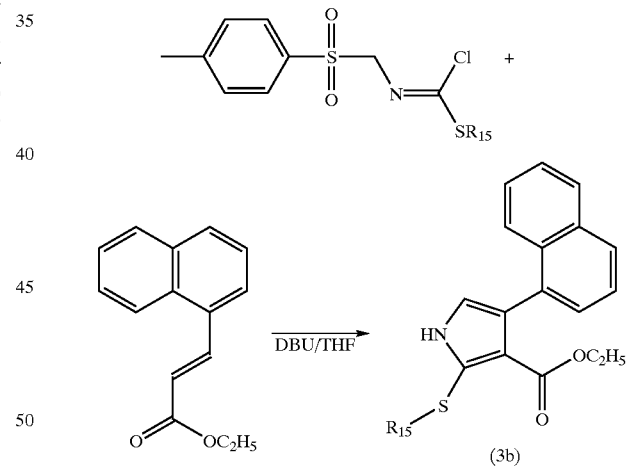

(3b)

[Reaction Scheme 7]

When J is lower alkyl:

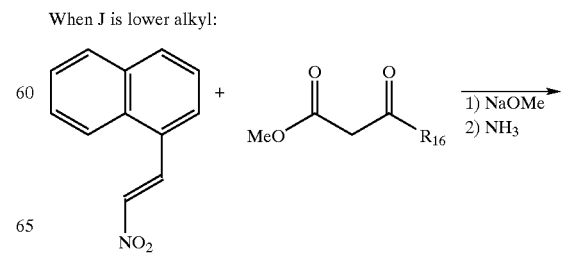

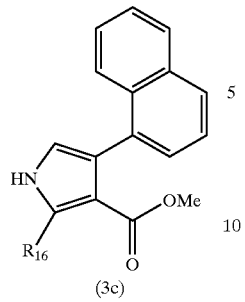

(3c)

[Reaction Scheme 8]

When G is nitro:

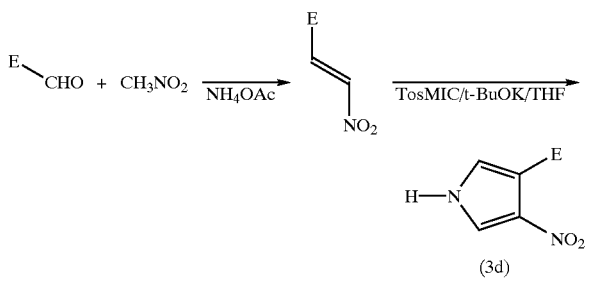

(3d)

In the above Reaction Schemes 4, 5, 6, 7, 8

E and L are defined as previously described,

Hal means halogen,

CAN means cerium ammonium nitrate, $R_{15}$ and $R_{16}$ represent lower alkyl,

DBU means 1,8-diazabicyclo[5,4,0]undec-7-ene,

TosMIC means tosylmethylisocyanide,

EDC means 1-(3-dimethylaminopropyl)-3-ethylcarbodiimide hydrochloride,

HOBT means 1-hydroxybenzotriazole hydrate, and

TEA means triethylamine.

While, The compounds of formulae (4a) and (4b) may be prepared from aminoalcohol derivatives according to the following Reaction Scheme 9.

[Reaction Scheme 9]

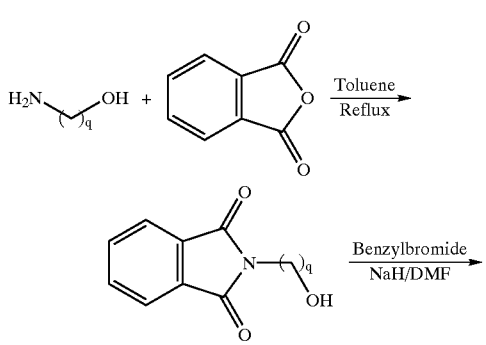

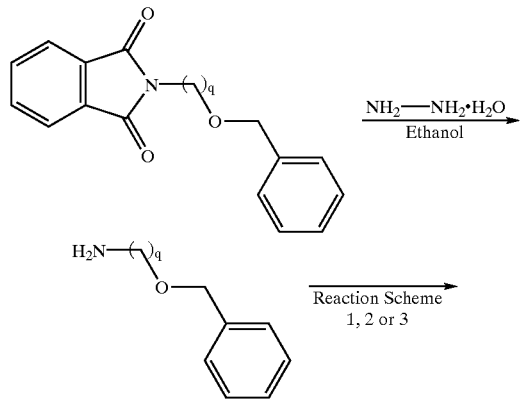

(4a) or (4b)

In the above Reaction Scheme 9

B, D, E, G and J are defined as previously described, q represents $m_1+2$ or n.

That is, the aminoalcohol derivative is reacted with phthalic acid anhydride in the presence of toluene to protect the amine moiety, and then the hydroxy group is reacted with benzylbromide in the presence of sodium hydride to be protected. The compound wherein both amino group and hydroxy group are protected is reacted with hydrazine to remove the phthalic protecting group, and thus, to give an amine compound wherein only the hydroxy group is protected by benzyl group. This amine compound is reacted according to the same procedure as Reaction Scheme 1, 2 or 3, and then the resulting compound is reacted with the compound of formula (3) and deprotected to give a primary alcohol compound. The primary alcohol is reacted with methanesulfonylchloride to give the desired compound of formula (4a) or (4b).

The reaction conditions including the amount of reactants, reaction temperature, reaction time, etc. in the processes according to the present invention can easily be determined by a person skilled in the art depending on the specific reactants.

In addition, the compound of formula (1) produced in the above processes in the form of a free base can easily be converted to a salt form according to the conventional methods known per se in this art.

After the reaction is completed, the resulting product may be further separated and purified by usual work-up processes, such as for example, chromatography, recrystallization, etc.

The present invention particularly the processes as described above, will be more specifically explained by the following Preparations and Examples. However, the processes for preparing the compound according to the present invention are not restricted to those which are explained in the present specification. That is, the present invented compound may be easily prepared by optionally combining the processes disclosed in the present specification or known in the prior references, and such a combination is a common knowledge to those skilled in the art to which the present invention pertains.

The compound of the present invention shows an inhibitory activity against farnesyl transferase, and thus can be effectively used as an anti-cancer agent. Further, due to the inhibitory activity against farnesyl transferase, the compound of formula (1) can be used as an agent useful for restenosis, atherosclerosis or viral infections. Therefore, it is another object of the present invention to provide compositions for treating cancer, restenosis, atherosclerosis and viral infections, respectively, each of which comprises as an active ingredient the compound of formula (1), pharmaceutically acceptable salt or isomer thereof together with the pharmaceutically acceptable carrier.

When the active compound according to the present invention is used for clinical purpose, it is preferably administered in an amount ranging from 1 to 100 mg per kg of body weight a day. The total daily dosage may be administered in one time or over several times. However, the specific administration dosage for the patient can be varied with the specific compound used, body weight of the subject patient, sex, hygienic condition, diet, time or method of administration, excretion rate, mixing ratio of the agent, severity of the disease to be treated, etc.

The compound of the present invention may be administered in the form of injections or oral preparations. Injections, for example, sterilized aqueous or oily suspension for injection, can be prepared according to the known procedure using suitable dispersing agent, wetting agent, or suspending agent. Solvents which can be used for preparing injections include water, Ringer's fluid and isotonic NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent and binding agent.

BEST MODE FOR CARRYING OUT THE INVENTION

The present invention will be more specifically explained in the following examples. The following Preparations are to explain the syntheses of intermediates used for preparing the final products, and the Examples are to explain the syntheses of final products through the reactions of the compounds obtained in the Preparations. However, it should be understood that these Preparations and Examples are intended to illustrate the present invention but not in any manner to limit the scope of the present invention.

Preparation 1

Preparations of 4-(naphthalen-1-yl)-1H-pyrrole-3-carboxylic acid 1-1) Preparation of 3-(naphthalen-1-yl)-acrylic acid ethylester 22.4 g(0.10 mol) of triethylphosphonoacetate was dissolved in 500 ml of acetonitrile and 30.4 g(2mol) of 1,8-diazabicyclo[5.4.0]undec-7-ene (1,5–5)(DBU) was slowly added thereto. 15.6 g(0.10 mol) of 1-naphthaldehyde dissolved in 20 ml of tetrahydrofuran was slowly added to the above reaction solution and the resulting mixture was stirred for 8 hours. The organic solvent was removed under reduced pressure, the residue thus obtained was dissolved in ethylacetate, washed twice with water, dried over magnesium sulfate and concentrated. The residue was subjected to column chromatography(eluent: n-hexane/ethylacetate=95/5, v/v) to give 20.3 g(0.090 mol, Yield 90%) of the title compound.

$^1$H NMR(CDCl$_3$) δ 1.33 (t, 3H), 4.10 (q, 2H), 6.75 (q, 1H), 7.50 (m, 3H), 7.73 (d, 1H), 7.85 (m, 2H), 8.10 (d, 1H), 8.21 (d, 1H)

FAB 227 (M+H)

1-2) Preparation of ethyl 4-(naphthalen-1-yl)-1H-pyrrole-3-carboxylate 5 g(18.9 mmol) of the compound prepared in Preparation 1-1) and 3.68 g(18.9 mmol) of tosylmethylisocyanide were dissolved in 100 ml of tetrahydrofuran. 2.55 g(22.7 mmol) of potassium t-butoxide dissolved in 100 ml of tetrahydrofuran was slowly added thereto and the resulting mixture was refluxed for 30 minutes. 100 ml of water was added to the reaction solution to stop the reaction and the solvent was removed under reduced pressure. The residue was extracted with diethylether, washed with saturated sodium chloride solution and dried over magnesium sulfate. Then, the solvent was removed under reduced pressure and the residue was subjected to column chromatography(eluent: ethylacetate/n-hexane=⅓, v/v) to give 3.85 g(14.5 mmol, Yield 77%) of the title compound.

$^1$H NMR(CDCl$_3$) δ 1.27 (t, 3H), 4.07 (q, 2H), 6.76 (s, 1H), 7.28–7.47 (m, 5H), 7.59 (s, 1H), 7.82 (m, 2H), 9.99 (s, 1H)

FAB 266 (M+H)

1-3) Preparation of 4-(naphthalen-1-yl)-1H-pyrrole-3-carboxylic acid

To 2.64 g(10 mmol) of the compound prepared in Preparation 1-2) in 50 ml of 50% ethanol was added 2.24 g(40 mmol) of potassium hydroxide and the resulting mixture was refluxed for 7 hours. After cooling to room temperature, the pH of the solution was adjusted to 4–5 and the product was extracted with ethylacetate. The extract was dried over sodium sulfate and the solvent was removed under reduced pressure to give 1.62 g(8.1 mmol, Yield 81%) of the title compound. The product thus obtained was used in the next reaction without purification.

$^1$H NMR(CDCl$_3$) δ 6.60 (s, 1H), 7.32–7.49 (m, 5H), 7.54 (s, 1H), 7.84 (m, 2H), 9.92 (s, 1H)

FAB 238 (M+H)

Preparation 2

Preparation of 3-[N-(2-methoxyethyl)-N-methyl]carbamoyl-4-(naphthalen-1-yl)-1H-pyrrole To 234 mg(1 mmol) prepared in Preparation 1-3) in 2 ml of dimethylformamide was added 230 mg(1.2 mmol) of EDC, 101 mg(1 mmol) of triethylamine and 162 mg(1.7 mmol) of HOBT and the resulting mixture was stirred for 5 minutes at 0° C. 124 mg(1 mmol) of N-(2-methoxyethyl)-N-methylamine hydrochloride was added thereto and the mixture was stirred for 5 hours at room temperature. The solvent was removed under reduced pressure and 10 ml of saturated aqueous potassium carbonate solution and 20 ml of ethylacetate were added. The organic layer washed with 10 ml of 1N aqueous hydrochloric acid solution, saturated sodium chloride solution and water, dried over sodium sulfate and then concentrated to give 246 mg(0.79 mmol, Yield 79%) of the title compound.

$^1$H NMR(CDCl$_3$) δ 2.46 (s, 2H), 2.80–3.40 (m, 8H), 3.40 (s, 1H), 6.80 (s, 1H), 7.00 (s, 1H), 7.42 (m, 4H), 7.73 (d, 1H), 7.81 (d, 1H), 8.17 (d, 1H), 10.66 (s, 1H)

FAB 309 (M+H)

Preparation 3

Preparation of 3-(morpholin-4-yl)carbonyl-4-(naphthalen-1-yl)-1H-pyrrole 234 mg(1 mmol) of the compound prepared in Preparation 1-3) was dissolved in 2 ml of dimethylformamide, 230 mg(1.2 mmol) of EDC and 162 mg(1.7 mmol) of HOBT were added and the resulting mixture was stirred for 5 minutes at 0° C. 87 mg(1mmol) of morpholine was added thereto and the mixture was stirred for 5 hours at room temperature. The solvent was removed under reduced pressure and 10 ml of saturated aqueous potassium carbonate solution was added. The resulting mixture was extracted with ethylacetate, washed with 10 ml of 1N aqueous hydrochloric acid solution, washed with aqueous sodium chloride solution and water, dried over sodium sulfate and then concentrated to give 243 mg(0.8 mmol, Yield 80%) of the title compound.

$^1$H NMR(CDCl$_3$) δ 2.13–3.52 (br, 8H), 6.54 (s, 1H), 7.31–7.51 (m, 5H) 7.53 (s, 1H), 7.81 (m, 2H), 9.93 (s, 1H)

FAB 307 (M+H)

Preparation 4

Preparation of 3-(4-methylpiperazin-1-yl) carbonyl-4-(naphthalen-1-yl)-1H-pyrrole The compound prepared in Preparation 1-3) was reacted with 4-methylpiperazine according to the same procedure as Preparation 2 to give the title compound with a yield of 75%.

$^1$H NMR(CDCl$_3$) δ 1.15 (br, 2H), 1.87 (br, 2H), 1.92 (s, 3H), 2.96 (br, 2H), 3.41 (br, 2H), 6.83 (s, 1H), 7.09 (s, 1H), 7.36–7.42 (m, 4H), 7.73 (d, 1H), 7.75 (d, 1H), 8.10 (d, 1H), 10.52 (s, 1H)

FAB (M+H): 320

Preparation 5

Preparation of 1-(3-benzyloxypropyl)-5-chloromethyl-1H-imidazole hydrochloride 5-1) Preparation of 3-hydroxypropyl phthalimide 15.2 g(0.2 mol) of 3-amino-1-propanol and 29.6 g(0.2 mol) of phthalic anhydride was refluxed with 500 ml of toluene using Dean-Stark apparatus for 24 hours(see: *Tetrahedron Letter*, 34, 2947, 1993). After the reaction, the solvent was removed under reduced pressure, and the residue was dissolved in 300 ml of dichloromethane and washed with 100 ml of water. The organic layer was dried over anhydrous sodium sulfate and the solvent was removed under reduced pressure to give 33.6 g(Yield 80%) of the title compound.

$^1$H NMR (CDCl$_3$) δ 1.57 (m, 2H), 3.17 (t, 2H), 3.42 (t, 2H), 7.68 (m, 5H)

FAB (M+H): 206

5-2) Preparation of 3-benzyloxypropyl amine

To 20.5 g(0.1 mol) of the compound prepared in Preparation 5-1) in 40 ml of dimethylformamide was added 4.4 g(0.11 mol) of sodium hydride(60%). 18.9 g(0.11 mol) of benzyl bromide was added and the resulting mixture was reacted for 12 hours. After removal of solvent the reaction, solvent was removed and the residue was dissolved in ethylacetate and the organic layer was washed with saturated sodium bicarbonate solution. After removal of solvent, 200 ml of ethanol and 12.5 g(0.25 mol) of hydrazine hydrate was added thereto, and the resulting mixture was refluxed for 3 hours. After the reaction, solvent was removed under reduced pressure. The residue was dissolved in 200 ml of dichloromethane and the organic layer was washed with saturated sodium bicarbonate solution. 200 ml of 1N aqueous hydrochloric acid solution was added and the organic layer was removed. To the aqueous layer was added 200 ml of dichloromethane, and the resulting solution was basified with 6N sodium hydroxide solution. The organic layer was separated and the solvent was removed under reduced pressure to give 8.3 g(Yield 50%) of the title compound.

$^1$H NMR(CDCl$_3$) δ 1.76(m, 2H), 2.30(br, 2H), 2.83 (t, 2H), 3.54(t, 2H), 4.49(s, 2H), 7.32(m, 5H)

FAB 166 (M+H)

Preparation 5-3)

Preparation of 1-(3-benzyloxypropyl)-5-hydroxy methyl-1H-imidazole

The title compound was prepared by modifying the method described in the literature (see: *J. Med. Chem.*, 33, 1312–1329, 1990) from dihydroxyacetone dimer and the compound prepared in Preparation 5-2). 4.95 g(30 mmol) of 3-benzyloxypropylamine, 2.97 g(16.5 mmol) of dihydroxyacetone dimer and 3.20 g(33 mmol) of potassium thiocyanide were added to 30 ml of isopropyl alcohol, 6 ml of acetic acid was added thereto, and the resulting mixture was reacted for 48 hours at room temperature. After the reaction, solvent was removed, 100 ml of ethylacetate was added, and the mixture was washed twice with 100 ml of water. The solvent was removed under reduced pressure, 30 ml of 30% nitric acid and 6.9 mg(0.1 mmol) of NaNO$_2$ were added to the residue and stirred for 2 hours. To the reaction mixture was added 20 ml of ethylacetate. The organic layer was removed and 100 ml of ethylacetate was added to the aqueous layer. After the mixture was basified to pH12 using 6N aqueous sodium hydroxide solution, the organic layer was separated and dried over anhydrous sodium sulfate. The solvent was removed under reduced pressure and the residue was concentrated. The concentrate was subjected to column chromatography(eluent: dichloromethane/methanol=93/7, v/v) to give 2.5 g(Yield 38%) of the title compound.

$^1$H NMR(CDCl$_3$) δ 2.05 (m, 2H), 3.41 (t, 2H), 4.10 (t, 2H), 4.45 (s, 2H), 4.55 (s+br, 3H), 6.84(s, 1H), 7.32(m, 5H), 7.42(s, 1H)

FAB 247 (M+H)

Preparation 5-4)

Preparation of 1-(3-benzyloxypropyl)-5-chloromethyl-1H-imidazole hydrochloride 246 mg(1 mmol) of the compound prepared in Preparation 5-3) was dissolved in 3 ml of chloroform and 355 mg(3mmol) of thionyl chloride was added dropwise at 0° C. After the resulting solution was stirred for 2 hours, the solvent was removed under reduced pressure and the remaining hydrochloride was removed to give the title compound with a yield of 95%. The product thus obtained was directly used in the next reaction without purification.

Preparation 6

Preparation of 1-[2-(thiophen-2-yl)ethyl]-5-chloromethyl-1H-imidazole hydrochloride 6-1) Preparation of 1-[2-(thiophen-2-yl)ethyl]-5-hydroxymethyl-1H-imidazole The title compound was prepared by modifying the method described in the literature (see: *J. Med. Chem.*, 33, 1312–1329, 1990) from dihydroxyacetone dimer and 2-(thiophen-2-yl)ethylamine. 1.37 g(10 mmol) of 2-(thiophen-2-yl)ethylamine, 1.08 g(6 mmol) of dihydroxyacetone dimer and 1.15 g(11 mmol) of potassium thiocyanide were added to 10 ml of isopropyl alcohol, 2 ml of acetic acid was added thereto, and the resulting mixture was stirred for 48 hours at room temperature. The reaction mixture was filtered and the resulting solid was washed twice with 5 ml of isopropyl alcohol and twice with 5 ml of water. The filtered solid was added to 20 ml of 10% aqueous nitric acid solution. To the reaction solution was added 10 mg of sodium nitrite at 0° C. and the mixture was reacted for 1 hour at room temperature. The aqueous solution was washed with 10 ml of ethyl acetate, basified and recrystallized to give 1.16 g(Yield 49%) of the title compound.

$^1$H NMR(CDCl$_3$) δ 3.31 (t, 2H), 4.25 (t, 2H), 4.55 (s, 2H), 6.70 (d, 1H), 6.90 (m, 2H), 7.15(d, 1H), 7.25(s, 1H)

FAB 233 (M+H), C$_{10}$H$_{12}$N$_2$OS(M)

6-2) Preparation of 1-[2-(thiophen-2-yl)ethyl]-5-chloromethyl-1H-imidazole hydrochloride 233 mg(1 mmol) of the compound prepared in Preparation 6-1) was dissolved in 3 ml of chloroform and 355 mg(3 mmol) of thionyl chloride was added dropwise at 0° C. After the reaction mixture was stirred for 2 hours, the solvent was removed under reduced pressure, and the remaining hydrochloride was removed to give the title compound with a yield of 95%. The product thus obtained was directly used in the next reaction without purification.

Preparation 7

Preparation of 1-(furan-2-yl)methyl-5-chloromethyl-1H-imidazole hydrochloride 7-1) Preparation of 1-(furan-2-yl)methyl-5-hydroxymethyl-1H-imidazole 0.97 g(10 mmol) of furfurylamine, 1.08 g(6 mmol) of dihydroxyacetone dimer and 1.15 g(11 mmol) of potassium thiocyanide were added to 10 ml of isopropyl alcohol, 2 ml of acetic acid was added thereto, and the resulting mixture was stirred for 48 hours at room temperature. The reaction mixture was filtered and the resulting solid was washed twice with 5 ml of isopropyl alcohol and twice with 5 ml of water. The filtered solid was added to 20 ml of 10% aqueous nitric acid solution. To the reaction solution was added 10 mg of sodium nitrite at 0° C. and the mixture was reacted for 1 hour at room temperature. The aqueous solution was washed with 10 ml of ethylacetate, basified and recrystallized to give 1.07 g(Yield 60%) of the title compound.

$^1$H NMR(CDCl$_3$) δ 4.63 (s+br, 3H), 5.29 (s, 2H), 6.37 (d, 1H), 6.40 (m, 1H), 6.99 (s, 1H), 7.41(s, 1H), 7.65(s, 1H)

FAB 179 (M+H), C$_9$H$_{10}$N$_2$O$_2$(M)

7-2) Preparation of 1-(furan-2-yl)methyl-5-chloromethyl-1H-imidazole hydrochloride 205 mg(1 mmol) of the compound prepared in Preparation 7-1) was dissolved in 3 ml of chloroform and 355 mg(3 mmol) of thionyl chloride was added dropwise thereto at 30° C. After the reaction mixture was stirred for 2 hours, the solvent was removed under reduced pressure, and the remaining hydrochloride was removed to give the title compound with a yield of 95%. The product thus obtained was directly used in the next reaction without purification.

Preparation 8

Preparation of 1-(1-benzylpiperidin-4-yl)-5-chloromethyl-1H-imidazole hydrochloride 8-1) Preparation of 1-(1-benzylpiperidin-4-yl)-5-hydroxymethyl-1H-imidazole 3.0 g(11.4 mmol) of 4-amino-1-benzylpiperidine hydrochloride, 1.00 g(5.7 mmol) of dihydroxyacetone dimer and 1.8 g(18.2 mmol) of potassium thiocyanate were added to 10 ml of isopropyl alcohol, 2 ml of acetic acid was added thereto, and the resulting mixture was stirred for 48 hours at room temperature. The reaction mixture was filtered and the resulting solid was washed twice with 5 ml of isopropyl alcohol and twice with 5 ml of water. The filtered solid was added to 20 ml of 10% aqueous nitric acid solution and cooled to 0° C. To the reaction solution was added 10 mg of sodium nitrite and the mixture was reacted for 1 hour at room temperature. The aqueous solution was washed with 10 ml of ethylacetate, basified and recrystallized to give 1.2 g(Yield 38%) of the title compound.

$^1$H NMR(CDCl$_3$) δ 1.94(m, 2H), 2.01(m, 2H), 2.12(m, 2H), 2.97(d, 2H), 3.52(s, 2H), 4.08(m, 1H), 4.54(s, 2H), 6.72(s, 1H), 7.20–7.31(m, 5H), 7.45(s, 1H)

FAB 272 (M+H), C$_{16}$H$_{21}$N$_3$O(M)

8-2) Preparation of 1-(1-benzylpiperidin-4-yl)-5-chloromethyl-1H-imidazole hydrochloride 271 mg(1 mmol) of the compound prepared in Preparation 8-1) was dissolved in 3 ml of chloroform and 355 mg(3 mmol) of thionyl chloride was added dropwise thereto at 0° C. After the reaction mixture was stirred for 2 hours, the solvent was removed under reduced pressure, and the remaining hydrochloride was removed to give the title compound with a yield of 95%. The product thus obtained was directly used in the next reaction without purification.

EXAMPLE 1

Preparation of 1-[1-(3-benzyloxypropyl)-1H-imidazol-5-yl]methyl-3-[N-(2-methoxyethyl)-N-methyl]carbamoyl-4-(naphthalen-1-yl)-1H-pyrrole (1)

620 mg(2 mmol) of the compound prepared in Preparation 2 was dissolved in 20 ml of dimethylformamide, 264 mg(6.6 mmol) of sodium hydride(60%) was added at 0° C., and the resulting mixture was stirred for 5 minutes. 601 mg(2.2 mmol) of the compound prepared in Preparation 5-4) was added thereto and the mixture was stirred for 3 hours at room temperature. The solvent was removed under reduced pressure and 30 ml of water was added thereto. The resulting mixture was extracted twice with 100 ml of ethylacetate and the combined organic layer was dried over anhydrous sodium sulfate and concentrated. The concentrate was subjected to column chromatography(eluent: dichloromethane/methanol=95/5, v/v) to give 780 mg(Yield 67%) of the title compound.

$^1$H NMR(CDCl$_3$) δ 1.78(m, 2H), 2.40(br, 2H), 2.71(br, 1H), 2.90–3.30(m, 5H), 3.25–3.40(m, 3H), 3.99(t, 2H), 4.41(s, 2H), 4.56(br, 1H), 5.09(s, 2H), 6.66(s, 1H), 7.05(s, 1H), 7.13(s, 1H), 7.20–7.50(m, 9H), 7.62(s, 1H), 7.72(d, 1H), 7.81(d, 1H), 8.05(d, 1H)

FAB (M+H) 537, C$_{33}$H$_{36}$N$_4$O$_3$(M)

EXAMPLE 2

Preparation of 1-[1-(3-benzyloxypropyl)-1H-imidazol-5-yl]methyl-3-(morpholin-4-yl)carbonyl-4-(naphthalen-1-yl)-1H-pyrrole(2)

620 mg(2 mmol) of the compound prepared in Preparation 3 was dissolved in 20 ml of dimethylformamide, 264 mg(6.6 mmol) of sodium hydride(60%) was added at 0° C., and the resulting mixture was stirred for 5 minutes. 601 mg(2.2 mmol) of the compound prepared in Preparation 5-4) was added thereto and the mixture was stirred for 3 hours at room temperature. The solvent was removed under reduced pressure and 30 ml of water was added thereto. The resulting mixture was extracted twice with 100 ml of ethylacetate and the combined organic layer was dried over anhydrous sodium sulfate and concentrated. The concentrate was subjected to column chromatography(eluent: dichloromethane/methanol=95/5, v/v) to give 810 mg(Yield 75%) of the title compound.

$^1$H NMR(CDCl$_3$) δ 1.79(m, 2H), 2.60–3.30(br, 8H), 3.36 (t, 2H), 4.00(t, 2H), 4.42(s, 2H), 5.11(s, 2H), 6.66(s, 1H), 7.05(s, 1H), 7.13(s, 1H), 7.20–7.50(m, 9H), 7.62(s, 1H), 7.72(d, 1H), 7.81(d, 1H), 8.05(d, 1H)

FAB (M+H) 535, C$_{33}$H$_{34}$N$_4$O$_3$(M)

EXAMPLE 3

Preparation of 1-[1-(3-benzyloxypropyl)-1H-imidazol-5-yl]methyl-3-(4-methylpiperazin-1-yl)carbonyl-4-(naphthalen-1-yl)-1H-pyrrole(3)

640 mg(2 mmol of the compound prepared in Preparation 4 was dissolved in 20 ml of dimethylformamide, 264 mg(6.6 mmol) of sodium hydride(60%) was added at 0° C., and the resulting mixture was stirred for 5 minutes. 601 mg(2.2 mmol) of the compound prepared in Preparation 5-4) was added thereto and the mixture was stirred for 3 hours at room temperature. The solvent was removed under reduced pressure and 30 ml of water was added thereto. The resulting mixture was extracted twice with 100 ml of ethylacetate and the combined organic layer was dried over anhydrous sodium sulfate and concentrated. The concentrate was subjected to column chromatography(eluent: dichloromethane/methanol=95/5, v/v) to give 750 mg(Yield 68%) of the title compound.

$^1$H (NMR(CDCl$_3$) δ 1.07(br, 2H), 1.76(m, 2H), 1.90–2.05 (br+s, 5H), 3.00 (br, 1H), 3.10–3.60(br+t, 5H), 3.95(t, 2H), 4.44(s, 2H), 5.07(s, 2H), 6.66(d, 1H), 7.04(s, 1H), 7.13(s, 1H), 7.20–7.31(m, 6H), 7.32–7.50(m, 4H), 7.75(d, 1H), 7.80(d, 1H), 8.00(d, 1H)

FAB (M+H) 548, C$_{34}$H$_{37}$N$_5$O$_2$(M)

EXAMPLE 4

Preparation of 3-[N-(2-methoxyethyl)-N-methyl]carbamoyl-4-(naphthalen-1-yl)-1-[1-(3-phenoxypropyl)-1H-imidazol-5-yl]methyl-1H-pyrrole(4)

4-1) Preparation of 1-[1-(3-hydroxypropyl)-1H-imidazol-5-yl]methyl-3-[N-(2-methoxyethyl)-N-methyl]carbamoyl-4-(naphthalen-1-yl)-1H-pyrrole 536 mg (1 mmol) of the compound prepared in Example 1, 20 mg of Pd/C(10%) and 2.2 g(47 mmol) of formic acid were added to 50 ml of methanol and the resulting mixture was stirred for 96 hours(see: *J. Org. Chem.* 3443, 1979). After the reaction, the solid was filtered out and the solvent was removed under reduced pressure. 20 ml of ethylacetate was added thereto, which was then washed with 10 ml of saturated aqueous sodium bicarbonate solution. The solvent was removed and the residue was subjected to column chromatography(eluent: dichloromethane/methanol=93/7, v/v) to give 313 mg(Yield 70%) of the title compound.

$^1$H NMR(CDCl$_3$) δ 1.33(m, 2H), 2.37(s, 2H), 2.68(m, 1H), 2.85–3.10(m, 6H), 3.29(br, 1H), 3.51(t, 2H), 4.04(t, 2H), 5.03(br, 1H), 5.12(s, 2H), 6.71(s, 1H), 7.12(s, 1H), 7.20(s, 1H), 7.25(d, 1H), 7.39(m, 3H), 7.72(d, 1H), 7.78(m, 2H), 7.99(d, 1H)

FAB (M+H) 447, C$_{26}$H$_{30}$N$_4$O$_3$(M)

4-2) Preparation of 3-[N-(2-methoxyethyl)-N-methyl]carbamoyl-1-[1-(3-methanesulfonyloxypropyl)-1H-imidazol-5-yl]methyl-4-(naphthalen-1-yl)-1H-pyrrole 223 mg (0.5 mmol) of the compound prepared in Example 4-1) was added to 10 ml of dichloromethane solution wherein 55 mg (0.55 mmol) of triethylamine and 63 mg(0.55 mmol) of methanesulfonylchloride were dissolved and the resulting mixture was stirred for 4 hours. 10 ml of water was added and the organic layer was separated. The organic layer was dried over anhydrous sodium sulfate and concentrated under reduced pressure. The residue was subjected to column chromatography(eluent: dichloromethane/methanol=90/10, v/v) to give 160 mg(Yield 60%) of the title compound.

$^1$H NMR (CDCl$_3$) δ 1.95(m, 2H), 2.42(s, 2H), 2.70(m, 1H), 2.85–3.18(m, 8H), 3.29(s, 1H), 3.45(m, 1H), 4.19(m, 4H), 5.25(s, 2H), 6.80(d, 1H), 7.17(s, 1H), 7.20–7.60(m, 5H), 7.73(d, 1H), 7.75(d, 1H), 7.99(d, 1H), 8.42(br, 1H)

FAB (M+H) 525, C$_{27}$H$_{32}$N$_4$O$_5$S(M)

4-3) Preparation of 3-[N-(2-methoxyethyl)-N-methyl]carbamoyl-4-(naphthalen-1-yl)-1-[1-(3-phenoxypropyl)-1H-imidazol-5-yl]methyl-1H-pyrrole 4.8 mg(0.12 mmol) of sodium hydride(60%) and 10.3 mg(0.11 mmol) of phenol were added to 2 ml of dimethylformamide. To this mixture was added 52 mg(0.1 mmol) of the compound prepared in Example 4-2) and the resulting mixture was stirred for 2 hours at 60° C. The mixture was concentrated by removing the solvent under reduced pressure. 10 ml of ethylacetate was added to the residue, which was then washed with saturated aqueous sodium bicarbonate solution. The solution was concentrated and the residue was subjected to column chromatography(eluent: dichloromethane/methanol=93/7, v/v) to give 23 mg(Yield 45%) of the title compound.

$^1$H NMR(CDCl$_3$) δ 2.03(m, 2H), 2.40(br, 2H), 2.71(br, 1H), 2.90–3.22(br, 5H), 3.31(br, 1H), 3.88(t, 2H), 4.18(m,

3H), 5.15(s, 2H), 6.72(d, 1H), 6.78(d, 2H), 6.93(t, 1H), 7.10(s, 1H), 7.21(m, 3H), 7.35(s, 1H), 7.39(m, 3H), 7.74(d, 1H), 7.82(d, 1H), 8.03(m, 2H)

FAB (M+H) 523, $C_{32}H_{34}N_4O_3(M)$

EXAMPLE 5

Preparation of 3-[N-(2-methoxyethyl)-N-methyl] carbamoyl-4-(naphthalen-1-yl)-1-[1-(3-thiophenoxypropyl)-1H-imidazol-5-yl]methyl-1H-pyrrole(5)

4.8 mg(0.12 mmol) of sodium hydride(60%) and 12.1 mg(0.11 mmol) of thiophenol were added to 2 ml of dimethylformamide. To this mixture was added 52 mg(0.1 mmol) of the compound prepared in Example 4-2) and the resulting mixture was stirred for 2 hours at 60° C. The solvent was removed by removing the solvent under reduced pressure. 10 ml of ethylacetate was added to the residue, which was then washed with saturated aqueous sodium bicarbonate solution. The solution was concentrated and the residue was subjected to column chromatography(eluent: dichloromethane/methanol=93/7, v/v) to give 29.6 mg(Yield 55%) of the title compound.

$^1$H NMR(CDCl$_3$) δ 1.88(m, 2H), 2.41(br, 2H), 2.60–3.20 (m, 8H), 3.32(br, 1H), 4.04(m, 3H), 5.13(s, 2H), 6.70(s, 1H), 7.05–7.60(m, 11H), 7.73(d, 1H), 7.82(m, 2H), 8.03(d, 1H)

FAB (M+H) 539, $C_{32}H_{34}N_4O_2S(M)$

EXAMPLE 6

Preparation of 3-(morpholin-4-yl)carbonyl-4-(naphthalen-1-yl)-1-[1-(3-phenoxypropyl)-1H-imidazol-5-yl]methyl-1H-pyrrole(6)

The title compound was obtained with a yield of 90% according to the same procedure as Example 4 except that the compound of Example 2 was used instead of the compound of Example 1 in step 4-1).

$^1$H NMR(CDCl$_3$) δ 1.25(m, 2H), 2.24(m, 3H), 2.70–3.35 (br, 5H), 3.98(t, 2H), 4.43(t, 2H), 5.29(s, 2H), 6.77(m, 2H), 6.90(m, 1H), 7.15–7.50(m, 10H), 7.75(d, 1H), (7.79(d, 1H), 7.98(d, 1H)

FAB (M+H) 521, $C_{32}H_{32}N_4O_3(M)$

EXAMPLE 7

Preparation of 3-(4-methylpiperazin-1-yl)carbonyl-4-(naphthalen-1-yl)-1-[1-(3-phenoxypropyl)-1H-imidazol-5-yl]methyl-1H-pyrrole(7)

The title compound was obtained with a yield of 87% according to the same procedure as Example 4 except that the compound of Example 3 was used instead of the compound of Example 1 in step 4-1).

$^1$H NMR(CDCl$_3$) δ 1.07(br, 2H), 1.70–2.0(br+m+s, 6H), 2.49(br, 1H), 2.91(br, 2H), 3.31(br, 2H), 3.81(t, 2H), 4.04(t, 2H), 5.05(s, 2H), 6.70(d, 1H), 6.78(m, 2H), 6.90(m, 1H), 7.11(m, 2H), 7.20(m, 2H), 7.29(m, 1H), 7.37(m, 3H), 7.49(s, 1H), 7.73(d, 1H), 7.80(d, 1H), 8.00(d, 1H)

FAB (M+H) 534, $C_{33}H_{35}N_5O_2(M)$

EXAMPLE 8

Preparation of 3-[N-(2-methoxyethyl)-N-methyl] carbamoyl-4-(naphthalen-1-yl)-1-[1-(3-thioethoxypropyl)-1H-imidazol-5-yl]methyl-1H-pyrrole(8)

4.8 mg(0.12 mmol) of sodium hydride(60%) and 6.8 mg(0.11 mmol) of ethanethiol were added to 2 ml of dimethylformamide. To this mixture was added 52 mg(0.1 mmol) of the compound prepared in Example 4-2) and the resulting mixture was stirred for 2 hours at room temperature. The solvent was removed under reduced pressure. 10 ml of ethylacetate was added to the residue, which was then washed with saturated aqueous sodium bicarbonate solution. The solution was concentrated and the residue was subjected to column chromatography(eluent: dichloromethane/methanol=93/7, v/v) to give 21 mg(Yield 43%) of the title compound.

$^1$H NMR(CDCl$_3$) δ 1.69(t, 3H), 1.87(m, 2H), 2.25–2.85 (m, 7H), 2.90–3.15(m, 5H), 3.34(br, 1H), 4.03(t, 2H), 4.57 (br, 1H), 5.17(s, 2H), 6.76(s, 1H), 7.12(s, 1H), 7.20(s, 1H), 7.37–7.46(m, 4H), 7.78(d, 1H), 7.84(m, 2H), 8.08(d, 1H)

FAB (M+H) 491, $C_{28}H_{34}N_4O_2S$ (M)

EXAMPLE 9

Preparation of 3-[N-(2-methoxyethyl)-N-methyl] carbamoyl-1-{1-[3-(morpholin-4-yl)propyl]-1H-imidazol-5-yl}methyl-4-(naphthalen-1-yl)-1H-pyrrole(9)

4.8 mg(0.12 mmol) of sodium hydride(60%) and 9.6 mg(0.11 mmol) of morpholine were added to 2 ml of dimethylformamide. To this mixture was added 52 mg(0.1 mmol) of the compound prepared in Example 4-2) and the resulting mixture was stirred for 2 hours at room temperature. The mixture was removed under reduced pressure. 10 ml of ethylacetate was added to the residue, which was then washed with saturated aqueous sodium bicarbonate solution. The solution was concentrated and the residue was subjected to column chromatography(eluent: dichloromethane/methanol=93/7, v/v) to give 20 mg(Yield 41%) of the title compound.

$^1$H NMR(CDCl$_3$) δ 1.84(m, 2H), 2.30–2.80(m, 8H), 2.85–3.40(m, 6H), 3.65–3.85(m, 6H), 4.00(t, 2H), 5.21(s, 2H), 6.80(s, 1H), 7.10–7.50(m, 6H), 7.61(s, 1H), 7.75(d, 1H), 7.91(d, 1H), 8.07(d, 1H)

FAB (M+H) 516, $C_{30}H_{37}N_5O_3(M)$

EXAMPLE 10

Preparation of 3-[N-(2-methoxyethyl)-N-methyl] carbamoyl-4-(naphthalen-1-yl)-1-{1-[2-(thiophen-2-yl)ethyl]-1H-imidazol-5-yl}methyl-1H-pyrrole(10)

The title compound was obtained with a yield of 71% according to the same procedure as Example 1 using the compound prepared in Preparation 2 and the compound prepared in Preparation 6-2) as starting materials.

$^1$H NMR(CDCl$_3$) δ 2.24(br, 1H), 2.39(br, 2H), 2.71(br, 1H), 2.90–3.17(m, 6H), 3.29(m, 2H), 4.05(t, 2H), 4.88(s, 2H), 6.61(s, 1H), 6.70(d, 1H), 6.90(m, 1H), 7.04(s, 1H), 7.10(s, 1H), 7.14(d, 1H), 7.30–7.50(m, 5H), 7.73(d, 1H), 7.81(d, 1H), 8.05(d, 1H)

FAB (M+H) 499, $C_{29}H_{30}N_4O_2S(M)$

EXAMPLE 11

Preparation of 3-(4-methylpiperazin-1-yl)carbonyl-4-(naphthalen-1-yl)-1-{1-[2-(thiophen-2-yl)ethyl]-1H-imidazol-5-yl}methyl-1H-pyrrole(11)

640 mg(2 mmol) of the compound prepared in Preparation 4 was dissolved in 20 ml of dimethylformamide, 264 mg(6.6 mmol) of sodium hydride(60%) was added at 0° C., and the resulting miture was stirred for 5 minutes. 570 mg(2.2 mmol) of hte compound prepared in Preparation 6-2) was added thereto and the mixture was stirred for 3 hours at room temperature. The solvent was removed under reduced pressure and 30 ml of water was added thereto. The resulting mixture was extracted twice with 100 ml of ethylacetate the combined oragnic layer was dried over anhydrous sodium sulfate and concentrated. The concentrate was subjected to column chromatography(eluent: dichloromethane/methanol=95/5, v/v) to give 750 mg(Yield 74%) of the title compound.

$^1$H NMR(CDCl$_3$) δ 1.07(br, 2H), 1.80–2.10(s+br, 5H), 2.80–3.40(br+t, 6H), 4.05(t, 2H), 4.90(s, 2H), 6.63(s, 1H), 6.71(s, 1H), 6.87(m, 1H), 7.11(m, 2H), 7.25(s, 1H), 7.31(m, 1H), 7.37–7.50(m, 4 H), 7.68(d, 1H), 7.82(d, 1H), 8.06(d, 1H)

FAB (M+H) 510, C$_{30}$H$_{31}$N$_5$OS(M)

EXAMPLE 12

Preparation of 1-[1-(furan-2-yl)methyl-1H-imidazol-5-yl]methyl-3-(4-methylpiperazin-1-yl)carbonyl-4-(naphthalen-1-yl)-1H-pyrrole(12)

640 mg(2 mmol) of the compound prepared in Preparation 4 was dissolved in 20 ml of dimethylformamide, 264 mg(6.6 mmol) of sodium hydride(60%) was added at 0° C., and the resulting mixture was stirred for 5 minutes. 450 mg(2.2 mmol) of the compound prepared in Preparation 7-2) was added thereto and the mixture was stirred for 3 hours at room temperature. The solvent was removed under reduced pressure and 30 ml of water was added thereto. The resulting mixture was extracte twice with 100 ml of ethylacetate the combined organic layer was dried over anhyrous sodium sulfate and concentrated. The concentrate was subjected to column chromatography(eluent: dichloromethane/methanol=95/5, v/v) to give 600 mg(Yield 63%) of the title compound.

$^1$H NMR(CDCl$_3$) δ 1.23(br, 2H), 1.90–2.03(s+br, 4H), 2.62(br, 2H), 3.03(br, 2H), 3.37(br, 2H), 4.92(s, 2H), 5.13(s, 2H), 6.22(d, 1H), 6.29(d, 1H), 7.12(s, 1H), 7.15(s, 1H), 7.31(m, 2H), 7.47(m, 3H), 7.67(s, 1H), 7.76(d, 1H), 7.83(d, 1H), 8.03(d, 1H)

FAB (M+H) 480, C$_{29}$H$_{29}$N$_5$O$_2$(M)

EXAMPLE 13

Preparation of 1-[1-(1-benzylpiperidin-4-yl)-1H-imidazol-5-yl]methyl-3-[N-(2-methoxyethyl)-N-methyl]carbamoyl-4-(naphthalen-1-yl)-1H-pyrrole (13)

The title compound was obtained with a yield of 70% according to the same procedure as Example 1 using the compound prepared in Preparation 2 and the compound prepared in Preparation 8-2) as starting materials.

$^1$H NMR(CDCl$_3$) δ 1.69(d, 2H), 1.92(m, 2H), 2.00(t, 2H), 2.17(br, 1H), 2.37(br, 2H), 2.70(br, 1H), 2.90–3.15(m, 7H), 3.30(s, 1H), 3.48(s, 2H), 3.72(m, 1H), 5.10(s, 2H), 6.71(d, 1H), 7.07(s, 1H), 7.13(s, 1H), 7.20–7.31(m, 6H), 7.32–7.42 (m, 3H), 7.64(d, 1H), 7.75(d, 1H), 7.83(d, 1H), 8.00(d, 1H)

FAB (M+H) 562, C$_{35}$H$_{39}$N$_5$O$_2$(M)

EXAMPLE 14

Preparation of 1-[1-(1-benzylpiperidin-4-yl)-1H-imidazol-5-yl]methyl-3-(morpholin-4-yl)carbonyl-4-naphthalen-1-yl)-1H-pyrrole(14)

The title compound was obtained with a yield of 70% according to the same procedure as Example 1 using the compound prepared in Preparation 3 and the compound prepared in Preparation 8-2) as starting materials.

$^1$H NMR(CDCl$_3$) δ 1.66(d, 2H), 1.89(m, 2H), 1.99(m, 2H), 2.28(br, 2H), 2.70–3.35(br, 8H), 3.47(s, 2H), 3.71(m, 1H), 5.12(s, 2H), 6.71(s, 1H), 7.14(d, 2H), 7.20–7.32(m, 6H), 7.33–7.50(m, 3H), 7.64(s, 1H), 7.77(d, 1H), 7.79(d, 1H), 7.93(d, 1H)

FAB (M+H) 560, C$_{35}$H$_{37}$N$_5$O$_2$(M)

Preparation 9

Preparation of 5-chloromethyl-2-methyl-1-(3,4-methylenedioxybenzyl)-1H-imidazole hydrochloride 9-1) Preparation of 5-hydroxymethyl-1-(3,4-methylenedioxybenzyl)-1H-imidazole The title compound was prepared by modifying the method described in the literature (see: *J. Med. Chem.*, 33, 1312–1329, 1990) from dihydroxyacetone dimer and piperonylamine. 1.37 g(10 mmol) of piperonylamine, 1.08 g(6 mmol) of dihydroxyacetone dimer and 1.15 g(11 mmol) of potassium thiocyanate were added to 10 ml of isopropyl alcohol, 2 ml of acetic acid was added thereto, and the resulting mixture was stirred for 48 hours at room temperature. The reaction mixture was filtered and the resulting solid was washed twice with 5 ml of isopropyl alcohol and twice with 5 ml of water. To the solid was added 12.5 ml of 10% aqueous nitric acid solution dropwise thereto at 0° C. To the above solution was added 10 mg of sodium nitrite and the mixture was stirred for 1 hour at room temperature. After the aqueous solution was washed with 10 ml of ethylacetate, it was basified and to give 1.16 g(Yield 50%) of the title compound as solid.

$^1$H NMR(DMSO) δ 4.34(d, 2H), 5.10(s, 2H), 5.14(t, 1H), 5.99(s, 2H), 6.70(d, 1H), 6.79(s, 2H), 6.88(d, 1H), 7.65(s, 1H)

FAB 233 (M+1), C$_{12}$H$_{12}$N$_2$O$_3$(M)

9-2) Preparation of 5-(t-butyldimethylsilyloxymethyl)-1-(3,4-methylenedioxybenzyl)-1H-imidazole 1.40 g(5.65 mmol) of the compound prepared in Preparation 9-1) was dissolved in 20 ml of dimethylformamide and 1.63 g(5.94 mmol) of t-butyldimethylsilylchloride was added dropwise thereto. After 3 hours, the solvent was removed under reduced pressure and the residue was dissolved in 20 ml of ethylacetate. The organic layer was washed with 20 ml of saturated aqueous sodium bicarbonate solution, dried over anhydrous magnesium sulfate and concentrated. The residue was subjected to column chromatography(eluent: dichloromethane/methanol=95/5, v/v) to give 1.16 g(3.35 mmol, Yield 59%) of the title compound.

$^1$H NMR(CDCl$_3$) δ 0.01(s, 6H), 0.86(s, 9H), 4.53(s, 2H), 5.08(s, 2H), 5.94(s, 2H), 6.59(s, 1H), 6.61(d, 1H), 6.74(d, 1H), 6.92(d, 1H), 7.42(s, 1H)

FAB 347 (M+1), C$_{18}$H$_{26}$N$_2$O$_3$Si(M)

9-3) Preparation of 5-(t-butyldimethylsilyloxymethyl)-2-methyl-1-(3,4-methylenedioxybenzyl)-1H-imidazole 1.14 g(3.3 mmol) of the compound prepared in Preparation 9-2) was dissolved in 20 ml of tetrahydrofuran and 1.71 ml(2.5 M solution) of n-butyllithium was added slowly over 30 minutes at −78° C. 457 mg(3.6 mmol) of dimethylsulfate was added and the resulting mixture was stirred for 1 hour. After reaction was completed, the solvent was removed, 15 ml of ethylacetate and 10 ml of saturated aqueous sodium bicarbonate solution were added, and then the organic layer was separated. The organic layer was dried over anhydrous magnesium sulfate and concentrated. The residue was subjected to column chromatography(eluent: dichloromethane/methanol=95/5, v/v) to give 448 mg (1.24 mmol, Yield 38%) of the title compound.

$^1$H NMR(CDCl$_3$) δ 0.00(s, 6H), 0.80(s, 9H), 2.23(s, 3H), 4.18(s, 2H), 5.02(s, 2H), 5.85(s, 2H), 6.42(m, 2H), 6.67(d, 1H), 6.78(s, 1H)

FAB 361 (M+H), C$_{19}$H$_{28}$N$_2$O$_3$Si(M)

9-4) Preparation of 5-(hydroxymethyl)-2-methyl-1-(3,4-methylenedioxybenzyl)-1H-imidazole 448 mg(1.24 mmol) of the compound prepared in Preparation 9-3) was dissolved in 10 ml of tetrahydrofuran, 0.96 ml(2.5 M solution) of tetrabutylammonium fluoride was added thereto, and the resulting mixture was stirred for 1 hour. After reaction was completed, the reaction solution was concentrated by removing the solvent. The residue was subjected to column chromatography(eluent: dichloromethane/methanol=95/5, v/v) to give 190 mg(0.77 mmol, Yield 62%) of the title compound.

$^1$H NMR(CDCl$_3$+CH$_3$OD) δ 2.17(s, 3H), 3.72(br, 1H), 4.36(d, 2H), 5.02(s, 2H), 5.85(s, 2H), 5.36(m, 2H), 6.65(d, 1H), 6.72(s, 1H)

FAB 247 (M+H), C$_{13}$H$_{14}$N$_2$O$_3$ (M)

9-5) Preparation of 5-chloromethyl-2-methyl-1-(3,4-methylenedioxybenzyl)-1H-imidazole hydrochloride 190 mg(0.77 mmol) of the compound prepared in Preparation 9-4) was dissolved in 3 ml of chloroform and 181 mg(1.54 mmol) of thionyl chloride was added dropwise at 0° C. After the reaction solution was stirred for 2 hours, the solvent was removed under reduced pressure and then the remaining hydrochloride was removed to give the title compound with a yield of 95%. The product thus obtained was directly used in the next reaction without purification.

Preparation 10

Preparation of 5-chloromethyl-1-(3,4-methylenedioxybenyl)-1H-imidazole hydrochloride 1.5 g(Yield 92%) of the title compound was obtained by reacting the compound prepared in Preparation 9-1) according to the same procedure as Preparation 9-5) (see: PCT/KR98/00377).

Preparation 11

Preparation of 5-chloromethyl-4-methyl-1-(3,4-methylenedioxybenzyl)-1H-imidazole hydrochloride 11-1) Preparation of 5-(t-butyldiphenylsilyloxymethyl)-4-methylimidazole To 2.0 g(13.5 mmol) of 4-methyl-5-imidazolemethanol hydrochloride and 1.95 g(14.17 mmol) of potassium carbonate in 20 ml of dimethylformamide was added 3.88 g(14.17 mmol) of t-butyldiphenylsilylchloride was added dropwise thereto, and the resulting mixture was stirred for 3 hours. The solvent was removed under reduced pressure and the residue was dissolved in 20 ml of ethylacetate. The organic layer was washed with 20 ml of saturated aqueous sodium bicarbonate solution, dried over anhydrous magnesium sulfate and concentrated. The residue was subjected to column chromatography(eluent: dichloromethane/methanol=95/5, v/v) to give 1.22 g(3.44 mmol, Yield 26%) of the title compound.

$^1$H NMR(CDCl$_3$) δ 1.03(s, 9H), 2.02(s, 3H), 4.66(s, 2H), 7.34–7.47(m, 7H), 7.62–7.71(m, 4H)

FAB 351 (M+H), C$_{21}$H$_{26}$N$_2$OSi(M)

11-2) Preparation of 5-(t-butyldiphenylsilyloxymethyl)-4-methyl-1-(3,4-methylenedioxybenzyl)-1H-imidazole 610 mg(1.74 mmol) of the compound prepared in Preparation 11-1), 380 mg(1.58 mmol) of piperonyl bromide and 250 mg(1.81 mmol) of potassium carbonate were added to 7 ml of dimethylformamide and the resulting mixture was reacted under stirring for 2 hours. The solvent was removed under reduced pressure and the residue was subjected to column chromatography(eluent: dichloromethane/methanol=95/5, v/v) to give 260 mg (0.54 mmol, Yield 31%) of the title compound.

$^1$H NMR(CDCl$_3$) δ 1.04(s, 9H), 1.96(s, 3H), 4.48(s, 2H), 5.13(s, 2H), 5.89(s, 2H), 6.57(m, 2H), 6.72(d, 1H), 7.30–7.43(m, 7H), 7.61–7.70(m, 4H)

FAB 485 (M+H), C$_{29}$H$_{32}$N$_2$O$_3$Si(M)

11-3) Preparation of 5-(hydroxymethyl)-4-methyl-1-(3,4-methylenedioxybenzyl)-1H-imidazole 120 mg(0.25 mmol) of the compound prepared in Preparation 11-2) was dissolved in 5 ml of tetrahydrofuran, 0.2 ml(2.5 M solution) of tetrabutylammonium fluoride was added thereto, and the resulting mixture was stirred for 1 hour. After reaction was completed, the reaction mixture was concentrated by removing the solvent. To the residue were added 10 ml of ethylacetate and 5 ml of saturated aqueous sodium bicarbonate solution. The organic layer was dried over anhydrous magnesium sulfate and concentrated. The residue was subjected to column chromatography(eluent: dichloromethane/methanol=95/5, v/v) to give 34 mg(0.14 mmol, Yield 28%) of the title compound.

$^1$H NMR(CDCl$_3$) δ 2.13(s, 3H), 2.45(br, 1H), 4.71(s, 2H), 5.05(s, 2H), 5.93(s, 2H), 6.58(m, 1H), 6.62(m, 1H), 6.74(d, 1H), 7.33(s, 1H)

FAB 247 (M+H), C$_{13}$H$_{14}$N$_2$O$_3$ (M)

11-4) Preparation of 5-chloromethyl-4-methyl-1-(3,4-methylenedioxybenzyl)-1H-imidazole hydrochloride 19 mg(0.08 mmol) of the compound prepared in Preparation 11-3) was dissolved in 3 ml of chloroform and 18 mg(0.15 mmol) of thionyl chloride was added dropwise at 0° C. After the resulting mixture was stirred for 2 hours, the solvent was removed under reduced pressure and the remaining hydrochloride was removed to give the title compound with a yield of 90%. The product thus obtained was directly used in the next reaction without purification.

Preparation 12

Preparation of 5-chloromethyl-4-iodo-1-(3,4-methylenedioxybenzyl)-1H-imidazole hydrochloride 12-1) Preparation of 4,5-diiodoimidazole The title compound was prepared according to the method described in the literature (see: Naidu, M. S. R.; Bensusan, H. B., *J. Org. Chem.*, 33, 1307(1968)).

$^1$H NMR(DMSO-d6) δ 7.77(s, 1H)

12-2) Preparation of 4,5-diiodo-1-(3,4-methylenedioxybenzyl)-1H-imidazole 1.55 g(Yield 60%) of the title compound was obtained by reacting the compound prepared in Preparation 12-1) with piperonyl bromide according to the same procedure as Preparation 11-2).

$^1$H NMR(DMSO-d6) δ 5.14(s, 2H), 6.00(s, 2H), 6.66(d, 1H), 6.80(s, 1H), 6.89(d, 1H), 8.04(s, 1H)

FAB 455 (M+H), C$_{11}$H$_8$I$_2$N$_2$O$_2$(M)

12-3) Preparation of 4-iodo-1-(3,4-methylenedioxybenzyl)-5-imidazole-carboxyaldehyde To 1.45 g(3.20 mmol) of the compound prepared in Preparation 12-2) was dissolved in 10 ml of tetrahydrofuran was added 3.53 ml(1.0 M tetrahydrofuran solution) of ethylmagnesium bromide. To this reaction solution was added 0.49 ml(6.40 mmol) of dimethylformamide under stirring and the resulting mixture was stirred for 3 hours. The solvent was removed under reduced pressure and the residue was dissolved in 10 ml of methylene chloride and the organic layer was washed with saturated ammonium chloride solution. The organic layer was separated, dried over anhydrous magnesium sulfate and concentrated by removing the solvent. The residue was subjected to column chromatography(eluent: dichloromethane/methanol=95/5, v/v) to give 800 mg(2.23 mmol, Yield 70%) of the title compound.

$^1$H NMR(CDCl$_3$) δ 5.38(s, 2H), 6.95(s, 2H), 6.68–6.90 (m, 3H), 7.56(s, 1H), 9.61(s, 1H)

FAB 357 (M+H), C$_{12}$H$_9$IN$_2$O$_3$(M)

12-4) Preparation of 5-hydroxymethyl-4-iodo-1-(3,4-methylenedioxybenzyl)-1H-imidazole 360 mg(1 mmol) of the compound prepared in Preparation 12-3) was dissolved in 10 ml of methanol, 45 mg(1.2 mmol) of sodium borohydride was added, and the resulting mixture was stirred for 1 hour. After reaction was completed, the solvent was removed. The residue was dissolved in 10 ml of methylene chloride, which was then washed with saturated ammonium chloride solution. The organic layer was separated, dried over anhydrous magnesium sulfate and concentrated. Teh residue thus obtained was subjected to column chromatography (eluent: dichloromethane/methanol=95/5, v/v) to give 200 mg(0.56 mmol, Yield 58%) of the title compound.

$^1$H NMR(CH$_3$OD) δ 4.47(s, 2H), 5.22(s, 2H), 5.39(s, 2H), 6.70–6.81(m, 3H), 7.69(s, 1H)

FAB 359 (M+H), C$_{12}$H$_{11}$I$_2$N$_2$O$_3$(M)

12-5) Preparation of 5-chloromethyl-4-iodo-1-(3,4-methylenedioxybenzyl)-1H-imidazole hydrochloride 69 mg(0.19 mmol) of the compound prepared in Preparation 12-4) was dissolved in 3 ml of chloroform and 45 mg(0.38 mmol) of thionyl chloride was added dropwise at 0° C. After the solutoin was stirred for 2 hours, the solvent was removed under reduced pressure and the remaining hydrochloride was removed to give the title compound with a yield of 91%. The product thus obtained was directly used in the next reaction without purification.

Preparation 13

Preparation of 5-chloromethyl-1-(3,4-methylenedioxybenzyl)-4-nitro-1H-imidazole 13-1) Preparation of 1-(3,4-methylenedioxybenzyl)-4-nitro-1H-imidazole 3.39 g(30 mmol) of 4-nitroimidazole, 6.45 g(30 mmol) of piperonyl bromide and 8.28 g(60 mmol) of potassium carbonate were added to 100 ml of dimethylformamide and the resulting mixture was reacted for 6 hours. The reaction solution was concentrated by removing the solvent. The residue was dissolved in 100 ml of ethylacetate and the combined organic layer was washed twice with 100 ml of water. The organic layer was separated, concentrated and then subjected to column chromatography (eluent: hexane/ethylacetate=2/1, v/v) to give 6.17 g(1.52 mmol, Yield 83%) of the title compound.

$^1$H NMR(CDCl$_3$) δ 5.05(s, 2H), 6.00(s, 2H), 6.68(s, 1H), 6.74(d, 1H), 6.82(d, 1H), 7.46(s, 1H), 7.70(s, 1H)

FAB 248 (M+H), C$_{11}$H$_9$N$_3$O$_4$(M)

13-2) Preparation of t-butyl-1-chloro-1-[1-(3,4-methylenedioxybenzyl)-4-nitro-1H-imidazole-5-yl]acetate 3.84 g(34.2 mmol) of potassium-t-butoxide was dissolved in 20 ml of tetrahydrofuran and the mixture was cooled to −78° C. 1.69 g(6.84 mmol) of the compound prepared in Preparation 13-1) and 1.27g(6.86 mmol) of t-butyl dichloroacetate in 10 ml of dimethylform amide was added dropwise to the former solution over 30 minutes. After stirring for 5 minutes, the reaction solution was poured into diluted aqueous hydrochloric acid solution and the organic solvent was removed under reduced pressure. The residue was extracted with dichloromethane, the organic layer was dried over anhydrous magnesium sulfate and concentrated. The residue was subjected to column chromatography(eluent: dichloromethane/methanol=98/2, v/v) to give 600 mg (1.52 mmol, Yield 22%) of the title compound.

$^1$H NMR(CDCl$_3$) δ 1.45(s, 9H), 5.15(dd, 2H), 5.99(s, 2H), 6.54(s, 1H), 6.71(s, 1H), 6.76(d, 1H), 6.81(d, 1H), 7.24(s, 1H)

FAB 396 (M+H), C$_{17}$H$_{18}$ClN$_3$O$_6$(M)

13-3) Preparation of 5-chloromethyl-1-(3,4-methylenedioxybenzyl)-4-nitro-1H-imidazole 360 mg(0.910 mmol) of the compound prepared in Preparation 13-2) was dissolved in 5 ml of acetic acid and the resulting mixture was refluxed for 30 minutes. The reaction mixture was poured into 20 g of ice and extracted with dichloromethane(20 ml×3). The organic layer was dried over anhydrous potassium carbonate and concentrated under reduced pressure. The residue was subjected to column chromatography(eluent: dichloromethane/methanol=99/1, v/v) to give 150 mg(0.507 mmol, Yield 56%) of the title compound.

$^1$H NMR(CDCl$_3$) δ 4.94(s, 2H), 5.17(s, 2H), 5.99(s, 2H), 6.65(s, 1H), 6.72(d, 1H), 6.81(d, 1H), 7.43(s, 1H)

FAB 296 (M+H), C$_{12}$H$_{10}$ClN$_3$O$_4$(M)

Preparation 14

Preparation of 5-chloromethyl-1-(2-methoxyphenethyl)-2-methyl-1H-imidazole hydrochloride 14-1) Preparation of 5-(t-butyldimethylsilyloxymethyl)-1-(2-methoxyphenethyl)-1H-imidazole 248 mg(1.09 mmol) of 5-hydroxymethyl-1-(2-methoxyphenethyl)-1H-imidazole prepared according to the same procedure as Preparation 9-1) was dissolved in 3 ml of dimethylformamide and 170 mg(1.13 mmol) of t-butyldimethylsilylchloride was added thereto. After stirring for 1 hour, the solvent was removed under reduced pressure and the residue was subjected to column chromatography(eluent: methylene dichloride/methanol=95/5, v/v) to give 248 mg(0.72 mmol, Yield 66%) of the title compound.

$^1$H NMR(CDCl$_3$) δ 0.03(s, 6H), 0.86(s, 9H), 3.04(t, 2H), 3.80(s, 3H), 4.17(t, 2H), 4.54(s, 2H), 6.80–6.95(m, 4H), 7.20–7.35(m, 2H)

FAB 347 (M+H), C$_{19}$H$_{30}$N$_2$O$_2$Si(M)

14-2) Preparation of 5-(t-butyldimethylsilyloxymethyl)-1-(2-methoxyphenethyl)-2-methyl-1H-imidazole 80 mg(Yield 50%) of the title compound was obtained by reacting the compound prepared in Preparation 14-1) according to the same procedure as Preparation 9-3).

¹H NMR(CDCl₃) δ (0.04(s, 6H), 0.86(s, 9H), 2.19(s, 3H), 2.97(t, 2H), 3.78(s, 3H), 4.05(t, 2H), 4.49(s, 2H), 6.72–7.00 (m, 4H), 7.15–7.31(m, 1H)

FAB 361 (M+H), C₂₀H₃₂N₂O₂Si(M)

14-3) Preparation of 5-(hydroxymethyl)-1-(2-methoxyphenethyl)-2-methyl-1H-imidazole 30 mg(Yield 56%) of the title compound was obtained by reacting the compound prepared in Preparation 14-2) according to the same procedure as Preparation 9-4).

¹H NMR(CDCl₃) δ 2.19(s, 3H), 2.99(t, 2H), 3.65(br, 1H), 3.82(s, 3H), 4.09(t, 2H), 4.48(s, 2H), 6.70(s, 1H), 6.83(m, 2H), 6.97(d, 1H), 7.21(m, 1H)

FAB (247 (M+H), C₁₄H₁₈N₂O₂ (M)

14-4) Preparation of 5-chloromethyl-1-(2-methoxyphenethyl)-2-methyl-1H-imidazole hydrochloride The title compound was obtained with a yield of 95% according to the same procedure as Preparation 9-5). The product thus obtained was directly used in the next reaction without purification.

Preparation 15

Preparation of 1-(3-benzyloxypropyl)-5-chloromethyl-4-methyl-1H-imidazole 15-1) Preparation of 3-benzyloxypropanol 38.05 g(0.50 mol) of propandiol was dissolved in 400 ml of dimethylformamide and cooled to 0° C. 20.0 g(0.5 mol) of 60% sodium hydride dispersed in mineral oil was added slowly. After the mixture was stirred for 10 minutes, 51.31 g(0.30 mol) of benzylbromide dissolved in 100 ml of dimethylformamide was added slowly. After stirring for one hour at room temperature, dimethylformamide was removed under reduced pressure, 500 ml of ethylacetate was added, and the organic layer was washed with saturated sodium chloride solution (200 ml×3). The organic layer was dried over anhydrous magnesium sulfate and concentrated. The residue was subjected to column chromatography to give 33.80 g(0.203 mol, Yield 68%) of the title compound.

¹H NMR(CDCl₃) δ 1.83–1.92(m, 2H), 2.31(brs, 1H), 3.65(t, 2H), 3.77(t, 2H), 4.51(s, 2H), 7.25–7.37(m, 5H)

FAB 167 (M+H), C₁₀H₁₄O₂(M)

15-2) Preparation of 3-benzyloxypropyl-methanesulfonate 33.80 g(0.203 mol) of the compound prepared in Preparation 15-1) was dissolved in 500 ml of dichloromethane and cooled to 0° C. 24.46 g (0.214 mol) of methanesulfonylchloride and 21.60 g(0.214 mol) of triethylamine were added. The reaction mixture was stirred for one hour at room temperature and then washed with water (300 ml×3). The organic layer was dried over anhydrous magnesium sulfate and concentrated to give 49.40 g(0.202 mol, Yield 99.5%) of the title compound. The product thus obtained was directly used in the next reaction without purification.

¹H NMR(CDCl₃) δ 2.04(m, 2H), 2.95(s, 3H), 3.57(t, 2H), 4.36(t, 2H), 4.51(s, 2H), 7.25–7.37(m, 5H)

FAB 245 (M+H), C₁₁H₁₆O₄S(M)

15-3) Preparation of 5-(t-butyldimethylsilyloxymethyl)-4-methylimidazole 13.0 g(87.5 mmol) of 4-methyl-5-imidazolemethanol hydrochloride, 13.5 g(89.6 mmol) of t-butylchlorodimethylsilane and 14.5 g(105 mmol) of potassium carbonate were added to 200 ml of dimethylformamide and the resulting mixture was stirred for 3 days. After dimethylformamide was removed under reduced pressure, 500 ml of ethylacetate was added to the residue which was then washed with aqueous sodium chloride solution (200 ml×3). The organic layer was dried over anhydrous magnesium sulfate and concentrated to give 5.4 g(23.9 mmol, Yield 27%) of the title compound.

¹H NMR(CDCl₃) δ 0.07(s, 6H), 0.89(s, 9H), 2.21(s, 3H), 4.65(s, 2H), 7.47(s, 1H)

15-4) Preparation of 1-(3-benzyloxypropyl)-5-(t-butyldimethylsilyloxymethyl)-4-methyl-1H-imidazole 3.10 g(13.7 mmol) of the compound prepared in Preparation 15-3) was dissolved in 20 ml of dimethylformamide and cooled to 0° C. 0.66 g (16.5 mmol) of 60% sodium hydride dispersed in mineral oil was added slowly. After the mixture was stirred for 5 minutes, 3.35 g(13.7 mmol) of 3-benzyloxypropyl methanesulfonate prepared in Preparation 15-2) was added slowly. After stirring for 2 hours at room temperature, dimethylformamide was removed under reduced pressure, 200 ml of ethylacetate was added, and the organic layer was washed with saturated sodium chloride solution (100 ml×3). The organic layer was dried over anhyrous magnesium sulfate and concentrated. The residue was subjected to column chromatography (eluent: dichloromethane/methanol=95/5, v/v) to give 2.00 g(5.34 mmol, Yield 39%) of the title compound and 1.34 g(3.58 mmol, Yield 26%) of 1-(3-benzyloxypropyl)-3-(t-butyldimethylsilyloxymethyl)-2-methyl-1H-imidazole, respectively.

1-(3-benzyloxypropyl)-5-(t-butyldimethylsilyloxymethyl)-4-methyl-1H-imidazole

¹H NMR(CDCl₃) δ 0.03(s, 6H), 0.88(s, 9H), 2.05(m, 2H), 2.19(s, 3H), 3.43(t, 2H), 4.06(t, 2H), 4.48(s, 2H), 4.58(s, 2H), 7.28–7.34(m, 6H)

FAB 375 (M+H), C₂₁H₃₄N₂O₂Si(M)

1-(3-benzyloxypropyl)-3-(t-butyldimethylsilyloxymethyl)-2-methyl-1H-imidazole

¹H NMR(CDCl₃) δ 0.08(s, 6H), 0.90(s, 9H), 1.96(m, 2H), 2.20(s, 3H), 3.42(t, 2H), 3.93(t, 2H), 4.48(s, 2H), 4.63(s, 2H), 7.28–7.35(m, 6H)

15-5) Preparation of 1-(3-benzyloxypropyl)-5-(hydroxymethyl)-4-methyl-1H-imidazole To 1.20 g(3.20 mmol) of the compound prepared in Preparation 15-4) in 10 ml of tetrahydrofuran was added 6.4 ml(1 M tetrahydrofuran solution) of tetrabutylammonium fluoride. After the resulting mixture was stirred for 3 hours at room temperature, the solvent was removed under reduced pressure. 50 ml of water was added and the mixture was extracted with ethylacetate. The organic layer was dried over anhydrous magnesium sulfate and concentrated. The residue was subjected to column chromatography(eluent: dichloromethane/methanol=95/5, v/v) to give 650 mg(2.50 mmol, Yield 78%) of the title compound.

¹H NMR(CDCl₃) δ 2.02(m, 2H), 2.07(s, 3H), 3.41(t, 2H), 4.04(t, 2H), 4.45(s, 2H), 4.51(s, 2H), 7.29–7.33(m, 6H)

FAB 261 (M+H), C₁₅H₂₀N₂O₂ (M)

15-6) Preparation of 1-(3-benzyloxypropyl)-5-chloromethyl-4-methyl-1H-imidazole 650 mg(2.50 mmol) of the compound prepared in Preparation 15-5) was dissolved in 10 ml of chloroform and cooled to 0° C. 450 mg(3.78 mmol) of thionyl chloride was added. After the mixture was stirred for 2 hours at room temperature, the organic solvent and the remaining thionyl chloride were removed under reduced pressure to give 780 mg(2.47 mmol, Yield 99%) of hte title compound. The product thus obtained was directly used in the next reaction without purification.

¹H NMR(CDCl₃) δ 2.24(m, 2H), 2.43(s, 3H), 3.52(t, 2H), 4.36(t, 2H), 4.47(s, 2H), 4.52(s, 2H), 7.25–7.43(m, 5H), 9.18(s, 1H)

Preparation 16

Preparation of 1-[3-(2-chlorobenzyloxy)propyl]-5-chloromethyl-4-methyl-1H-imidazole 16-1) Preparation of 3-(2-chlorobenzyloxy)propanol 3.7 g(49 mmol) of 1,3-propandiol was dissolved in 50 ml of dimethylformamide and cooled to 0° C. 2 g(50 mmol) of 60% sodium hydride dispersed in mineral oil was added slowly. After the mixture was stirred for 10 minutes, 10 g(49 mmol) of 2-chlorobenzyl-bromide dissolved in 10 ml of dimethyformamide was added slowly. After stirring for one hour at room temperature, dimethylformamide was removed under reduced pressure, 100 ml of ethylacetate was added to the residue and the organic layer was washed with saturated sodium chloride solution (100 ml×3). The organic layer was dried over anhydrous magnesium sulfate and concentrated. The residue was subjected to column chromatography (eluent: n-hexane/ethylacetate=4/1, v/v) to give 3.52 g(Yield 35.8%) of the title compound.

¹H NMR(CDCl₃) δ 1.91(m, 2H), 3.75(m, 2H), 3.81(t, 2H), 4.62(s, 2H), 7.20–7.29(m, 2H), 7.34(t, 1H), 7.43(t, 1H)

FAB 201 (M+H), C₁₀H₁₃ClO₂(M)

16-2) Preparation of 3-(2-chlorobenzyloxy)propyl-methanesulfonate 3.52 g(17.5 mmol) of the compound prepared in Preparation 16-1) was dissolved in 100 ml of dichloromethane and cooled to 0° C. 1.63 ml (21 mmol) of methanesulfonylchloride and 4.9 ml(35 mmol) of triethylamine were added. The reaction mixture was stirred for one hour at room temperature and then washed with water(100 ml×3). The organic layer was dried over anhydrous magnesium sulfate and concentrated to give 4.51 g(Yield 92.5%) of the title compound. The product thus obtained was used in the next reaction without purification.

¹H NMR(CDCl₃) δ 2.08(m, 2H), 2.98(s, 3H), 3.66(t, 2H), 4.38(t, 2H), 4.60(s, 2H), 7.20–7.29(m, 2H), 7.34(t, 1H), 7.43(t, 1H)

FAB 279 (M+H), C₁₁H₁₅ClO₄S(M)

16-3) Preparation of 5-(t-butyldimethylsilyloxymethyl)-1-[3-(2-chlorobenzyloxy)propyl]-4-methyl-1H-imidazole 3.0 g(13 mmol) of the compound prepared in Preparation 15-3) was dissolved in 50 ml of dimethylformamide and cooled to 0° C. 1.0 g (25 mmol) of 60% sodium hydride dispersed in mineral oil was added slowly. After the mixture was stirred for 5 minutes, 4.51 g(16.2 mmol) of the compound prepared in Preparation 16-2) was added slowly. After stirring for 2 hours at room temperature, dimethylformamide was removed under reduced pressure, 100 ml of ethylacetate was added, and the organic layer was washed with saturated sodium chloride solution (100 ml×3). The organic layer was dried over anhydrous magnesium sulfate and concentrated. The residue was subjected to column chromatography (eluent: dichloromethane/methanol=98/2, v/v) to give 1.9 g(4.6 mmol, Yield 35%) of the title compound and 1.5 g(3.7 mmol, Yield 28%) of 1-[3-(2-chlorobenzyloxy)propyl]-3-(t-butyldimethylsilyloxymethyl)-2-methyl-1H-imidazole, respectively.

¹H NMR(CDCl₃) δ 0.03(s, 6H), 0.86(s, 9H), 2.09(m, 2H), 2.18(s, 3H), 3.51(t, 2H), 4.08(t, 2H), 4.57(s, 2H), 4.59(s, 2H), 7.20–7.29(m, 2H), 7.32(s, 1H), 7.34(t, 1H), 7.43(t, 1H)

FAB 410 (M+H), C₂₁H₃₃ClN₂O₂Si(M)

16-4) Preparation of 1-[3-(2-chlorobenzyloxy)propyl]-5-(hydroxymethyl)-4-methyl-1H-imidazole To 1.9 g(4.6 mmol) of the compound prepared in Preparation 16-3) in 100 ml of tetrahydrofuran was added 5.0 ml(1 M tetrahydrofuran solution) of tetrabutylammonium fluoride. After the resulting mixture was stirred for 3 hours at room temperature, the solvent was removed under reduced pressure. 100 ml of water was added and the crude product was extracted with ethylacetate (100 ml×3). The organic layer was dried over anhydrous magnesium sulfate and concentrated. The residue was subjected to column chromatography(eluent: dichloromethane/methanol=95/5, v/v) to give 640 mg(2.2 mmol, Yield 47%) of the title compound.

¹H NMR(CDCl₃) δ 2.00(s, 3H), 2.02(m, 2H), 3.42(t, 2H), 4.03(t, 2H), 4.46(s, 2H), 4.48(s, 2H), 7.10–7.20(m, 2H), 7.19(s, 1H), 7.25(t, 1H), 7.35(t, 1H)

FAB 295 (M+H), C₁₅H₁₉ClN₂O₂ (M)

16-5) Preparation of 1-[3-(2-chlorobenzyloxy)propyl]-5-chloromethyl-4-methyl-1H-imidazole 640 mg(2.2 mmol) of the compound prepared in Preparation 16-4) was dissolved in 40 ml of chloroform and cooled to 0° C. 0.32 ml(4.3 mmol) of thionyl chloride was added. After the mixture was stirred for 2 hours at room temperature, the organic solvent and the remaining thionyl chloride were removed under reduced pressure to give 740 mg(2.1 mmol, Yield 98%) of the title compound. The product thus obtained was used in the next reaction without purification.

¹H NMR(CDCl₃) δ 2.27(m, 2H), 2.44(s, 3H), 3.60(t, 2H), 4.38(t, 2H), 4.55(s, 2H), 4.58(s, 2H), 7.24–7.32(m, 2H), 7.37(m, 2H), 9.04(s, 1H)

Preparation 17

Preparation of 5-chloromethyl-1-[3-ethoxypropyl]-4-methyl-1H-imidazole 17-1) Preparation of 3-ethoxypropyl-1-methylsulfonate 950 mg(9.1 mmol) of 3-ethoxypropanol was dissolved in 100 ml of dichloromethane and cooled to 0° C. 0.86 ml(11 mmol) of methanesulfonyl-chloride was added and subsequently 1.9 ml(14 mmol) of triethylamine was added thereto. The reaction mixture was stirred for one hour at room temperature and then washed with water(100 ml×3). The organic layer was dried over anhydrous magnesium sulfate and concentrated to give 1.3 g(Yield 78%) of the title compound. The product thus obtained was used in the next reaction without purification.

¹H NMR(CDCl₃) δ 1.14(t, 3H), 1.77(m, 2H), 2.97(s, 3H), 3.44(q, 2H), 3.55(t, 2H), 4.38(t, 2H)

FAB 183 (M+H), C₆H₁₄O₄S(M)

17-2) Preparation of 5-(t-butyldimethylsilyloxymethyl)-1-[3-ethoxypropyl]-4-methyl-1H-imidazole 1.24 g (5.5 mmol) of the compound prepared in Preparation 15-3) was dissolved in 50 ml of dimethylformamide and cooled to 0° C. 420 mg (10.5 mmol) of 60% sodium hydride dispersed in mineral oil was added slowly. After the mixture was stirred for 5 minutes, 1.3 g(7.1 mmol) of the compound prepared in Preparation 17-1) was added slowly. After stirring for 2 hours at room temperature, dimethylformamide was removed under reduced pressure, 100 ml of ethylacetate was added, and the organic layer was washed with saturated sodium chloride solution(100 ml×3). The organic layer was dried over anhydrous magnesium sulfate and concentrated. The residue was subjected to column chromatography(eluent: dichloromethane/methanol=98/2, v/v) to give 350 mg(1.1 mmol, Yield 20%) of the title compound and 320 mg(1.0 mmol, Yield 18%) of 1-[3-ethoxypropyl]-3-(t-butyl- dimethylsilyloxymethyl)-2-methyl-1H-imidazole $^1$H NMR(CDCl$_3$) δ 0.04(s, 6H), 0.87(s, 9H), 1.19(t, 3H), 2.01(m, 2H), 2.19(s, 3H), 3.35(t, 2H), 3.44(q, 2H), 4.04(t, 2H), 4.59(s, 2H), 7.34(s, 1H)

FAB 313 (M+H), C$_{16}$H$_{32}$N$_2$O$_2$Si(M)

17-3) Preparation of 1-[3-ethoxypropyl]-5-hydroxymethyl-4-methyl-1H-imidazole

To 350 mg(1.1 mmol) of the compound prepared in Preparation 17-2) was dissolved in 60 ml of tetrahydrofuran was added 1.2 ml(1M tetrahydrofuran solution) of tetrabutylammonium fluoride. After the resulting mixture was stirred for 3 hours at room temperature, the solvent was removed under reduced pressure. 100 ml of saturated sodium bicarbonate solution was added and the crude product was extracted with ethylacetate(100 ml×3). The organic layer was dried over anhydrous magnesium sulfate and concentrated. The residue was subjected to column chromatography(eluent: dichloromethane/methanol=98/2, v/v) to give 110 mg(0.55 mmol, Yield 50%) of the title compound.

$^1$H NMR(CDCl$_3$) δ 1.18(t, 3H), 2.03(m, 2H), 2.19(s, 3H), 3.36(t, 2H), 3.44(q, 2H), 4.07(t, 2H), 4.57(s, 2H), 7.39(s, 1H)

FAB 199 (M+H), C$_{10}$H$_{18}$N$_2$O$_2$ (M)

17-4) Preparation of 5-chloromethyl-1-[3-ethoxypropyl]-4-methyl-1H-imidazole

To 110 mg(0.55 mmol) of the compound prepared in Preparation 17-3) in 40 ml of chloroform was added 0.1 ml(1.4 mmol) of thionyl chloride at room temperature. After the mixture was stirred for 2 hours at room temperature, the organic solvent and the remaining thionyl chloride were removed under reduced pressure to give 130 mg(0.53 mmol, Yield 96%) of the title compound. The product thus obtained was used in the next reaction without purification.

$^1$H NMR(CDCl$_3$) δ 1.57(t, 3H), 2.20(brm, 2H), 2.45(s, 3H), 3.37–3.56(t&q, 4H), 4.38(brt, 2H), 4.61(s, 2H), 9.36(s, 1H)

Preparation 18

Preparation of 3-methoxycarbonyl-2-methyl-4-(naphthalen-1-yl)-1H-pyrrole 0.69 g(5.9 mmol) of methyl 3-oxobutanoate and 1.08 g(5.9 mmol) of 1-[(E)-2-nitroethenyl]naphthalene were added to 2.37 ml of 0.5M sodium methoxide in methanol, and the resulting mixture was stirred for 2 hours at 0° C. The reaction solution was diluted with 10 ml of cold methanol, through which ammonia gas was passed. Reaction was carried out for 12 hours at 0° C. under stirring. After reaction was completed, the solvent was removed under reduced pressure and the residue was subjected to column chromatography(eluent: ethylacetate/hexane=90/10, v/v; ethylacetate/hexane=70/30, v/v) to give 936 mg(3.53 mmol, Yield 59%) of the title compound.

$^1$H NMR(CDCl$_3$) δ 2.49(s, 3H), 3.36(s, 3H), 6.44(d, 1H), 7.28–7.57(m, 4H), 7.75–7.95(m, 3H), 8.66(s, 1H)

Preparation 19

Preparation of 2-ethylthio-3-ethoxycarbonyl-4-(naphthalen-1-yl)-1H-pyrrole 19-1) Preparation of ethyl[(4-methylphenyl)sulfonyl]methylcarbonochloride imidothioic acid 6.22 g(100 mmol) of ethanethiol and 200 mg of triethylamine were dissolved in 30 ml of carbon tetrachloride and cooled to 0° C. To the above mixture was added 13.35 g(100 mmol) of sulfuryl chloride slowly. The reaction mixture was stirred for 30 minutes and the solvent was removed. The resulting residue was dissolved in 15 ml of tetrahydrofuran. 23.4 g(120 mmol) of TosMIC in 15 ml of tetrahydrofuran was added slowly to the above mixture. Reaction was carried out for 2 hours under stirring. The solvent was removed to give 28 g (Yield 96%) of the title compound.

FAB(*M+H*) 292

19-2) Preparation of 2-ethylthio-3-ethoxycarbonyl-4-(naphthalen-1-yl)-1H-pyrrole 370 mg(1.27 mmol) of the compound prepared in Preparation 19-1) and 288 mg(0.85 mmol) of the compound prepared in Preparation 1-1) were dissolved in 2 ml of tetrahydrofuran. To the above mixture were added 170 mg(1.7 mmol) of aluminum hydroxide and 190 mg(3.4 mmol) of potassium hydroxide, and then reaction was carried out for 4 hours under stirring. The solvent was removed and to the resulting residue were added 10 ml of ethylacetate and 10 ml of saturated aqueous sodium bicarbonate solution. The organic layer was separated and dried over anhydrous magnesium sulfate. The solvent was removed under reduced pressure and the residue was subjected to column chromatography(eluent: hexane/ethylacetate=70/30, v/v) to give 69 g(0.21 mmol, Yield 25%) of the title compound.

$^1$H NMR(CDCl$_3$) δ 1.07(t, 3H), 1.23(t, 3H), 3.00(q, 2H), 4.09(q, 2H), 7.10–7.45(m, 5H), 7.60–8.05(m, 4H)

FAB 326 (M+H), C$_{19}$H$_{19}$NO$_2$S(M)

Preparation 20

Preparation of 1-hydroxypiperazine dihydrochloride

The title compound was obtained by reacting 1-formylpiperazine according to the method described in the literature(see: *J. Heterocyclic Chem.*, 1989, 26, 393).

EXAMPLE 15

Preparation of 1-[2-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(15)

320 mg(1 mmol) of the compound prepared in Preparation 4 was dissolved in 5 ml of dimethylformamide and cooled to 0° C. 80 mg(2 mmol) of 60% sodium hydride dispersed in mineral oil was added thereto. After 10 minutes, 300 mg(1.1 mmol) of the compound prepared in Preparation 9-5) was added and the mixture was stirred for 2 hours at room temperature. The solvent was removed under reduced pressure, and the residue was dissolved in 20 ml of ethylacetate and the organic layer was washed with aqueous sodium chloride solution. The organic layer was concentrated and subjected to column chromatography (eluent: dichloromethane/methanol=93/7, v/v) to give 411 mg(0.75 mmol, Yield 75%) of the title compound.

$^1$H NMR(CDCl$_3$) δ 1.07(br, 2H), 1.70–2.10(br+s, 5H), 2.33(s, 3H), 2.88(br, 2H), 3.30(br, 1H), 4.88(s, 2H), 4.93(s, 2H), 5.88(s, 2H), 6.31(s, 1H), 6.33(d, 1H) 6.65(d, 1H), 6.69(d, 1H), 7.04(d, 1H), 7.10(s, 1H), 7.25(s, 1H), 7.29(d, 1H), 7.38–7.50(m, 3H), 7.74(d, 1H), 7.82(d, 1H), 7.97(d, 1H)

FAB 548 (M+H). C$_{33}$H$_{33}$N$_5$O$_3$(M)

EXAMPLE 16

Preparation of 1-[4-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(16)

320 mg(1 mmol) of the compound prepared in Preparation 4 and 300 mg (1.1 mmol) of the compound prepared in Preparation 11 were reacted according to the same procedure as Example 15 to give 270 mg (0.5 mmol, Yield 50%) of the title compound.

$^1$H NMR(CDCl$_3$) δ 1.11(br, 1H), 1.70–1.90(br, 4H), 1.89 (s, 3H), 2.34(s, 3H), 2.97(br, 2H), 3.31(br, 1H), 4.87(s, 2H), 4.94(s, 2H), 5.89(s, 2H), 6.44(s, 1H), 6.51(d, 1H), 6.58(d, 1H), 6.72(d, 1H), 7.01(m, 1H), 7.31(d, 1H), 7.40–7.49(m, 3H), 7.51(s, 1H), 7.76(d, 1H), 7.84(d, 1H), 8.00(d, 1H)

FAB 548 (M+H). C$_{33}$H$_{33}$N$_5$O$_3$(M)

EXAMPLE 17

Preparation of 1-[2-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(17)

17-1) Preparation of 1-[1-(3,4-methylenedioxybenzyl)-1H-imidazol-5-ylmethyl]-3-(4-methylpiperazin-1-yl)carbonyl-4-(naphthalen-1-yl)-1H-pyrrole To 640 mg(2 mmol) of the compound prepared in Preparation 4 in 20 ml of dimethylformamide was added 264 mg(6.6 mmol) of 60% sodium hydride dispersed in mineral oil slowly, and the mixture was stirred for 10 minutes. To the above reaction mixture was added slowly 500 mg (2.2 mmol) of the compound prepared in Preparation 10 at 0° C., and then reaction was carried out for 3 hours. After the solvent was removed in vacuo, 30 ml of water and 100 ml of ethylacetate were added to the residue. The resulting mixture was stirred and the organic layer was collected and dried over anhydrous sodium sulfate. The organic solvent was removed under reduced pressure and the residue was subjected to column chromatography(eluent: dichloromethane/methanol=90/10, v/v) to give 730 mg(1.36 mmol, Yield 67%) of the title compound.

$^1$H NMR(CDCl$_3$) δ 1.09(br, 2H), 1.70–2.00(br+s, 5H), 2.90(br, 2H), 3.30(br, 2H), 4.89(s, 2H), 4.95(s, 2H), 5.89(s, 2H), 6.43(s, 1H), 6.51(d, 1H), 6.63(d, 1H), 6.71(d, 1H), 7.04(d, 1H), 7.20(s, 1H), 7.31(d, 1H), 7.30–7.44(m, 3H), 7.55(s, 1H), 7.78(d, 1H), 7.83(d, 1H), 8.01(d, 1H)

FAB 534 (M+H)

17-2) Preparation of 1-[2-azido-1-(3,4-methylenedioxybenzyl)-1H-imidazol-5-ylmethyl]-3-(4-methylpiperazin-1-yl)carbonyl-4-(naphthalen-1-yl)-1H-pyrrole 1.00 g(1.87 mmol) of the compound prepared in Example 17-1) was dissolved in 40 ml of tetrahydrofuran. The mixture was cooled to −78° C. under nitrogen atmosphere and 0.83 ml(2.5M hexane solution) of n-butyllithium was added slowly. After stirring for 10 minutes, 480 mg (2.43 mmol) of TosMIC dissolved in 10 ml of tetrahydrofuran was added and the reaction mixture was warmed to room temperature. 1 ml of water was added to quench the reaction and the organic solvent was removed under reduced pressure. To the residue was added 20 ml of water and the crude product was extracted with ethylacetate(20 ml×2). The organic layer was dried over anhydrous magnesium sulfate and solvent was removed under reduced pressure. The residue thus obtained was subjected to column chromatography(eluent: dichloromethane/methanol=98/2, v/v) to give 330 mg(0.574 mmol, Yield 31%) of the title compound.

$^1$H NMR (CDCl$_3$) δ 1.10 (brs, 2H), 1.82(brs, 2H), 1.87(s, 3H), 2.93(brs, 2H), 3.33(brs, 2H), 4.74(s, 2H), 4.89(s, 2H), 5.90(s, 2H), 6.48(s, 1H), 6.49(d, 1H), 6.65(s, 1H), 6.71(d, 1H), 7.04(s, 1H), 7.05(d, 1H), 7.32(d, 1H), 7.40–7.48(m, 3H), 7.77(d, 1H), 7.83(d, 1H), 7.99(d, 1H)

FAB 577 (M+H), C$_{32}$H$_{32}$N$_8$O$_3$(M)

17-3) Preparation of 1-[2-amino-1-(3,4-methylenedioxybenzyl)-1H-imidazol-5-ylmethyl]-3-(4-methylpiperazin-1-yl)carbonyl-4-(naphthalen-1-yl)-1H-pyrrole 32 mg(0.057 mmol) of the compound prepared in Example 17-2) was dissolved in 3 ml of methanol. 5 mg of 10% Pd/C was added and the resulting mixture was stirred for 30 minutes under hydrogen atmosphere. This solution was filtered through cellite and concentrated to give 28 mg(0.051 mmol, Yield 89%) of the title compound.

$^1$H NMR (CDCl$_3$+DMSO-d6) δ 1.04 (brs, 2H), 1.72(brs, 2H), 1.80(s, 3H), 2.92(brs, 2H), 3.23(brs, 2H), 4.51(brs, 2H), 4.74(s, 2H), 4.87(s, 2H), 5.80(s, 2H), 6.35(s, 1H), 6.40(d, 1H), 6.61(d, 1H), 6.66(s, 1H), 6.75(s, 1H), 7.01(s, 1H), 7.21(d, 1H), 7.30–7.48(m, 3H), 7.69(d, 1H), 7.75(d, 1H), 7.89(d, 1H)

FAB 549(M+H). C$_{32}$H$_{32}$N$_6$O$_3$(M)

EXAMPLES 18 AND 19

Preparation of 1-[1-(3,4-methylenedioxybenzyl)-2-methylthio-1H-imidazol-5-ylmethyl]-3-(4-methylpiperazin-1-yl)carbonyl-4-(naphthalen-1-yl)-1H-pyrrole(18) and 1-[1-(3,4-methylenedioxybenzyl)-1H-imidazol-5-ylmethyl]-3-(4-methylpiperazin-1-yl)carbonyl-2-methylthio-4-(naphthalen-1-yl)-1H-pyrrole(19)

5.05 g(9.46 mmol) of the compound prepared in Example 17-1) was dissolved in 100 ml of tetrahydrofuran. The mixture was cooled to −78° C. under nitrogen atmosphere and 4.2 ml(2.5M hexane solution) of n-butyllithium was added slowly. After stirring for 10 minutes, 1.34 g(14.2 mmol) of dimethyldisulfide dissolved in 10 ml of tetrahydrofuran was added and the reaction mixture was warmed to room temperature. 1 ml of water was added to quench the reaction and the organic solvent was removed under reduced pressure. To the residue was added 20 ml of water and the crude product was extracted with ethylacetate(20 ml×3). The organic layer was dried over anhydrous magnesium sulfate and the solvent was removed under reduced pressure. The residue thus obtained was subjected to column chromatography(eluent: dichloromethane/methanol=98/2, v/v) to give 2.05 g(3.54 mmol, Yield 37%) of 1-[1-(3,4-methylenedioxybenzyl)-2-methylthio-1H-imidazol-5-ylmethyl]-3-(4-methylpiperazin-1-yl)carbonyl-4-(naphthalen-1-yl)-1H-pyrrole and 210 mg(0.36 mmol, Yield 4%) of 1-[1-(3,4-methylenedioxybenzyl)-1H-imidazol-5-ylmethyl]-3-(4-methylpiperazin-1-yl)carbonyl-2-methylthio-4-(naphthalen-1-yl)-1H-pyrrole.

1-[1-(3,4-methylenedioxybenzyl)-2-methylthio-1H-imidazol-5-ylmethyl]-3-(4-methylpiperazin-1-yl)carbonyl-4-(naphthalen-1-yl)-1H-pyrrole(18)

$^1$H NMR(CDCl$_3$) δ 1.10(brs, 2H), 1.82(brs, 2H), 1.87(s, 3H), 2.62(s, 3H), 2.90(brs, 2H), 3.34(brs, 2H), 4.93(s, 4H), 5.90(s, 2H), 6.44(s, 1H), 6.46(d, 1H), 6.65(s, 1H), 6.70(d, 1H), 7.05(s, 1H), 7.22(s, 1H), 7.32(d, 1H), 7.40–7.53(m, 3H), 7.77(s, 1H), 7.82(d, 1H), 8.00(d, 1H)

FAB 580 (M+H). C$_{33}$H$_{33}$N$_5$O$_3$S(M)

1-[1-(3,4-methylenedioxybenzyl)-1H-imidazol-5-ylmethyl]-3-(4-methyl piperazin-1-yl) carbonyl-2-methylthio-4-(naphthalen-1-yl)-1H-pyrrole(19)

$^1$H NMR(CDCl$_3$) δ 0.61(brs, 1H), 1.46(brs, 1H), 1.74(brs, 1H), 1.88(s, 3H), 2.22(brs, 1H), 2.34(s, 3H), 2.86(brs, 1H), 2.94(brs, 1H), 3.28(brs, 1H), 3.59(brs, 1H), 5.01(d, 2H), 5.28(dd, 2H), 5.88(s, 2H), 6.44(s, 1H), 6.50(d, 1H), 6.70(d, 1H), 6.77(s, 1H), 7.15(s, 1H), 7.32(d, 1H), 7.38–7.48(m, 3H), 7.55(s, 1H), 7.76(d, 1H), 7.82(d, 1H), 7.99(d, 1)

FAB 580 (M+H). $C_{33}H_{33}N_5O_3S(M)$

EXAMPLE 20

Preparation of 1-[4-iodo-1-(3,4-methylenedioxybenzyl)-1H-imidazol-5-ylmethyl]-3,4-(3-methylpiperazin-1-yl)carbonyl-4-(naphthalen-1-yl)-1H-pyrrole(20)

The compound prepared in Preparation 4 and the compound prepared in Preparation 12-5) were reacted according to the same procedure as Example 15 to give 56 mg(Yield 65%) of the title compound.

$^1$H NMR(CDCl$_3$) δ 1.09(br, 2H), 1.75–2.00(br+s, 5H), 2.90(br, 2H), 3.33(br, 2H), 4.94(s, 2H), 4.97(s, 2H), 5.90(s, 2H), 6.41(s, 1H), 6.50(s, 1H), 6.66(d, 1H), 6.72(d, 1H), 7.07(s, 1H), 7.32(d, 1H), 7.40–7.50(m, 3H), 7.53(s, 1H), 7.76(d, 1H), 7.84(d, 1H), 8.02(d, 1H)

FAB 660 (M+H). $C_{32}H_{30}IN_5O_3(M)$

EXAMPLE 21

Preparation of 1-[1-(3,4-methylenedioxybenzyl)-4-nitro-1H-imidazol-5-ylmethyl]-3-(4-methylpiperazin-1-yl)carbonyl-4-(naphthalen-1-yl)-1H-pyrrole(21)

162 mg(0.507 mmol) of the compound prepared in Preparation 4 was dissolved in 5 ml of dimethylformamide and the mixture was cooled to 0° C. 70 mg(1.75 mmol) of 60% sodium hydride dispersed in mineral oil was added. After stirring for 10 minutes, 150 mg(0.507 mmol) of the compound prepared in Preparation 5-3) was added. After stirring for 2 hours at room temperature, the solvent was removed and the residue thus obtained was subjected to column chromatography(eluent: dichloromethane/methanol=97/3, v/v) to give 60 mg(0.104 mmol, Yield 20%) of the title compound.

$^1$H NMR(CDCl$_3$) δ 1.12(brs, 2H), 1.83(brs, 2H), 1.88(s, 3H), 2.91(brs, 2H), 3.33(brs, 2H), 5.01(s, 2H), 5.49(s, 2H), 5.93(s, 2H), 6.47(s, 1H), 6.55(d, 1H), 6.75(d, 1H), 6.75(s, 1H), 7.12(s, 1H), 7.33d, 1H), 7.40–7.55(m, 4H), 7.78(d, 1H), 7.83(d, 1H), 8.00(d, 1H)

FAB 579 (M+H). $C_{32}H_{30}N_6O_3(M)$

EXAMPLE 22

Preparation of 1-[4-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(22)

To 25 mg(0.043 mmol) of the compound prepared in Example 21 in 2 ml of ethanol was added 4 mg of 10% Pd-C was added thereto, and the resulting mixture was stirred for 3 hours under hydrogen atmosphere (55–60 psi). The reaction mixture was filtered through celite and concentrated to give 15 mg(0.027 mmol, Yield 63%) of the title compound.

$^1$H NMR(CDCl$_3$) δ 1.12(brs, 2H), 1.84(brs, 2H), 1.89(s, 3H), 2.99(brs, 2H), 3.35(brs, 2H), 4.84(s, 2H), 4.89(s, 2H), 5.88(s, 2H), 6.48(s, 1H), 6.53(d, 1H), 6.60(d, 1H), 6.71(s, 1H), 7.03(s, 1H), 7.26(d, 1H), 7.30(d, 1H), 7.40–7.55(m, 3H), 7.77(d, 1H), 7.82(d, 1H), 8.01(d, 1H)

FAB 549 (M+H). $C_{32}H_{32}N_6O_3(M)$

EXAMPLE 23

Preparation of 3-(4-methoxypiperazin-1-yl) carbonyl-1-[4-methyl-1-(3,4-methylenedioxybenzyl)-1H-imidazol-5-ylmethyl]-4-(naphthalen-1-yl)-1H-pyrrole(23)

23-1) Preparation of 3-ethoxycarbonyl-1-[4-methyl-1-(3,4-methylenedioxybenzyl)-1H-imidazol-5-ylmethyl]-4-(naphthalen-1-yl)-1H-pyrrole 430 mg(1.62 mmol) prepared in Preparation 1-2) was dissolved in 30 ml of dimethylformamide and cooled to 0° C. 200 mg(5.00 mmol) of 60% sodium hydride dispersed in mineral oil was added slowly. After the mixture was stirred for 5 minutes, 510 mg(1.69 mmol) of the compound prepared in Preparation 11-4) was added slowly. After stirring for 2 hours at room temperature, dimethylformamide was removed under reduced pressure 200 ml of ethylacetate was added to the residue and the organic layer was washed with saturated sodium chloride solution (100 ml ×3). The organic layer was dried over anhydrous magnesium sulfate and concentrated. The residue thus obtained was subjected to column chromatography(eluent: dichloromethane/methanol=98/2, v/v) to give 672 mg (1.36 mmol, Yield 84%) of the title compound.

$^1$H NMR(CDCl$_3$) δ 0.67(t, 3H), 2.32(s, 3H), 3.85(q, 2H), 4.85(s, 2H), 4.91(s, 2H), 5.88(s, 2H), 6.43(s, 1H), 6.49–6.60 (s&d, 2H), 6.72(d, 1H), 7.20(d, 1H), 7.30–7.46(m, 4H), 7.51(s, 1H), 7.73(d, 1H), 7.78(d, 1H), 7.82(d, 1H)

FAB 480 (M+H), $C_{29}H_{25}N_3O_4(M)$ 23-2) Preparation of 3-hydroxycarbonyl-1-[4-methyl-1-(3,4-methyl-enedioxybenzyl)-1H-imidazol-5-ylmethyl]-4-(naphthalen-1-yl)-1H-pyrrole To 550 mg(1.1 mmol) of the compound prepared in Example 23-1) in a mixture of ethanol/water(50 ml/50 ml) was added 185 mg(3.3 mmol) of potassium hydroxide. After heating under reflux for 8 hours, ethanol was removed under reduced pressure. The pH of the solution was adjusted to 7–8 with 6H hydrochloric acid solution and the crude product was extracted with ethylacetate(100 ml×3). The organic layer was dried over anhydrous magnesium sulfate and concentrated. The residue was subjected to column chromatography (eluent: dichloromethane/methanol=93/7, v/v) to give 370 mg(0.79 mmol, Yield 72%) of the title compound.

$^1$H NMR(DMSO) 2.26(s, 3H), 5.22(s, 2H), 5.31(s, 2H), 5.91(s, 2H), 6.60–6.70(m, 3H), 6.80(d, 2H), 7.23(d, 1H), 7.29(s, 1H), 7.31–7.49(m, 2H), 7.64(d, 1H), 7.81(d, 1H), 7.89(d, 1H), 8.44(brs, 1H)

FAB 452(M+H), $C_{27}H_{21}N_3O_4(M)$ 23-3) Preparation of 3-(4-hydroxypiperazin-1-yl) carbonyl-1-[4-methyl-1-(3,4-methylenedioxybenzyl)-1H-imidazol-5-ylmethyl]-4-(naphthalen-1-yl)-1H-pyrrole 90 mg(0.20 mmol) of the compound prepared in Example 23-2) was dissolved in 30 ml of dimethylformamide. 42 mg(0.24 mmol) of the compound prepared in Preparation 20, 0.084 ml(0.60 mmol) of triethylamine, 57 mg(0.30 mmol) of EDC and 40 mg(0.30 mmol) of HOBT were sequentially added. After stirring for 8 hours, dimethylformamide was removed under reduced pressure and 150 ml of ethylacetate was added to the residue. The organic layer was washed with saturated sodium chloride solution(100 ml×3). The organic layer was dried over anhydrous magnesium sulfate and concentrated. The residue thus obtained was subjected to column chromatography(eluent: dichloromethane/methanol=93/7, v/v) to give 59 mg(0.11 mmol, Yield 55%) of the title compound.

$^1$H NMR(CDCl$_3$) δ 1.25(brs, 2H), 1.72(brs, 2H), 2.33(s, 3H), 2.45–2.85(brs, 4H), 4.88(s, 2H), 4.94(s, 2H), 5.90(s, 2H), 6.45(s, 1H), 6.51(d, 1H), 6.59(s, 1H), 6.71(d, 1H), 7.04(s, 1H), 7.19–7.56(m, 5H), 7.81(d, 1H), 7.86(d, 1H), 8.00(d, 1H)

FAB 536 (M+H), $C_{31}H_{29}N_5O_4(M)$ 23-4) Preparation of 3-(4-methoxypiperazin-1-yl) carbonyl-1-[4-methyl-1-(3,4-methylenedioxybenzyl)-1H-imidazol-5-ylmethyl]-4-(naphthalen-1-yl)-1H-pyrrole 56 mg(0.11 mmol) of the compound prepared in Example 23-3), 31 mg(0.22 mmol) of methyl iodide and 23 mg(0.44 mmol) of potassium hydroxide were added to 3 ml of dimethylsulfoxide and stirred for one hour. 15 ml of ethylacetate was added and the organic layer was washed with 10 ml of water and 10 ml of saturated aqueous sodium bicarbonate solution. The organic layer was dried over anhydrous sodium sulfate and the solvent was removed under reduced pressure. The residue thus obtained was subjected to column chromatography(eluent: dichloromethane/methanol=93/7, v/v) to give 11 mg (0.02 mmol, Yield 19%) of the title compound.

$^1$H NMR(CDCl$_3$) δ 1.24(br, 2H), 1.68(br, 4H), 2.33(s, 3H), 2.59(br, 2H), 3.26(s, 3H), 4.81(s, 2H), 4.91(s, 2H), 5.90(s, 2H), 6.42(s, 1H), 6.49(d, 2H), 6.61(s, 1H), 6.69(d, 1H), 7.03(s, 1H), 7.30(d, 1H), 7.35–7.42(m, 2H), 7.39(s, 1H), 7.78(d, 1H), 7.82(d, 1H), 7.99(d, 1H)

FAB 564 (M+H). C$_{33}$H$_{33}$N$_5$O$_4$(M)

EXAMPLE 24

Preparation of 2-methyl-1-[1-(3,4-methylenedioxybenzyl)-1H-imidazol-5-ylmethyl]-3-(4-methylpiperazin-1-yl)carbonyl-4-(naphthalen-1-yl)-1H-pyrrole(24)

24-1) Preparation of 3-methoxycarbonyl-2-methyl-1-[1-(3,4-methylenedioxybenzyl)-1H-imidazol-5-ylmethyl]-4-(naphthalen-1-yl)-1H-pyrrole 0.93 g(3.51 mmol) of the compound prepared in Preparation 18 was dissolved in 10 ml of dimethylformamide, 280 mg(7 mmol, 60%) of sodium hydride was added slowly and the mixture was stirred for 10 minutes. To the reaction mixture was added slowly 1.20 g(4.2 mmol) of the compound prepared in Preparation 10 at 0° C. and then reaction was carried out for 3 hours. The solvent was removed, 100 ml of water and 150 ml of ethylacetate were added to the residue and the mixture was stirred. The organic layer was separated and dried over anhydrous sodium sulfate. The organic solvent was removed under reduced pressure and the residue was subjected to column chromatography(eluent: dichloromethane/methanol=90/10, v/v) to give 0.34 g(0.7 mmol, Yield 20%) of the title compound.

$^1$H NMR(CDCl$_3$) δ 2.44(s, 3H), 3.23(s, 3H), 4.86(s, 2H), 4.87(s, 2H), 5.91(s, 2H), 6.36(s, 1H), 6.43(s, 1H), 6.44(d, 1H), 6.73(d, 1H), 7.04(s, 1H), 7.27(m, 1H), 7.32(m, 1H), 7.39(m, 2H), 7.52(s, 1H), 7.73(m, 2H), 7.81(m, 1H)

FAB 480 (M+H), C$_{29}$H$_{25}$N$_3$O$_4$(M)

24-2) Preparation of 3-hydroxycarbonyl-2-methyl-1-[1-(3,4-methylenedioxybenzyl)-1H-imidazol-5-ylmethyl]-4-(naphthalen-1-yl)-1H-pyrrole 0.34 g(0.71 mmol) of the compound prepared in Example 24-1) and 0.12 g(0.21 mmol) of potassium hydroxide were added to 20 ml of aqueous ethanol solution(1/1, v/v) and heated under reflux for 24 hours. After reaction was completed, the solvent was removed under reduced pressure. 20 ml of water was added to the residue, which was then neutralized with 1N hydrochloric acid and extracted twice with 20 ml of ethylacetate. The organic layer was dried over anhydrous sodium sulfate and the solvent was removed to give 0.21 g(Yield 63%) of the title compound.

$^1$H NMR(CDCl$_3$) δ 2.38(d, 3H), 4.63(s, 2H), 4.87(s, 2H0, 5.83(d, 2H), 6.22(s, 1H), 6.31–6.40(m, 2H), 6.45(s, 1H), 6.67(m, 1H), 7.01(s, 1H), 7.27–7.34(m, 4H), 7.49(s, 1H), 7.68–7.74(m, 3H)

FAB 466 (M+H), C$_{28}$H$_{23}$N$_3$O$_4$(M)

24-3) Preparation of 2-methyl-1-[1-(3,4-methylenedioxybenzyl)-1H-imidazol-5-ylmethyl]-3-(4-methylpiperazin-1-yl)carbonyl-4-(naphthalen-1-yl)-1H-pyrrole 37 mg(0.08 mmol) of the compound prepared in example 24-2), 18 mg(0.10 mmol) of EDC, 13 mg(0.10 mmol) of HOBT and 12 mg(0.12 mmol) of N-methylpiperazine were dissolved in 3 ml of dimethylformamide and stirred for 2 hours. The solvent was removed under reduced pressure. 8 ml of ethylacetate was added to the residue, which was then washed twice with 8 ml of water. The organic layer was dried over anhydrous sodium sulfate and the solvent was removed under reduced pressure. The residue thus obtained was subjected to column chromatography(eluent: dichloromethane/methanol=93/7, v/v) to give 20 mg (0.04 mmol, Yield 46%) of the title compound.

$^1$H NMR(CDCl$_3$) δ 1.80–2.10(br+s, 6H), 2.30(s, 3H), 2.93(br, 3H), 3.36(br, 2H), 4.99(s, 2H), 5.02(s, 2H), 5.93(s, 2H), 6.40–6.56(m, 3H), 6.74(d, 1H), 7.18(s, 1H), 7.28(d, 1H), 7.40–7.50(m, 3H), 7.57(s, 1H), 7.74(d, 1H), 7.82(d, 1H), 8.04(d, 1H)

FAB 548 (M+H), C33H33N5O3

EXAMPLE 25

Preparation of 2-ethylthio-1-[1-(3,4-methylenedioxybenzyl)-1H-imidazol-5-ylmethyl]-3-(4-methylpiperazin-1-yl)carbonyl-4-(naphthalen-1-yl)-1H-pyrrole(25)

25-1) Preparation of 3-ethoxycarbonyl-2-ethylthio-1-[1-(3,4-methylenedioxybenzyl)-1H-imidazol-5-ylmethyl]-4-(naphthalen-1-yl)-1H-pyrrole The compound of Preparation 19 was reacted according to the same procedure as Example 24-1) to give the title compound with a yield of 20%.

$^1$H NMR(CDCl$_3$) δ 0.63(t, 3H), 0.83(t, 3H), 2.22(q, 2H), 3.83(q, 2H), 4.96(s, 2H), 5.28(s, 2H), 5.85(s, 2H), 6.43(s, 1H), 6.51(d, 1H), 6.73(m, 1H), 7.23(–7.59(m, 7H), 7.81(m, 3H)

FAB 512 (M+H), C$_{29}$H$_{25}$N$_3$O$_4$S(M)

25-2) Preparation of 2-ethylthio-3-hydroxycarbonyl-1-[1-(3,4-methylenedioxybenzyl)-1H-imidazol-5-ylmethyl]-4-(naphthalen-1-yl)-1H-pyrrole The compound prepared in Example 25-1) was reacted according to the same procedure as Example 24-2) to give the title compound with a yield of 83%.

$^1$H NMR(CDCl$_3$) δ 0.70(t, 3H), 2.08(q, 2H), 5.20(s, 2H), 5.28(s, 2H), 5.82(s, 2H), 6.53(s, 1H), 6.58(d, 1H), 6.71(d, 1H), 6.91–7.23(m, 3H), 7.29(t, 1H), 7.38(m, 3H), 7.73(m, 3H), 8.80(br, 1H)

FAB 540 (M+H), C$_{31}$H$_{29}$N$_3$O$_4$S(M)

25-3) Preparation of 2-ethylthio-1-[1-(3,4-methylenedioxybenzyl)-1H-imidazol-5-ylmethyl]-3-(4-methylpiperazin-1-yl)carbonyl-4-(naphthalen-1-yl)-1H-pyrrole 23 mg(0.04 mmol) of the compound of Example 25-2) was reacted according to the same procedure as Example 24-3) to give the title compound with a yield of 30%.

$^1$H NMR(CDCl$_3$) δ 1.22(t, 3H), 1.68(br, 4H), 1.88(s, 3H), 2.44(q, 3H), 3.01(br, 2H), 3.17(br, 2H), 4.99(s, 2H), 5.25(s, 2H), 5.89(s, 2H), 6.44(s, 1H), 6.50(d, 1H), 6.70(d, 1H), 6.78(s, 1H), 7.15(s, 1H), 7.30(m, 2H), 7.42(m, 1H), 7.53(m, 2H), 7.74(d, 1H), 7.83(d, 1H), 7.98(d, 1H)

FAB 594 (M+H). C$_{34}$H$_{35}$N$_5$O$_3$S(M)

EXAMPLE 26

Preparation of 1-[1-(2-methoxyphenethyl)-2-methyl-1H-imidazol-5-ylmethyl]-3-(4-methylpiperazin-1-yl)carbonyl-4-(naphthalen-1-yl)-1H-pyrrole(26)

The compound of Preparation 14-4) and the compound of Preparation 4 were reacted according to the same procedure as Example 15 to give the title compound with a yield of 75%.

¹H NMR(CDCl₃) δ 1.09(br, 2H), 1.70–2.10(br+s, 5H), 2.30(s, 3H), 2.76(t, 2H), 3.00(br, 2H), 3.31(br, 2H), 3.39(s, 3H), 3.93(t, 2H), 4.79(s, 2H), 6.70(d, 1H), 6.84(m, 2H), 6.90(m, 1H), 6.94(d, 1H), 7.09(d, 1H), 7.25(m, 1H), 7.32(m, 1H), 7.30–7.50(m, 3H), 7.74(d, 1H), 7.81(d, 1H), 8.02(d, 1H)

FAB 548(M+H). $C_{34}H_{37}N_5O_2$

EXAMPLE 27

Preparation of 1-[1-(3-ethoxypropyl)-2-methyl-1H-imidazol-5-ylmethyl]-3-(4-methylpiperazin-1-yl) carbonyl-4-(naphthalen-1-yl)-1H-pyrrole(27)

49 mg(0.1 mmol) of 1-[1-(3-ethoxypropyl)-1H-imidazol-5-ylmethyl]-3-(4-methylpiperazin-1-yl)carbonyl-4-(naphthalen-1-yl)-1H-pyrrole prepared by referring to the literature(see: PCT/KR98/00377) was dissolved in 4 ml of tetrahydrofuran and the reaction mixture was cooled to −78° C. 48 μl (2.5N hexane solution, 0.12 mmol) of n-butyllithium was added and 16 mg (0.13 mmol) of dimethylsulfate was added thereto. After reaction was carried out for one hour, the solvent was removed. The residue was subjected to HPLC to give 11 mg of the title compound in the form of trifluoroacetic acid salt.

¹H NMR(CDCl₃+CH₃OD) δ 1.08(t, 3H), 1.15(m, 2H), 1.74(br, 2H), 2.18(s, 3H), 2.61(s, 3H), 2.84(br, 2H), 3.37(t, 2H), 3.39(q, 2H), 3.49(br, 4H), 4.07(t, 2H), 5.25(s, 2H), 6.84(s, 1H), 7.21(s, 1H), 7.31(d, 1H), 7.50–7.60(m, 4H), 7.75–7.91(m, 3H)

FAB 500 (M+H). $C_{30}H_{37}N_5O_2$(M)

EXAMPLE 28

Preparation of 1-[1-(3-ethoxypropyl)-4-methyl-1H-imidazol-5-ylmethyl]-3-(4-methylpiperazin-1-yl) carbonyl-4-(naphthalen-1-yl)-1H-pyrrole(28)

130 mg(0.407 mmol) of the compound prepared in Preparation 4 was dissolved in 30 ml of dimethylformamide and cooled to 0° C. 60 mg (1.5 mmol) of 60% sodium hydride dispersed in mineral oil was added slowly. After stirring for 5 minutes, 130 mg(0.53 mmol) of the compound prepared in Preparation 17-4) was added slowly and the mixture was stirred for 2 hours at room temperature. Dimethylformamide was removed under reduced pressure, and the residue was dissolved in 200 ml of ethylacetate and the organic layer was washed with saturated sodium chloride solution (100 ml×3). The organic layer was dried over anhydrous magnesium sulfate and concentrated. The residue thus obtained was subjected to column chromatography(eluent: ethylacetate/ dichloromethane/methanol=60/30/10, v/v/v) to give 1150 mg (0.230 mmol, Yield 57%) of the title compound.

¹H NMR(CDCl₃) δ 1.15(br, 2H), 1.16(t, 3H), 1.72(m, 2H), 1.81(brs, 2H), 1.87(s, 3H), 2.32(s, 3H), 2,95(brs, 2H), 3.27(t, 2H), 3.29(brs, 2H), 3.41(q, 2H), 3.94(t, 2H), 5.9(s, 2H), 6.68(s, 1H), 7.08(s, 1H), 7.32(d, 1H), 7.39–7.51(m, 4H), 7.76(d, 1H), 7.82(d, 1H), 8.02(d, 1H)

FAB 500 (M+H). $C_{30}H_{37}N_5O_2$(M)

EXAMPLE 29

Preparation of 1-[1-(3-benzyloxypropyl)-4-methyl-1H-imidazol-5-ylmethyl]-3-(4-methylpiperazin-1-yl) carbonyl-4-(naphthalen-1-yl)-1H-pyrrole(29)

104 mg(0.326 mmol) of the compound prepared in Preparation 4 was dissolved in 3 ml of dimethylformamide and cooled to 0° C. 40 mg(1 mmol) of 60% sodium hydride dispersed in mineral oil was added thereto. After stirring for 5 minutes, 94 mg(0.298 mmol) of the compound prepared in Preparation 15-6) was added and the mixture was stirred for 2 hours at room temperature. 50 ml of ethylacetate was added and the organic layer was washed with aqueous sodium chloride solution(20 ml×3). The organic layer was dried over anhydrous magnesium sulfate and concentrated. The residue thus obtained was subjected to column chromatography(eluent: dichloromethane/methanol–90/10, v/v) to give 110 mg(0.196 mmol, Yield 66%) of the title compound.

¹H NMR(CDCl₃) δ 1.10brs, 2H), 1.63–1.95(m, 4H), 1.86(s, 3H), 2.31(s, 3H), 2.94(brs, 2H), 3.25–3.45(brs & t, 4H), 3.94(t, 2H), 4.43(s, 2H), 5.05(s, 2H), 6.63(s, 1H), 7.04(s, 1H), 7.25–7.55(m, 10H), 7.77(d, 1H), 7.83(d, 1H), 8.00(d, 1H)

FAB 562 (M+H). $C_{35}H_{39}N_5O_2$ (M)

EXAMPLE 30

Preparation of 1-[1-(3-benzyloxypropyl)-4-methyl-1H-imidazol-5-ylmethyl]-3-[N-(2-methoxyethyl)-N-methyl]carbamoyl-4-(naphthalen-1-yl)-1H-pyrrole (30)

The compound of Preparation 2 and the compound of Preparation 15-6) were reacted according to the same procedure as Example 29 to give the title compound with a yield of 71%.

¹H NMR(CDCl₃) δ 1.77(m, 3H), 2.31(s, 3H), 2.39(brs, 2H), 2.72(brs, 1H), 3.02(brs, 3H), 3.07(brs, 1H), 3.31(brs, 1H), 3.36(t, 2H), 3.94(t, 2H), 4.44(s, 2H), 5.05(s, 2H), 6.63(s, 1H), 6.99(s, 1H), 7.25–7.48(m, 11H), 7.75(d, 1H), 7.83(d, 1H), 8.04(d, 1H)

FAB 551 (M+H). $C_{34}H_{38}N_4O_3$(M)

EXAMPLE 31

Preparation of 1-{1-[3-(2-chlorobenzyloxy)propyl]-4-methyl-1H-imidazo-5-ylmethyl}-3-(4-methylpiperazin-1-yl)carbonyl-4-(naphthalen-1-yl)-1H-pyrrole(31)

83 mg(0.26 mmol) of the compound prepared in Preparation 4 was dissolved in 30 ml of dimethylformamide and cooled to 0° C. 20 mg(0.50 mmol) of 60% sodium hydride dispersed in mineral oil was slowly added thereto. After stirring for 5 minutes, 100 mg(0.29 mmol) of the compound prepared in Preparation 16-5) was added slowly and the mixture was stirred for 2 hours at room temperature. Dimethylformamide was removed under reduced pressure, and the residue was dissolved in 200 ml of ethylacetate and the organic layer was washed with aqueous sodium chloride solution (100 ml×3). The organic layer was dried over anhydrous magnesium sulfate and concentrated. The residue thus obtained was subjected to column chromatography (eluent: ethylacetate/dichloromethane/methanol=60/ 30/10, v/v/v) to give 72 mg(0.12 mmol, Yield 46%) of the title compound.

¹H NMR(CDCl₃) δ 1.09(brs, 2H), 1.63–1.95(m, 4H), 1.85(s, 3H), 2.31(s, 3H), 2.92(brs, 2H), 3.40(brs, 2H), 3.43(t, 2H), 3.95(t, 2H), 4.52(s, 2H), 5.06(s, 2H), 6.63(s, 1H), 7.00(s, 1H), 7.15–7.55(m, 9H), 7.76(d, 1H), 7.82(d, 1H), 8.00(d, 1H)

FAB 596 (M+H). $C_{35}H_{38}ClN_5O_2$(M)

EXAMPLE 32

Preparation of 1-{1-[3-(2-chlorobenzyloxy)propyl]-4-methyl-1H-imidazol-5-ylmethyl}-3-[N-(2-methoxyethyl)-N-methyl]carbamoyl-4-(naphthalen-1-yl)-1H-pyrole(32)

91 mg(0.30 mmol) of the compound prepared in Preparation 2 was dissolved in 30 ml of dimethylformamide and cooled to 0° C. 35 mg(0.88 mmol) of 60% sodium hydride dispersed in mineral oil was added slowly. After stirring for 5 minutes, 114 mg(0.33 mmol) of the compound prepared in Preparation 16-5) was added slowly and the mixture was stirred for 2 hours at room temperature. Dimethylformamide was removed under reduced pressure, and the residue was dissolved in 200 ml of ethylacetate and the organic layer was washed with aqueous sodium chloride solution (100 ml×3). The organic layer was dried over anhydros magnesium sulfate and concentrated. The residue thus obtained was subjected to column chromatography(eluent: dichloromethane/methanol=98/2, v/v) to give 93 mg(0.16 mmol, Yield 53%) of the title compound.

$^1$H NMR(CDCl$_3$) δ 1.80(m, 2H), 2.32(s, 3H), 2.39(brs, 2H), 2.71(brs, 1H), 3.02(brs, 3H), 3.08(brs, 1H), 3.32(brs, 1H), 3.32(t, 2H), 3.98(t, 2H), 4.53(s, 2H), 5.06(s, 2H), 6.64(s, 1H), 7.00(s, 1H), 7.17(t, 2H), 7.50–7.26(m, 9H), 7.75(d, 1H), 7.83(d, 1H), 8.05(d, 1H)

FAB 585 (M+H). C$_{34}$H$_{37}$ClN$_4$O$_3$(M)

EXAMPLE 33

Preparation of 1-[1-(3-benzyloxypropyl)-2-methyl-1H-imidazol-5-ylmethyl]-3-(4-methylpiperazin-1-yl)carbonyl-4-(naphthalen-1-yl)-1H-pyrrole(33)

55 mg(0.1 mmol) of 1-[1-(3-benzyloxypropyl)-1H-imidazol-5-yl methyl]-3-(4-methylpiperazin-1-yl) carbonyl-4-(naphthalen-1-yl)-1H-pyrrole prepared by referring to the literature(see: PCT/KR98/00377) was dissolved in 4 ml of tetrahydrofuran and the reaction mixture was cooled to −78° C. 48 μl(2.5N hexane solution, 0.12 mmol) of n-butyllithium and 16 mg(0.13 mmol) of dimethylsulfate were added. After reaction was carried out for one hour, the solvent was removed. The residue was subjected to HPLC to give 14 mg of the title compound in the form of trifluoroacetic acid salt.

$^1$H NMR(CH$_3$OD+CDCl$_3$) δ 1.84(m, 2H), 2.13(s, 3H), 2.60(s, 3H), 3.21(br, 4H), 3.37(t, 2H), 3.92(br, 4H), 4.12(t, 2H), 4.30(s, 2H), 5.14(s, 2H), 7.07–7.38(m, 12H), 7.76(m, 3H)

FAB 562 (M+H). C$_{35}$H$_{39}$N$_5$O$_2$(M)

EXAMPLE 34

Preparation of 1-[1-(3-benzyloxypropyl)-2-methyl-1H-imidazol-5-ylmethyl]-3-[N-(2-methoxyethyl)-N-methyl]carbamoyl-4-(naphthalen-1-yl)-1-yl)-1H-pyrrole(34)

54 mg(0.1 mmol) of 1-[1-(3-benzyloxypropyl)-1H-imidazol-5-yl methyl]-3-[N-(2-methoxyethyl)-N-methyl]carbamoyl-4-(naphthalen-1-yl)-1H-pyrrole prepared by referring to the literature(see: PCT/KR98/00377) was dissolved in 4 ml of tetrahydrofuran and the reaction mixture was cooled to −78° C. 48 μl(2.5N hexane solution, 0.12 mmol) of n-butyllithium and 16 mg(0.13 mmol) of dimethylsulfate were added. After reaction was carried out for one hour, the solvent was removed. The residue was subjected to HPLC to give 13 mg of the title compound in the form of trifluoroacetic acid salt.

$^1$H NMR(CDCl$_3$) δ 1.86(m, 2H), 2.42(s, 2H), 2.60–2.82 (m+s, 5H), 3.00–3.05(m+s, 4H), 3.10(s, 1H), 3.34(s, 1H), 3.43(t, 2H), 4.03(t, 2H), 4.43(s, 2H), 6.63(s, 1H), 7.03(s, 1H), 7.15–7.31(m, 5H), 7.43(m, 5H), 7.79(d, 1H), 7.85(d, 1H), 7.93(d, 1H).

FAB 551 (M+H). C$_{34}$H$_{38}$N$_4$O$_3$(M)

EXAMPLE 35

Preparation of 1-[1-(phenethyl)-2-methyl-1H-imidazol-5-ylmethyl]-3-(4-methylpiperazin-1-yl)carbonyl-4-(naphthalen-1-yl)-1H-pyrrole(35)

64 mg(0.13 mmol) of 1-[1-(phenethyl)-1H-imidazol-5-ylmethyl]-3-(4-methylpiperazin-1-yl)carbonyl-4-(naphthalen-1-yl)-1H-pyrrole prepared by referring to the literature (see: PCT/KR98/00377) was dissolved in $^4$ ml of tetrahydrofuran and the reaction mixture was cooled to −78° C. 66 μl (2.5N hexane solution, 0.16 mmol) of n-butyllithium and 21 mg (0.16 mmol) of dimethylsulfate were added. After reaction was carried out for one hour, the solvent was removed. The residue was subjected to HPLC to give 13 mg of the title compound in the form of trifluoroacetic acid salt.

$^1$H NMR(CH$_3$OD+CDCl$_3$) δ 2.00–2.30(br+s, 6H), 2.39(t, 2H), 2.70–3.10(br, 8H), 4.13(t, 2H), 4.65(s, 2H), 6.98(m, 2H), 7.10–7.60 (m, 10H), 7.89(m, 3H)

FAB 518 (M+H). C$_{33}$H$_{35}$N$_5$O (M)

Preparation 21

Preparation of 1(4-chlorobenzyl)-5-chloromethyl-1H-imidazole hydrochloride 21-1) Preparation of 1-(4-chlorobenzyl)-5-hydroxymethyl-1H-imidazole Dihydroxyacetone dimer and 4-chlorobenzylamine hydrochloride were reacted according to the same procedure as Preparation 9-1) to give the title compound with a yield of 68%.

$^1$H NMR(DMSO) δ 4.31(d, 2H), 5.11(t, 1H), 5.22(s, 2H), 6.82(s, 1H), 7.17(d, 2H), 7.41(d, 2H), 7.68(s, 1H)

FAB 223(M+1), C$_{11}$H$_{11}$ClN$_2$O (M)

21-2) Preparation of 1-(4-chlorobenzyl)-5-chloromethyl-1H-imidazole hydrochloride The compound of Preparation 21-1) was reacted according to the same procedure as Preparation 9-5) to give the title compound with a yield of 90%. The product thus obtained was directly used in the next reaction without purification.

Preparation 22

Preparation of 1-(4-bromobenzyl)-5-chloromethyl-1H-imidazole hydrochloride 22-1) Preparation of 1-(4-bromobenzyl)-5-hydroxymethyl-1H-imidazole Dihydroxyacetone dimer and 4-bromobenzylamine hydrochloride were reacted according to the same procedure as Preparation 9-1) to give the title compound with a yield of 65%.

$^1$H NMR(DMSO) δ 4.32(s, 2H), 5.24(s, 2H), 6.93(s, 1H), 7.13(d, 2H), 7.54(d, 2H), 7.88(s, 1H)

FAB 267 (M+1), C$_{11}$H$_{11}$BrN$_2$O (M)

22-2) Preparation of 1-(4-bromobenzyl)-5-chloromethyl-1H-imidazole hydrochloride The compound of Preparation 22-1) was reacted according to the same procedure as Preparation 9-5) to give the title compound with a yield of 88%. The product thus obtained was directly used in the next reaction without purification.

Preparation 23

Preparation of 5-chloromethyl-1-phenethyl-1H-imidazole hydrochloride 23-1) Preparation of 5-hydroxymethyl-1-phenethyl-1H-imidazole Dihydroxyacetone dimer and phenethylamine were reacted according to the same procedure as Preparation 9-1) to give the title compound with a yield of 70%.

$^1$H NMR(CDCl$_3$) δ 3.08 (t, 2H), 4.27 (t, 2H), 4.47 (s, 2H), 6.89 (s, 1H), 7.05 (d, 2H), 7.26(m, 3H), 7.44 (s, 1H)

FAB 203 (M+1), C$_{12}$H$_{14}$N$_2$O (M)

23-2) Preparation of 5-chloromethyl-1-phenethyl-1H-imidazole hydrochloride

The compound of Preparation 23-1) was reacted according to the same procedure as Preparation 9-5) to give the title compound with a yield of 90%. The product thus obtained was directly used in the next reaction without purification.

Preparation 24

Preparation of 5-chloromethyl-1-(4-methyl) phenethyl-1H-imidazole hydrochloride 24-1) Preparation of 5-hydroxymethyl-1-(4-methyl) phenethyl-1H-imidazole Dihydroxyacetone dimer and 4-methylphenethylamine were reacted according to the same procedure as Preparation 9-1) to give the title compound with a yield of 72%.

$^1$H NMR(CDCl$_3$) δ 3.02(t, 2H), 2.99(t, 2H), 3.76(br, 1H), 4.19 (t, 2H), 4.47(s, 2H), 6.83(s, 1H), 6.94(d, 2H), 7.06(d, 2H), 7.28(s, 1H)

FAB 217 (M+1), C$_{13}$H$_{16}$N$_2$O (M)

24-2) Preparation of 5-chloromethyl-1-(4-methyl) phenethyl-1H-imidazole hydrochloride The compound of Preparation 24-1) was reacted according to the same procedure as Preparation 9-5) to give the title compound with a yield of 93%. The product thus obtained was directly used in the next reaction without purification.

Preparation 25

Preparation of 5-chloromethyl-1-(4-chloro) phenethyl-1H-imidazole hydrochloride 25-1) Preparation of 1-(4-chloro)phenethyl-5-hydroxymethyl-1H-imidazole Dihydroxyacetone dimer and 4-chlorophenethylamine were reacted according to the same procedure as Preparation 9-1) to give the title compound with a yield of 73%.

$^1$H NMR(CDCl$_3$) δ 3.04(t, 2H), 4.18 (t, 2H), 4.48(s, 2H), 6.79(s, 1H), 6.96(d, 2H), 7.20–7.40(m, 3H)

FAB 237 (M+1), C$_{12}$H$_{13}$ClN$_2$O (M)

25-2) Preparation of 5-choromethyl-1-(4-chloro) phenethyl-1H-imidazole hydrochloride The compound of Preparation 25-1) was reacted according to the same procedure as Preparation 9-5) to give the title compound with a yield of 90%. The product thus obtained was directly used in the next reaction without purification.

Preparation 26

Preparation of 5-chloromethyl-1-(4-fluoro) phenethyl-1H-imidazole hydrochloride 26-1) Preparation of 1-(4-fluoro)phenethyl-5-hydroxymethyl-1H-imidazole Dihydroxyacetone dimer and 4-fluorophenethylamine were reacted according to the same procedure as Preparation 9-1) to give the title compound with a yield of 72%.

$^1$H NMR(CDCl$_3$) δ 2.99(t, 2H), 3.76(br, 1H), 4.15 (t, 2H), 4.45(s, 2H), 6.80–7.20(m, 5H), 7.26(s, 1H)

FAB 221 (M+1), C$_{12}$H$_{13}$FN$_2$O(M)

26-2) Preparation of 5-chloromethyl-1-(4-fluoro) phenethyl-1H-imidazole hydrochloride The compound of Preparation 26-1) was reacted according to the same procedure as Preparation 9-5) to give the title compound with a yield of 89%. The product thus obtained was directly used in the next reaction without purification.

Preparation 27

Preparation of 1-(3-bromo)phenethyl-5-chloromethyl-1H-imidazole hydrochloride 27-1) Preparation of 1-(3-bromo)phenethyl-5-hydroxymethyl-1H-imidazole Dihydroxyacetone dimer and 3-bromophenethylamine were reacted according to the same procedure as Preparation 9-1) to give the title compound with a yield of 72%.

$^1$H NMR(DMSO) δ 3.04(t, 2H), 4.20 (t, 2H), 5.11(t, 1H), 6.75 (d, 1H), 7.10–7.25(m, 2H), 7.41(m, 3H)

FAB 281(M+1), C$_{12}$H$_{13}$BrN$_2$O (M)

27-2) Preparation of 1-(3bromo)phenethyl-5-chloromethyl-1H-imidazole hydrochloride The compound of Preparation 27-1) was reacted according to the same procedure as Preparation 9-5) to give the title compound with a yield of 94%. The product thus obtained was directly used in the next reaction without purification.

Preparation 28

Preparation of 5-chloromethyl-1-(4-methoxy) phenethyl-1H-imidazole hydrochloride 28-1) Preparation of 5-hydroxymethyl-1-(4-methoxy) phenethyl-1H-imidazole Dihydroxyacetone dimer and 4-methoxyphenethylamine were reacted according to the same procedure as Preparation 9-1) to give the title compound with a yield of 60%.

$^1$H NMR(CDCl$_3$) δ 2.91(t, 2H), 3.68(s, 3H), 4.09(t, 2H), 4.36(s, 2H), 6.70(d, 2H), 6.77(s, 1H), 6.87(d, 2H), 7.13 (s, 1H)

FAB 233 (M+1), C$_{13}$H$_{16}$N$_2$O$_2$(M)

28-2) Preparation of 5-chloromethyl-1-(4-methoxy) phenethyl-1H-imidazole hydrochloride The compound of Preparation 28-1) was reacted according to the same procedure as Preparation 9-5) to give the title compound with a yield of 91%. The product thus obtained was directly used in the next reaction without purification.

Preparation 29

Preparation of 5-chloromethyl-1-(3-methoxy) phenethyl-1H-imidazole hydrochloride 29-1) Preparation of 5-hydroxymethyl-1-(3-methoxy) phenethyl-1H-imidazole Dihydroxyacetone dimer and 3-methoxyphenethylamine were reacted according to the same procedure as Preparation 9-1) to give the title compound with a yield of 65%.

$^1$H NMR(CDCl$_3$) δ 3.03(t, 2H), 3.75(s, 3H), 4.16(t, 2H), 4.47(s, 2H), 4.75(s, 1H), 6.74(s, 1H), 6.75–7.00(m, 3H), 7.13–7.30(m, 1H)

FAB 233 (M+1), C$_{13}$H$_{16}$N$_2$O$_2$(M)

29-2) Preparation of 5-chloromethyl-1-(3-methoxy) phenethyl-1H-imidazole hydrochloride The compound of Preparation 29-1) was reacted according to the same procedure as Preparation 9-5) to give the title compound with a yield of 90%. The product thus obtained was directly used in the next reaction without purification.

Preparation 30

Preparation of 5-chloromethyl-1-(naphthalen-1-yl) ethyl-1H-imidazole hydrochloride 30-1) Preparation of 5-hydroxymethyl-1-(naphthalen-1-yl)ethyl-1H-imidazole Dihydroxyacetone dimer and 1-naphthylethylamine were reacted according to the same procedure as Preparation 9-1) to give the title compound with a yield of 58%.

¹H NMR(CDCl₃) δ 3.44 (t, 2H), 4.23 (t, 2H), 4.38(s, 2H), 6.79(s, 1H), 7.07(d, 1H), 7.17(s, 1H), 7.24(t, 1H), 7.32–7.48 (m, 2H), 7.62(d, 1H), 7.74(d, 1H), 7.92(d, 1H)

FAB 253 (M+1), $C_{16}H_{16}N_2O$ (M)

30-2) Preparation of 5-chloromethyl-1-(naphthalen-1-yl) ethyl-1H-imidazole hydrochloride The compound of Preparation 30-1) was reacted according to the same procedure as Preparation 9-5) to give the title compound with a yield of 87%. The product thus obtained was directly used in the next reaction without purification.

Preparation 31

Preparation of 5-chloromethyl-1-(3-ethoxypropyl)-1H-imidazole hydrochloride 31-1) Preparation of 5-hydroxymethyl-3-(3-ethoxypropyl)-1H-imidazole Dihydroxyacetone dimer and 3-ethoxypropylamine hydrochloride were reacted according to the same procedure described in a literature (see: *J. Med. Chem.*, 33, 1312–1329, 1990) to give the title compound.

¹H NMR(CDCl₃) 1.13(t, 3H), 1.97 (m, 2H), 3.29(t, 2H), 3.39(q, 2H), 4.03(t, 2H), 4.51(s, 2H), 6.74 (s, 1H)

FAB (M+1), $C_9H_{16}N_2O_2$ (M)

31-2) Preparation of 5-chloromethyl-1-(3-ethoxypropyl)-1H-imidazole hydrochloride The compound of Preparation 31-1) was reacted according to the same procedure as Preparation 9-5) to give the title compound with a yield of 85%. The product thus obtained was directly used in the next reaction without purification.

Preparation 32

Preparation of 5-chloromethyl-1-methyl-1H-imidazole hydrochloride 32-1) Preparation of 5-hydroxymethyl-1-methyl-1H-imidazole Dihydroxyacetone dimer and methylamine hydrochloride were reacted according to the same procedure described in a literature (see: *J. Med. Chem.*, 33, 1312–1329, 1990) to give the title compound.

¹H NMR(DMSO) δ 3.60 (s, 3H), 4.46 (s, 2H), 6.78(s, 1H), 7.54(s, 1H)

FAB (M+1), $C_5H_8N_2O$ (M)

32-2) Preparation of 5-chloromethyl-1-methyl-1H-imidazole hydrochloride

The compound of Preparation 32-1) was reacted according to the same procedure as Preparation 9-5) to give the title compound with a yield of 87%. The product thus obtained was directly used in the next reaction without purification.

Preparation 33

Preparation of 5-chloromethyl-1-(naphthalen-2-yl)methyl-1H-imidazole hydrochloride 33-1) Preparation of 5-hydroxymethyl-1-(naphthalen-2-yl)methyl-1H-imidazole Dihydroxyacetone dimer and 2-naphthylmethylamine were reacted according to the same procedure as Preparation 9-1) to give the title compound with a yield of 58%.

¹H NMR(CDCl₃) δ 4.36(s, 2H), 5.28(s, 2H), 6.89(s, 1H), 7.17(d, 1H), 7.35(m, 2H), 7.41(s, 1H), 7.50(s, 1H), 7.65(m, 1H), 7.69(m, 2H)

FAB 239 (M+1), $C_{15}H_{14}N_2O$ (M)

33-2) Preparation of 5-choromethyl-1-naphthalen-2-yl) methyl-1H-imidazole hydrochloride The compound of Preparation 33-1) was reacted according to the same procedure as Preparation 9-5) to give the title compound with a yield of 87%. The product thus obtained was directly used in the next reaction without purification.

Preparation 34

Preparation of 3-(naphthalen-1-yl)-4-nitro-1H-pyrrole 34-1) Preparation of 1-[(E)-2-nitroethenyl]naphthalene 7.81 g (50 mmol) of 1-naphthaldehyde and 1.54 g (20 mmol) of ammonium acetate were added to 70 ml of nitromethane and heated under reflux for 3 hours (see: *J. Org. Chem.*, 1984, 49, 4761). 100 ml of ethylacetate was added and the resulting mixture was washed with 50 ml of water and 50 ml of brine. The organic layer was collected and dried over anhydrous magnesium sulfate. The solvent was removed under reduced pressure and the residue was subjected to column chromatography (eluent: hexane/ethylacete=90/10, v/v) to give 6.27 g( 0.031 mmol, Yield 62%) of the title compound.

¹H NMR(CDCl₃) δ 7.48(t, 1H), 7.60(m, 3H), 7.69(d, 1H), 7.90(d, 1H), 7.86(d, 1H), 8.10(d, 1H), 8.76(d, 1H)

FAB 200 (M+1): $C_{12}H_9NO_2$ (M)

34-2) Preparation of 3-(naphthalen-1-yl)-4-nitro-1H-pyrrole 6.27 g(31.5 mmol) of 1-[(E)-2-nitroethyl]naphthalene prepared in Preparation 34-1) and 9.23 g(47.3 mmol) of tosylmethylisocyanide were dissolved in 100 ml of tetrahydrofuran. 7.07 g (63.1 mmol) of potassium t-butoxide in 100 ml of tetrahydrofuran was added slowly at 0° C. and the mixture was stirred for 2 hours at room temperature. After reaction the solvent was removed and 100 ml of ethylacetate was added to the residue. The organic layer was washed with 50 ml saturated aqueous sodium bicarbonate solution and the organic layer was dried over anhydrous magnesium sulfate. The solvent was removed under reduced pressure and the residue was subjected to column chromatography (eluent: hexane/ethylacetate=70/30, v/v) to give 3.12 g (0.013 mol, Yield 42%) of the title compound.

¹H NMR(CDCl₃) δ 6.48(s, 1H), 7.32–7.52(m, 4H), 7.62 (s, 1H), 7.74(d, 1H), 7.87(m, 2H), 9.34(s, 1H)

FAB 225(M+1): $C_{14}H_{10}O_2N$ (M)

EXAMPLE 36

Preparation of 1-[1-(3,4-methylenedioxybenzyl)-1H-imidazol-5-ylmethyl]-4-(naphthalen-1-yl)-3-nitro-1H-pyrrole(36)

To 135 mg (0.57 mmol) of the compound prepared in Preparation 34-2) in 2 ml of dimethylformamide was added 45 mg (1.14 mmol) of sodium hydride (60%) was added at 0° C. and the resulting mixture was stirred for 5 minutes. 200 mg (0.66 mmol) of the compound prepared in Preparation 10 was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 187 mg (Yield 73%) of the title compound.

¹H NMR(CDCl₃) δ 4.89(s, 2H), 4.92(s, 2H), 5.86(s, 2H), 6.38(s, 1H), 6.44(m, 2H), 6.69(d, 1H), 7.22(s, 1H), 7.25–7.40(m, 3H), 7.44(m, 2H), 7.58(d, 1H), 7.61(s, 1H), 7.83(t, 2H)

FAB (M+1) 453, $C_{26}H_{20}N_4O_4$ (M)

EXAMPLE 37

Preparation of 1-[1-(4-chlorobenzyl)-1H-imidazol-5-ylmethyl]-4-(naphthalen-1-yl)-3-nitro-1H-pyrrole (37)

To 120 mg (0.5 mmol) of the compound prepared in Preparation 34-2) in 2 ml of dimethylformamide was added 40 mg (1.0 mmol) of sodium hydride (60%) of 0° C., and the resulting mixture was stirred for 5 minutes. 170 mg (0.6 mmol) of the compound prepared in Preparation 21-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 136 mg (Yield 75%) of the title compound.

¹H NMR(CDCl₃) δ 5.06(s, 4H), 6.71(d, 1H), 6.96(d, 2H), 7.11(d, 1H), 7.28–7.48(m, 5H), 7.62(m, 1H), 7.66(s, 1H), 7.78(m, 2H), 7.82(m, 1H), 7.93(d, 1H)

FAB 443 (M+1), $C_{25}H_{19}ClN_4O_2$ (M)

EXAMPLE 38

Preparation of 1-[1-(4-bromobenzyl)-1H-imidazol-5-ylmethyl]-4-(naphthalen-1-yl)-3-nitro-1H-pyrrole (38)

To 62 mg (0.26 mmol) of the compound prepared in Preparation 34-2) in 2 ml of dimethylformamide was added 21 mg (0.52 mmol) of sodium hydride (60%) at 0° C., and the resulting mixture was stirred for 5 minutes. 100 mg (0.31 mmol) of the compound prepared in Preparation 22-2) was added thereto and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography (eluent: dichloromethane/methanol=95/5, v/v) to give 79 mg (Yield 62%) of the title compound.

¹H NMR(CDCl₃) δ 4.86(s, 2H), 4.90(s, 2H), 6.43(d, 1H), 6.80(d, 2H), 7.23(s, 1H), 7.28(m, 1H), 7.33–7.50(m, 6H), 7.56(d, 1H), 7.59(s, 1H), 7.83(t, 2H)

FAB 488(M+1), $C_{25}H_{19}BrN_4O_2$ (M)

EXAMPLE 39

Preparation of 1-[1-(phenethyl)-1H-imidazol-5-ylmethyl]-4-(naphthalen-1-yl)-3-nitro-1H-pyrrole (39)

To 794 mg (3.34 mmol) of the compound prepared in Preparation 34-2) in 5 ml of dimethylformamide was added 270 mg (6.75 mmol) of sodium hydride (60%) at 0° C., and the resulting mixture was stirred for 5 minutes. 1.03 g (4.0 mmol) of the compound prepared in Preparation 23-2) was added and the resulting mixture was stirred for 3 hours at room temperature. The solvent was removed under reduced pressure and 9 ml of water was added to the residue. The mixture thus obtained was extracted twice with 20 ml of the ethylacetate and the combined organic layer was dried over anhydrous sodium sulfate and concentrated. The residue was subjected to column chromatography(eluent: dichloromethane/methanol=95/5, v/v) to give 766 mg (Yield 54%) of the title compound.

¹H NMR(CDCl₃) δ 2.87(t, 2H), 4.03(t, 2H), 4.69(s, 2H), 6.54(d, 1H), 6.96(m, 2H), 7.11(s, 1H), 7.21–7.39(m, 5H), 7.44(m, 3H), 7.58(m, 2H), 7.85(m, 2H)

FAB 432(M+1), $C_{26}H_{22}N_4O_2$ (M)

EXAMPLE 40

Preparation of 1-[1-(4-methylphenethyl)-1H-imidazol-5-ylmethyl]-4-(naphthalen-1-yl)-3-nitro-1H-pyrrole(40)

To 56 mg (0.23 mmol) of the compound prepared in Preparation 34-2) in 2 ml of dimethylformamide was added 19 mg (0.47 mmol) of sodium hydride (60%) at 0° C., and the resulting mixture was stirred for 5 minutes. 76 mg (0.28 mmol) of the compound prepared in Preparation 24-2) was added thereto and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 55 mg (Yield 54%) of the title compound.

¹H NMR(CDCl₃) δ 2.33(s, 3H), 2.77(t, 2H), 3.96(t, 2H), 4.66(s, 2H), 6.52(s, 1H), 6.83(d, 2H), 7.06(m, 3H), 7.30–7.50(m, 5H), 7.59(m, 2H), 7.85(m, 2H)

FAB 437(M+1), $C_{27}H_{24}N_4O_2$ (M)

EXAMPLE 41

Preparation of 1-[1-(4-chlorophenethyl)-1H-imidazol-5-ylmethyl]-4-(naphthalen-1-yl)-3-nitro-1H-pyrrole(41)

To 65 mg (0.27 mmol) of the compound prepared in Preparation 34-2) was dissolved in 2 ml of dimethylformamide was added. 22 mg (0.44 mmol) of sodium hydride (60%) at 0° C., and the resuling mixture was stirred for 5 minutes. 91 mg (0.32 mmol) of the compound prepared in Preparation 25-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 40 mg (Yield 32%) of the title compound.

¹H NMR(CDCl₃) δ 2.76(t, 2H), 3.97(t, 2H) 4.81(s, 2H), 6.56(d, 1H), 6.86(d, 2H), 7.13(s, 1H), 7.23(m, 2H), 7.30(d, 2H), 7.35(s, 1H), 7.44(m, 2H), 7.56(d, 1H), 7.62(d, 1H), 7.85(m, 2H)

FAB 457(M+1), $C_{26}H_{21}ClN_4O_2$ (M)

EXAMPLE 42

Preparation of 1-[1-(4-fluorophenethyl)-1H-imidazol-5-ylmethyl]-4-(naphthalen-1-yl)-3-nitro-1H-pyrrole(42)

To 46 mg (0.19 mmol) of the compound prepared in Preparation 34-2) in 2 ml of dimethylformamide was added 15 mg (0.38 mmol) of sodium hydride (60%) at 0° C., and the resulting mixture was stirred for 5 minutes. 80 mg(0.29 mmol) of the compound prepared in Preparation 26-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 47 mg (Yield 55%) of the title compound.

$^1$H NMR(CDCl$_3$) δ 2.75(t, 2H), 3.96(t, 2H), 4.78(s, 2H), 6.56(d, 1H), 6.81–7.01(m, 4H), 7.12(s, 1H), 7.32(m, 3H), 7.44(m, 2H), 7.60(m, 2), 7.85(m, 2H)

FAB 441 (M+1), C$_{26}$H$_{31}$FN$_4$O$_2$ (M)

EXAMPLE 43

Preparation of 1-[1-(3-bromophenethyl)-1H-imidazol-5-ylmethyl]-4-(naphthalen-1-yl)-3-nitro-1H-pyrrole(43)

To 75 mg (0.31 mmol) of the compound prepared in Preparation 34-2) in 2 ml of dimethylformamide was added 25 mg (0.62 mmol) of sodium hydride (60%) at 9° C., and the resulting mixture was stirred for 5 minutes. 155 mg (0.46 mmol) of the compound prepared in Preparation 27-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 43 mg (Yield 27%) of the title compound.

$^1$H NMR(CDCl$_3$) δ 2.75(t, 2H), 3.98(t, 2H), 4.79(s, 2H), 6.56(d, 1H), 6.83(d, 1H), 7.09–7.20(m, 3H), 7.32(d, 2H), 7.35–7.50(m, 4H), 7.57(d, 1H), 7.61(d, 1H), 7.84(m, 2H)

FAB 502(M+1), C$_{26}$H$_{21}$BrN$_4$O$_2$ (M)

EXAMPLE 44

Preparation of 1-[1-(4-methoxyphenethyl)-1H-imidazol-5-ylmethyl]-4-(naphthalen-1-yl)-3-nitro-1H-pyrrole(44)

To 56 mg (0.23 mmol) of the compound prepared in Preparation 34-2) in 2 ml of dimethylformamide was added 20 mg (0.50 mmol) of sodium hydride (60%) at 0° C., and the resulting mixture was stirred for 5 minutes. 80 mg (0.28 mmol) of the compound prepared in Preparation 28-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 70 mg (Yield 66%) of the title compound.

$^1$H NMR(CDCl$_3$) δ 2.74(t, 2H), 3.73(s, 3H), 3.95(t, 2H), 4.70(s, 2H), 6.52(d, 1H), 6.77(d, 2H), 6.84(d, 2H), 7.07(s, 1H), 7.32(m, 2H), 7.37(s, 1H), 7.43(m, 2H), 7.58(m, 2H), 7.84(m, 2H)

FAB 453(M+1), C$_{27}$H$_{24}$N$_4$O$_3$ (M)

EXAMPLE 45

Preparation of 1-[1-(3-methoxyphenethyl)-1H-imidazol-5-ylmethyl]-4-(naphthalen-1-yl)-3-nitro-1H-pyrrole(45)

To 62 mg (0.26 mmol) of the compound prepared in Preparation 34-2) in 2ml of dimethylformamide was added 21 mg (0.53 mmol) of sodium hydride(60%) at 0° C., and the resulting mixture was stirred for 5 minutes. 89 mg (0.31 mmol) of the compound prepared in Preparation 29-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 26 mg (Yield 22%) of the title compound.

$^1$H NMR(CDCl$_3$) δ 2.91(t, 2H), 3.78(s, 3H), 4.03(t, 2H), 4.79(s, 2H), 6.54(d, 1H), 6.87(m, 3H), 7.09(s, 1H), 7.25(m, 1H), 7.33(m, 2H), 7.44(m, 3H), 7.60(m, 2H), 7.85(m, 2H)

FAB 453(M+1), C$_{27}$H$_{4}$O$_3$ (M)

EXAMPLE 46

Preparation of 1-[1-(naphthalen-1-ylethyl)-1H-imidazol-5-ylmethyl]-4-(naphthalen-1-yl)-3-nitro-1H-pyrrole(46)

To 40 mg (0.27 mmol) of the compound prepared in Preparation 34-2) in 2 ml of dimethylformamide was added 20 mg (0.50 mmol) of sodium hydride (60%) at 0° C., and the resulting mixture was stirred for 5 minutes. 62 mg (0.55 mmol) of the compound prepared in Preparation 30-2) was added thereto and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 23 mg (Yield 29%) of the title compound.

$^1$H NMR(CDCl$_3$) δ 3.38(t, 2H), 4.15(s, 2H), 4.21(t, 2H), 6.17(d, 1H), 6.96(d, 1H), 7.00(s, 1H), 7.12(m, 1H), 7.25–7.35(m, 3H), 7.41–7.60(m, 6H), 7.80–7.92(m, 5H)

FAB 473(M+1), C$_{30}$H$_{24}$N$_4$O$_2$ (M)

EXAMPLE 47

Preparation of 1-[1-(3-ethoxypropyl)-1H-imidazol-5-ylmethyl]-4-(naphthalen-1-yl)-3-nitro-1H-pyrrole (47)

To 67 mg (0.28 mmol) of the compound prepared in Preparation 34-2) in 2 ml of dimethylformamide was added 23 mg (0.48 mmol) of sodium hydride(60%) at 0° C., and the resulting mixture was stirred for 5 minutes. 81 mg(0.34 mmol) of the compound prepared in Preparation 31-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent:

dichloromethane/methanol=95/5 v/v) to give 70 mg (Yield 62%) of the title compound.

$^1$H NMR(CDCl$_3$) δ 1.16(t, 3H), 1.76(m, 2H), 3.20(t, 2H), 3.35(m, 2H), 3.93(t, 2H), 5.09(s, 2H), 6.60(s, 1H), 7.16(s, 1H), 7.30–7.40(m, 2H), 7.45(t, 2H), 7.54(s, 1H), 7.61(d, 1H), 7.67(d, 1H), 7.85(m, 2H)

FAB 405 (M+1), C$_{23}$H$_{24}$N$_4$O$_3$ (M)

EXAMPLE 48

Preparation of 1-[1-(methyl)-1H-imidazol-5-ylmethyl]-4-(naphthalen-1-yl)-3-nitro-1H-pyrrole (48)

To 1.02 g (4.30 mmol) of the compound prepared in Preparation 34-2) in 2 ml of dimethylformamide was added 340 mg (8.5 mmol) of sodium hydride(60%) at 0° C., and the resulting mixture was stirred for 5 minutes. 860 mg (5.14 mmol) of the compound prepared in Preparation 32-2) was added and the resulting mixture was stirred for 3 hours at room temperature. The solvent was removed under reduced pressure and 6 ml of water was added to the residue. The mixture thus obtained was extracted twice with 20 ml of ethylacetate and the combined organic layer was dried over anhydrous sodium sulfate and concentrated. The residue was subjected to column chromatography(eluent: dichloromethane/methanol=95/5, v/v) to give 818 mg (Yield 57%) of the title compound.

$^1$H NMR(CDCl$_3$) δ 3.44(s, 3H), 5.03(s, 2H), 6.56(d, 1H), 7.16(s, 1H), 7.30–7.40(m, 2H), 7.41–7.51 (m, 3H), 7.61(m, 2H), 7.84(m, 2H)

FAB 333 (M+1), C$_{19}$H$_{16}$N$_4$O$_2$ (M)

EXAMPLE 49

Preparation of 1-[1-(naphthalen-2-ylmethyl)-1H-imidazol-5-ylmethyl]-4-(naphthalen-1-yl)-3-nitro-1H-pyrrole(49)

To 107 mg (0.45 mmol) of the compound prepared in Preparation 34-2) in 2 ml of dimethylformamide was added 36 mg (0.9 mmol) of sodium hydride (60%) at 0° C., and the resulting mixture was stirring for 5 minutes. 130 mg (0.54 mmol) of the compound prepared in Preparation 33-2) was added and the resulting mixture was stirred for 3 hours at room temperature. The solvent was removed under reduced pressure and 3 ml of water was added to the residue. The mixture thus obtained was extracted twice with 10 ml of ethylacetate and the combined organic layer was dried over anhydrous sodium sulfate and concentrated. The residue was subjected to column chromatography(eluent: dichloromethane/methanol=95/5, v/v) to give 179 mg (Yield 87%) of the title compound.

$^1$H NMR(CDCl$_3$) δ 4.95(s, 2), 5.19(s, 2H), 6.43(d, 1H), 7.08(m, 2H), 7.22–7.54(m, 8H), 7.65–7.90(m, 7H)

FAB 459(M+1), C$_{29}$H$_{22}$N$_4$O$_2$ (M)

EXAMPLE 50

Preparation of 3-amino-1-[1-(4-chlorobenzyl)-1H-imidazol-5-ylmethyl]-4-(naphthalen-1-yl)-1H-pyrrole(50)

To 132 mg(0.30 mmol) of the compound prepared in Example 37 in 5 m of methanol was added 10 mg of Pd/C and the reaction was carried out for 2 hours under H$_2$ atmosphere at 40 psi. After reaction, the reaction mixture was filtered and the solvent was removed under reduced pressure. 3 ml of water was added to the residue. This mixture was extracted twice with 10 ml of ethylacetate and the combined organic layer was dried over anhydrous sodium sulfate and concentrated. The residue was subjected to column chromatography(eluent: dichloromethane/methanol=95/5, v/v) to give 67 mg (Yield 54%) of the title compound.

$^1$H NMR(CD$_3$OD) δ 4.93(s, 2H), 5.09(s, 1H), 5.15(s, 1H), 6.53(d, 1H), 6.93(d, 1H), 7.11(d, 1H), 7.16–7.25(m, 4H), 7.28–7.41(m, 4H), 7.67(d, 1H), 7.72(d, 1H), 7.78(d, 1H), 7.84(s, 1H)

FAB 413(M+1), C$_{26}$H$_{21}$ClN$_4$ (M)

Preparation 35

Preparation of 4-(3-bromonaphthalen-1-yl)-3-(4-methylpiperazin-1-yl)carbonyl-1H-pyrrole 35-1) Preparation of 3-bromo-1-methyl-naphthalene A 250 ml three-neck round bottomed flask was equipped with a reflux condenser and two addition funnels. 430 mg(2.2 mmol) of 4-bromo-6-methyl-2-pyrone prepared according to the procedure described in a literature(see: M. Cervera, *Tetrahedron*, 46, 7885, 1990) from 4-hydroxy-6-methyl-2-pyrone and phosphorus tribromide was dissolved in 100 ml of ethyleneglycol dimethylether(DME), which was then introduced into the flask. Catalytic amount of trifluoroacetic acid was added and the resulting mixture was heated under reflux. While refluxing, isoamylnitrite(0.48 ml, 3.4 mmol) and anthranilic acid (470 mg, 3.4 mmol) in DME which were contained in the funnels, respectively, were added dropwise simultaneously. After confirming that the starting materials were completely reacted, addition was stopped and the reaction solution was cooled. The solvent was removed under reduced pressure and the remaining materials were diluted with 250 ml of dichloromethane. The resulting solution was sequentially washed with 5% aqueous hydrochloric acid solution, 5% aqueous sodium hydroxide solution and water, and then dried over anhydrous magnesium sulfate. The solvent was removed and the residue was subjected to column chromatography(eluent: n-Hexane/ethylacetate=20/1, v/v) to give 340 mg(Yield 68%) of the title compound.

$^1$H NMR (CDCl$_3$) δ 2.67(s, 3H), 7.41(brs, 1H), 7.51(m, 2H), 7.74(brd, 1H), 7.86(brs, 1H), 7.94(brd, 1H)

35-2) Preparation of 3-bromo-1-naphthaldehyde 500 ml of 50% aqueous acetic acid solution wherein cerium ammonium nitrite(3.29 g, 6.0 mmol) was included was added dropwise to 350 ml of acetic acid solution of the compound prepared in Preparation 35-1) (330 mg, 1.5 mmol) at 85° C. The reaction mixture was stirred for 2 hours at the same temperature, cooled, and extracted with dichloromethane(200 ml×3). Organic layers were combined, washed with water and dried over anhydrous magnesium sulfate. The solvent was removed under reduced pressure and the residue was subjected to column chromatography (eluent: n-hexane/ethylacetate=10/1, v/v) to give 34 mg (Yield 9%) of the title compound.

$^1$H NMR(CDCl$_3$) δ 7.61(t, 1H), 7.70(t, 1H), 7.84(brd, 1H), 8.05(brs, 1H), 8.25(brs, 1H), 9.15(brd, 1H)

35-3) Preparation of 4-(3-bromonaphthalen-1-yl)-1H-pyrrole-3-carboxylic acid

The compound prepared in Preparation 35-2) (177 mg, 0.75 mmol) and triethylphosphonoacetate (0.15 ml, 0.75 mmol) were added to ethyleneglycol dimethylether(DME) and the reaction mixture was cooled with ice water. Potassium t-butoxide(94 mg, 0.8 mmol) was added portionwise over 10 minutes. After stirring for 1.5 hour at room temperature, TosMIC(177 mg, 0.8 mmol) was added at 0° C. After stirring for 10 minutes, potassium t-butoxide (120 mg, 1.1 mmol) was added in portions over 5 minutes and the resulting mixture was stirred for 2 hours at room temperature. After reaction was completed, DME was removed under reduced pressure, and the residue was diluted with 50 ml of saturated aqueous sodium bicarbonate solution and 50 ml of ethylacetate. The organic layer was separated and the aqueous layer was extracted again with the same solvent (50 ml×2). Organic layers were combined and dried over anhydrous sodium sulfate. The solvent was removed under reduced pressure and 20 ml of a solvent mixture of water and ethanol(1:1, v/v) was added to the residue. Potassium hydroxide (50 mg, 9 mmol) was added and the resulting mixture was heated under reflux for 2 days. After confirming the completion of reaction, ethanol was removed under reduced pressure and the aqueous layer was washed with 20 ml of ethylacetate. The remaining aqueous layer was neutralized with 6N aqueous hydrochloric acid solution and extracted with dichloromethane (30 ml×3). The organic layer was dried over anhydrous magnesium sulfate and concentrated by removing the solvent to give 18 mg (Total yield of 3 steps 7.6%) of the pure title compound without further purification steps.

$^1$H NMR(CDCl$_3$) δ 6.82(d, 1H), 7.37(td, 1H), 7.44(td, 1H), 7.44(d, 1H), 7.58(d, 1H), 7.75(brd, 1H), 7.77(brd, 1H), 7.96(brd, 1H)

35-4) Preparation of 4-(3-bromonaphthalen-1-yl)-3-(4-methylpiperazin-1-yl)carbonyl-1H-pyrrole To the compound prepared in Preparation 35-3) (18 mg, 0.057 mmol) in dimethylformamide were added EDC (33mg, 0.17 mmol) and HOBT (25 mg, 0.17 mmol). After 4-methylpiperazine (7 mg, 0.07 mmol) was added, the resulting mixture was stirred for 2 hours at room temperature. After confirming the completion of reaction, the solvent was removed under reduced pressure. The residue thus obtained was diluted with 10 ml of saturated aqueous sodium bicarbonate solution and 10 ml of ethylacetate. The organic layer was separated and the aqueous layer was extracted with the same solvent (10 ml×2). Organic layers were combined and dried over anhydrous magnesium sulfate. The solvent was removed under reduced pressure and the residue was subjected to column chromatography (eluent: dichloro- methane/methanol=95/5, v/v) to give 4 mg (Yield 18%) of the title compound.

$^1$H NMR(CDCl$_3$) δ 1.24(brs, 1H), 1.56–1.94(m, 4H), 1.96(s, 3H), 3.03(brs, 2H), 3.40(brs, 2H), 6.91(t, 1H), 7.20(t, 1H), 7.41–7.49(m, 3H), 7.74(brd, 1H), 7.94(brs, 1H), 8.05 (brd, 1H), 9.25(brs, 1H)

Preparation 36

Preparation of 4-(3-chloronaphthalen-1-yl)-3-(4-methylpiperazin-1-yl)carbonyl-1H-pyrrole 36-1) Preparation of 3-chloro-1-methyl-naphthalene A three-neck round-bottomed flask was equipped with a reflux condenser and two addition funnels. Dry DME(200 ml) was introduced into the flask and 4-chloro-6-methyl-2-pyrone(3.24 g, 22.4 mmol) prepared according to the procedure described in a literature (see: M. J. D. Van Dam et F. KOGL, Recueil 83, 39, 1964) from 4-hydroxy-6-methyl-2-pyrone and phosphorusoxychloride, and trifluoroacetic acid (0.1 ml) were added thereto. Isoamylnitrite(3.15 g, 26.9 mmol) and anthranilic acid(3.69 g, 26.9 mmol) each dissolved in DME(50 ml) were introduced into the respective funnels. The isoamylnitrite solution and anthranilic acid solution were added dropwise simultaneously while keeping the reflux condition. After confirming that the starting materials were completely used, addition was stopped and the reaction solution was cooled. The solvent was removed under reduced pressure and the residue was dissolved in methyene chloride(100 ml) and the organic layer was sequentially washed with 5% aqueous hydrochloric acid solution, 5% aqueous sodium hydroxide solution and water. The organic layer was dried over anhydrous magnesium sulfate and concentrated. The residue was subjected to column chromatography(eluent: n-hexane/ethylacetate=9/1, v/v) to give 2.60 g(14.7 mmol, Yield 55%) of the title compound.

$^1$H NMR(CDCl$_3$) δ 2.67(s, 3H, CH3), 7.28(s, 1H, ArH), 7.48–7.53 (m, 2H, ArH), 7.69(s, 1H, ArH), 7.73–7.76(m, 1H), 7.94–7.96(m, 1H)

36-2) Preparation of 1-(bromomethyl)-3-chloronaphthalene

Carbon tetrachloride(30 ml) was added to 3-Chloro-1-methyl-naphthalene(2.55 g, 14.4 mmol) prepared in Preparation 36-1) and NBS (2.82 g, 15.8 mmol). A small quantity of benzoylperoxide was added as an initiator and the resulting mixture was heated under reflux for 3 hours. The reaction solution was cooled and filtered to remove the insoluble solid. The filtrate was concentrated and subjected to column chromatography(eluent: hexane/ethylacetate=95/5, v/v) to give 3.10 g(12.1 mmol, Yield 84%) of the title compound.

$^1$H NMR(CDCl$_3$) δ 4.89(s, 2H, CH2Br), 7.51(d, 1H, J=1.8 Hz, ArH), 7.55(t, 1H, J=7.35 Hz, ArH), 7.61(t, 1H, J=7.55 Hz, ArH), 7.79(d, 1H, J=8.25 Hz, ArH), 7.82(s, 1H, ArH), 8.10(d, 1H, J=8.25 Hz, ArH)

36-3) Preparation of 3-chloro-1-naphthaldehyde

The compound of Preparation 36-2) (3.00 g, 11.7 mmol) and trimethylamine-N-oxide dihydrate(3.90 g, 35.1 mmol) were added to a solvent mixture of DMSO(10 ml) and methylenechloride(5 ml), and the resulting mixture was stirred for 3 hours at room temperature. Ethylacetate(100 $_{ml}$) was added and the mixture thus obtained was washed three times with aqueous sodium chloride solution. The organic layer was dried over anhydrous magnesium sulfate and concentrated. The residue was subjected to column chromatography(eluent: hexane/ethylacetate=9/1, v/v) to give 1.80 g(9.44 mmol, Yield 81%) of the title compound.

$^1$H NMR(CDCl$_3$) δ 7.59–7.70(m, 2H), 7.84(d, 1H), 7.93 (s, 1H), 8.07(s, 1H), 9.15(d, 1H), 10.36(s, 1H)

36-4) Preparation of 4-(3-chloronaphthalen-1-yl)-1H-pyrrole-3-carboxylic acid

The compound prepared in Preparation 36-3) (704 mg, 3.7 mmol) and triethylphosphonoacetate(0.8 ml, 4.1 mmol) were added to ethyleneglycol dimethylether(DME) and the reaction mixture was cooled with ice water. Potassium t-butoxide(500 mg, 4.4 mmol) was added in portions over 10 minutes. After stirring for about 1.5 hour at room temperature, TosMIC(870 mg, 4.4 mmol) was added at 0° C. After stirring for 10 minutes, potassium t-butoxide(580 mg, 5.2 mmol) was added in portions over 5 minutes and the resulting mixture was stirred for 2 hours at room temperature. After reaction was completed, DME was removed under reduced pressure, and the residue was diluted with 100 ml of saturated aqueous sodium bicarbonate solution and 100 ml of ethylacetate. The organic layer was separated and the aqueous layer was extracted again with the same solvent (100 ml×2). Organic layers were combined and dried over anhydrous sodium sulfate. After the solvent was removed under reduced pressure, 40 ml of a solvent mixture of water and ethanol(1:1, v/v) was added to the residue. Potassium hydroxide(50 mg, 9 mmol) was added and the resulting mixture was heated under reflux for 2 days. After confirming the completion of reaction, ethanol was removed under reduced pressure and the aqueous layer was washed with 40 ml of ethylacetate. The remaining aqueous layer was neutralized with 6N aqueous hydrochloric acid solution and extracted with dichloromethane(50 ml×3). The organic layer was dried over anhydrous magnesium sulfate and concentrated by removing the solvent to give 89 mg(0.032 mmol, Total yield of 3 steps 8.9%) of the pure title compound without further purification steps.

$^1$H NMR(CDCl$_3$) δ 6.82(d, 1H), 7.37(td, 1H), 7.44(td, 1H), 7.44(d, 1H), 7.58(d, 1H), 7.62(brd, 1H), 7.75(brd, 1H), 7.96(brd, 1H)

36-5) Preparation of 4-(3-chloronaphthalen-1-yl)-3-(4-methylpiperazin-1-yl)carbonyl-1H-pyrrole To the compound prepared in Preparation 36-4) (42 mg, 0.15 mmol) in dimethylformamide were added EDC(66 mg, 0.34 mmol) and HOBT(50 mg, 0.34 mmol). After 4-methylpiperazine (18 mg, 0.18 mmol) was added, the resulting mixture was stirred for 2 hours at room temperature. After confirming the completion of reaction, the solvent was removed under reduced pressure. The residue thus obtained was diluted with 10 ml of saturated aqueous sodium bicarbonate solution and 10 ml of ethylacetate. The organic layer was separated and the aqueous layer was extracted with the same solvent(10 ml×2). Organic layers were combined and dried over anhydrous magnesium sulfate. The solvent was removed under reduced pressure and the residue was subjected to column chromatography (eluent: dichloro- methane/methanol=95/5, v/v) to give 25 mg(Yield 47%) of the title compound.

$^1$H NMR(CDCl$_3$) δ 1.24(brs, 1H), 1.56–1.94(m, 4H), 1.96(s, 3H), 3.02(brs, 2H), 3.40(brs, 2H), 6.91(t, 1H), 7.19(t, 1H), 7.35(d, 1H), 7.40–7.49(m, 2H), 7.75(brd, 1H), 7.76 (brs, 1H), 8.05(brd, 1H), 9.45(brs, 1H)

Preparation 37

Preparation of 5-chloromethyl-4-methyl-1-(naphthalen-2-yl)methyl-1H-imidazole hydrochloride 37-1) Preparation of 5-(hydroxymethyl)-4-methyl-1-naphthalen-2-yl)methyl-1H-imidazole To 5-(t-Butyldimethylsiloxymethyl)-4-methyl-1H-imidazole(1.35 g, 5.95 mmol) in 40 ml of dimethylformamide was added 60% sodium hydride(600 mg) dispersed in mineral oil at 0° C. After stirring for 15 at 0° C. 2-(bromomethyl)-naphthalene(2.0 g, 9.0 mmol) was added. After stirring for 2 hours at room temperature, the solvent was removed under reduced pressure. The residue was diluted with 100 ml of saturated aqueous sodium bicarbonate solution and 100 ml of ethylacetate. The organic layer was separated and the remaining aqueous layer was extracted with the same solvents(70 ml×2). Organic layers were combined and dried over anhydrous magnesium sulfate. After the solvent was removed under reduced pressure, the residue was dissolved in 60 ml of tetrahydrofuran. To the solution was added 6 ml of 1.0M tetrabutylammonium fluoride solution, and the resulting mixture was stirred for one hour at room temperature. After reaction was completed, the solvent was removed under reduced pressure. The residue was diluted with 100 ml of saturated aqueous sodium bicarbonate solution and 100 ml of ethylacetate, the organic layer was separated, and the remaining aqueous layer was extracted with the same solvents(70 ml×2). Organic layers were combined and dried over anhydrous magnesium sulfate. The solvent was removed under reduced pressure and the residue was subjected to column chromatography (eluent: dichloromethane/methanol=95/5, v/v) to separate the two isomers and to give 375 mg(Total yield of 2 steps 25%) of the title compound.

$^1$H NMR(CDCl$_3$) δ 2.20(s, 3H), 4.44(s, 2H), 5.41(s, 2H), 7.30(dd, 1H), 7.45–7.49(m, 2H), 7.61(brs, 1H), 7.65(s, 1H), 7.81–7.85 (m, 3H)

37-2) Preparation of 5-chloromethyl-4-methyl-1-(naphthalen-2-yl)methyl-1H-imidazole hydrochloride To the compound prepared in Preparation 37-1) (375 mg, 0.15 mmol) in 40 ml of chloroform was added thionyl chloride(0.33 ml, 0.45 mmol) at room temperature, and the resulting mixture was stirred for one hour. After reaction was completed, the solvent and the remaining thionyl chloride was removed under reduced pressure. Without further purification, the title compound (330 mg, Yield 75%) was obtained.

$^1$H NMR(CDCl$_3$) δ 2.23(s, 3H), 4.46(s, 2H), 5.64(s, 2H), 7.30(dd, 1H), 7.45–7.49(m, 2H), 7.61(brs, 1H), 7.81–7.85 (m, 3H), 9.35(s, 1H)

EXAMPLE 51

Preparation of 4-(3-bromonaphthalen-1-yl)-1-[4-methyl-1-(3,4-methylenedioxybenzyl)-1H-imidazol-5-ylmethyl]-3-(4-methyl piperazin-1-yl)carbonyl-1H-pyrrole(51)

The compound prepared in Preparation 35-4) (11 mg, 0.045 mmol) was dissolved in 5 ml of dimethylformamide, which was then cooled to 0° C. At the same temperature, 5 mg of 60% sodium hydride dispersed in mineral oil was added slowly and the resulting mixture was stirred for 5 minutes. The compound prepared in Preparation 11-4) (13 mg, 0.045 mmol) was added slowly and the resulting mixture was stirred for 2 hours at room temperature. Dimethylformamide was removed under reduced pressure, 20 ml of ethylacetate was added to the residue, and the mixture thus obtained was washed with aqueous sodium chloride solution(10 ml×3). The organic layer was dried over anhydrous magnesium sulfate and concentrated. The residue was subjected to column chromatography(eluent: ethylacetate/methanol=4/1, v/v) to give 4 mg(0.0065 mmol, Yield 16%) of the title compound.

$^1$H NMR(CDCl$_3$) δ 1.24(brs, 1H), 1.56–1.94(m, 4H), 1.96(s, 3H), 2.33(s, 3H), 3.03(brs, 2H), 3.40(brs, 2H), 4.89 (s, 2H), 4.94(s, 2H), 5.91(s, 2H), 6.40(s, 1H), 6.50(d, 1H), 6.57(d, 1H), 6.71(d, 1H), 7.02(d, 1H), 7.39–7.52(m, 4H), 7.75(d, 1H), 7.95(brs, 2H)

EXAMPLE 52

Preparation of 4-(3-chloronaphthalen-1-yl)-1-[4-methyl-1-(3,4-methylenedioxybenzyl)-1H-imidazol-5-ylmethyl]-3-(4-methyl piperazin-1-yl)carbonyl-1H-pyrrole(52)

The compound prepared in Preparation 36-5) (4 mg, 0.011 mmol) was dissolved in 5 ml of dimethylformamide, which was then cooled to 0° C. 1 mg of 60% sodium hydride dispersed in mineral oil was added slowly and the resulting mixture was stirred for 5 minutes. The compound prepared in Preparation 11-4) (3 mg, 0.02 mmol) was added slowly and the resulting mixture was stirred for 2 hours at room temperature. Dimethylformamide was removed under reduced pressure, 20 ml of ethylacetate was added to the residue, and the mixture thus obtained was washed with aqueous sodium chloride solution(100 ml×3). The organic layer was dried over anhydrous magnesium sulfate and concentrated. The residue was subjected to column chromatography (eluent: ethylacetate/methanol=4/1, v/v) to give 3 mg(0.0052 mmol, Yield 47%) of the title compound.

$^1$H NMR(CDCl$_3$) δ 1.24(brs, 1H), 1.56–1.94(m, 4H), 1.93(s, 3H), 2.33(s, 3H), 3.02(brs, 2H), 3.40(brs, 2H), 4.88 (s, 2H), 4.93(s, 2H), 5.91(s, 2H), 6.42(s, 1H), 6.50(brd, 1H), 6.56(d, 1H), 6.71(d, 1H), 7.01(d, 1H), 7.40–7.52(m, 4H), 7.74(d, 1H), 7.75(s, 1H), 7.95(d, 1H)

EXAMPLE 53

Preparation of 4-(3-bromonaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(53)

The compound prepared in Preparation 35-4) (13 mg, 0.033 mmol) was dissolved in 5 ml of dimethylformamide, which was then cooled to 0° C. 6 mg of 60% sodium hydride dispersed in mineral oil was added slowly and the resulting mixture was stirred for 5 minutes. The compound prepared in Preparation 37-2) (12 mg, 0.039 mmol) was added slowly and the resulting mixture was stirred for 2 hours at room temperature. Dimethylformamide was removed under reduced pressure, 20 ml of ethylacetate was added to the residue, and the mixture thus obtained was washed with aqueous sodium chloride solution(10 ml×3). The organic layer was dried over anhydrous magnesium sulfate and concentrated. The residue was subjected to column chromatography (eluent: ethylacetate/methanol=4/1, v/v) to give 4 mg(0.0063 mmol, Yield 19%) of the title compound.

$^1$H NMR(CDCl$_3$) δ 1.15(brs, 1H), 1.56–1.94(m, 4H), 1.90(s, 3H), 2.37(s, 3H), 2.77(brs, 2H), 3.33(brs, 2H), 4.91 (s, 2H), 5.15(s, 2H), 6.53(d, 1H), 7.00(d, 1H), 7.14(d, 1H), 7.27(d, 1H), 7.38–7.49(m, 5H), 7.62(brs, 1H), 7.71–7.84(m, 4H), 7.89(d, 1H), 7.92(d, 1H)

EXAMPLE 54

Preparation of 4-(3-chloronaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(54)

The compound prepared in Preparation 36-5) (12 mg, 0.036 mmol) was dissolved in 5 ml of dimethylformamide, which was then cooled to 0° C. 6 mg of 60% sodium hydride dispersed in mineral oil was added slowly and the resulting mixture was stirred for 5 minutes. The compound prepared in Preparation 37-2) (12 mg, 0.039 mmol) was added slowly and the resulting mixture was stirred for 2 hours at room temperature. Dimethylformamide was removed under reduced pressure, 20 ml of ethylacetate was added to the residue, and the mixture thus obtained was washed with aqueous sodium chloride solution(10 ml×3). The organic layer was dried over anhydrous magnesium sulfate and concentrated. The residue was subjected to column chromatography (eluent: ethylacetate/methanol=4/1, v/v) to give 3 mg(0.0051 mmol, Yield 14%) of the title compound.

$^1$H NMR(CDCl$_3$) δ 1.24(brs, 1H), 1.56–1.94(m, 4H), 1.92(s, 3H), 2.37(s, 3H), 2.78(brs, 2H), 3.36(brs, 2H), 4.92 (s, 2H), 5.18(s, 2H), 6.54(d, 1H), 7.01(d, 1H), 7.13(d, 1H), 7.15(d, 1H), 7.37–7.48(m, 5H), 7.62(s, 1H), 7.72–7.80(m, 5H), 7.90(d, 1H)

EXAMPLE 55

Preparation of 1-[4-methyl-1-(naphthalen-2-yl) methyl-1H-imidazol-5-ylmethyl]-3-(4-methylpiperazin-1-yl)carbonyl-4-(naphthalen-1-yl)-1H-pyrrole(55)

The compound prepared in Preparation 4) (150 mg, 0.47 mmol) was dissolved in 30 ml of dimethylformamide, which was then cooled to 0° C. 80 mg of 60% sodium hydride dispersed in mineral oil was added slowly and the resulting mixture was stirred for 5 minutes. The compound prepared in Preparation 37-2) (150 mg, 0.49 mmol) was added slowly and the resulting mixture was stirred for 2 hours at room temperature. Dimethylformamide was removed under reduced pressure, 100 ml of ethylacetate was added to the residue, and the mixture thus obtained was washed with aqueous sodium chloride solution(100 ml×3). The organic layer was dried over anhydrous magnesium sulfate and concentrated. The residue was subjected to column chromatography (eluent: ethylacetate/methanol=4/1, v/v) to give 55 mg(0.006 mmol, Yield 21%) of the title compound.

$^1$H NMR(CDCl$_3$) δ 1.24(brs, 1H), 1.56–1.94(m, 4H), 1.86(s, 3H), 2.36(s, 3H), 2.83(brs, 2H), 3.32(brs, 2H), 4.91 (s, 2H), 5.14(s, 2H), 6.56(d, 1H), 7.02(d, 1H), 7.13(d, 1H), 7.18(d, 1H), 7.37–7.52(m, 6H), 7.59(s, 1H), 7.74–7.83(m, 5H), 7.98(d, 1H)

EXPERIMENTAL EXAMPLE 1

Analysis of Inhibitory Activity for Ras Farnesyl Transferase

In the present experiment, the improved Pompliano's method (see: Pompliano et al., *Biochemistry*, 31, 3800, 1992) was applied. Specifically, Ras farnesyl transferase produced by genetic recombination techniques was used, and fused protein of H-Ras(H-Ras-CVLS) substituted with polybasic lysine domain at C-terminus of K-Ras (see: Korean Patent Appln. No. 97-14409) was used as a substrate after it had been purified according to the known method (see, Chung et al., *Biochimica et Biophysica Acta*, 1129, 278, 1992).

The enzyme reaction was performed in 50 μl of 50 mM Sodium HEPES buffer solution containing 25 mM of potassium chloride, 25 mM of magnesium chloride, 10 mM of DTT and 50 μM of zinc chloride. 1.5 μM of Ras substrate protein, 0.15 μM of tritium-farnesylpyrophosphate and 4.5 nM of farnesyl transferase were used. More specifically, in the initial step, farnesyl transferase was added to the above buffer solution, reaction was maintained for 30 minutes at 37° C. and then the reaction was stopped by adding 1 ml of ethanol solution containing 1M HCl. The formed precipitates were adsorbed to GF/B filter using Hopper harvestor (Hopper #FH 225V) for filter-binding, washed with ethanol, and then radioactivity of the dried filter was measured using LKB β counter. Enzyme titer was measured in the unsaturated state of substrate where the concentration of Ras substrate protein and farnesyl transferase have quantitative relationship. The compound according to the present invention dissolved in dimethyl sulfoxide(DMSO) was added to the reaction solution in an amount of less than 5% of the total reaction solution, and then the enzyme inhibitory activity thereof was measured. The enzyme inhibitory activity was represented by percentage of the amount of farnesyl incorporated into the Ras substrate protein in the presence of the test compound to that in the absence of the test compound. $IC_{50}$ of the test compound was defined as the concentration at which 50% of the enzyme activity was inhibited. To evaluate the selective enzyme inhibitory activity of the compound according to the present invention, inhibitory activity on geranylgeranyl transferase was measured. Geranylgeranyl transferase was purified from bovine brain according to the modified Schaber's method(Schaber et al., J. Biol. Chem. 265, 14701, 1990), and substantially the same experimental procedure as that for farnesyl transferase was performed on geranylgeranyl pyrophosphate and Ras-CVIL substrate protein. The test results are represented in the following Table 2.

EXPERIMENTAL EXAMPLE 2

Analysis of In Vivo Inhibitory Activity for Ras Farnesyl Transferase

In the present experiment, Rat2 cell line which expresses C-Harvey-Ras protein having transforming activity and Rat2 cell line(Korean patent application No. 97-14409) which is transformed with fused protein of H-Ras substituted with polybasic lysine domain at C-terminus of K-Ras were used. The experiment was performed by the modified Declue's method(Declue. J. E. et al., Cancer Research, 51, 712, 1991) as follows.

$3\times10^5$ cells of transformed Rat2 fibroblast cell line were sprayed on 60 mm cell cultivation dish and cultivated for 48 hours in a cell incubator at 37° C. and after 50% or more of density was reached, it was treated with the test compounds. The compound according to the present invention dissolved in dimethylsulfoxide(DMSO) was used. 1% concentration of dimethylsulfoxide was used in both control and test groups. After 4 hours from the treatment with the compound, methionine labeled with 150 $\mu$Ci of radioactive isotope [$^{35}$S] per 1 ml of medium was added and after cultivating for 20 hours, the cells were washed with physiological saline water. The cells were lysed using 1 ml of cold cell lysis buffer solution(50 mM of Sodium HEPES buffer solution containing 5 mM of magnesium chloride, 1 mM of DTT, 1% NP 40, 1 mM of EDTA, 1 mM of PMSF, 2 $\mu$M of leupeptin, 2 $\mu$M of pepstatin A and 2 $\mu$M of antipain) and the supernatant wherein the cells were lysed was obtained by high-velocity centrifugation of 12,000 g×5 minutes. The amount of radioisotope in the supernatant was measured and standardized to obtain a quantitative result in immunoprecipitation reaction and then, Y13-259, a monoclonal antiboby specifically binding to Ras protein(see: Furth, M. E. et al., *J. Virol,* 43, 294, 1982) was added and reacted for 15 hours at 4° C. Protein A(combined with goat anti-murine immunoglobulin antibody)-agarose suspension was added to the solution and reacted for 1 hour at 4° C. and then, to remove the unspecific binding product, immunoprecipitates were washed with a buffer solution (50 mM Tris chloride buffer solution containing 50 mM of sodium chloride, 0.5% of sodium dioxycholate, 0.5% of NP 40 and 0.1% of SDS). The precipitates were added to a buffer solution for electrophoresis and boiled and then, electrophoresis was performed using 13.5% of SDS polyacrylamide gel. After electrophoresis, the gel was fixed and dried. Then, the gel was exposed to X-ray film, developed and printed. From the result of the experiment, intensities of band of protein combined with or without farnesyl of Ras protein was measured, and the concentration of the test compound inhibiting 50% of farnesyl binding was defined as $CIC_{50}$, an in vivo Ras farnesyl transferase inhibitory activity. The test results are shown in the following Table 2. $IC_{50}$ means the data from Experimental 1 and $CIC_{50}$ means the data from Experimental 2.

TABLE 2a

| EX. NO. | H-Ras $IC_{50}(\mu M)$ | H-Ras $CIC_{50}(\mu M)$ | K-Ras $IC_{50}(\mu M)$ | K-Ras $CIC_{50}(\mu M)$ |
|---|---|---|---|---|
| 1 | <0.01 | <0.025 | <0.01 | 10–50 |
| 2 | <0.01 | <0.025 | <0.01 | 10–50 |
| 3 | <0.01 | <0.025 | <0.01 | 10–50 |
| 4 | <0.01 | <0.025 | <0.01 | 10–100 |
| 5 | <0.01 | <0.025 | <0.01 | 10–50 |
| 6 | <0.01 | <0.025 | <0.01 | 10–50 |
| 7 | <0.01 | <0.025 | <0.01 | 10–50 |
| 8 | <0.01 | >0.025 | <0.01 | 10–50 |
| 9 | <0.01 | <0.025 | <0.01 | 10–50 |
| 10 | <0.01 | >0.025 | <0.1 | 10–50 |
| 11 | <0.01 | >0.025 | <0.1 | 10–50 |
| 12 | <0.01 | >0.025 | <0.1 | 10–50 |
| 13 | <0.01 | <0.025 | <0.01 | 10–50 |
| 14 | <0.01 | <0.025 | <0.01 | 10–50 |
| 15 | <0.006 | >0.025 | <0.013 | >10 |
| 16 | <0.0015 | >0.025 | <0.0023 | >10 |
| 17 | <0.0018 | >0.025 | <0.0064 | >>10 |
| 18 | <0.0035 | >0.025 | <0.012 | >10 |
| 19 | <0.00095 | <0.0125 | <0.002 | >10 |
| 20 | <0.0035 | >0.025 | <0.018 | >10 |
| 21 | >0.030 | >0.030 | >0.030 | >10 |
| 22 | <0.0027 | >0.025 | <0.030 | >10 |
| 23 | <0.022 | >0.030 | >0.030 | >10 |

TABLE 2b

| EX. NO. | H-Ras $IC_{50}(\mu M)$ | H-Ras $CIC_{50}(\mu M)$ | K-Ras $IC_{50}(\mu M)$ | K-Ras $CIC_{50}(\mu M)$ |
|---|---|---|---|---|
| 24 | <0.00445 | >0.025 | <0.007 | <10 |
| 25 | <0.002 | <0.01 | <0.006 | <5 |
| 26 | <0.002 | <0.025 | <0.0065 | >10 |
| 27 | <0.003 | <0.025 | >0.02 | >10 |
| 28 | <0.0022 | <0.00625 | <0.0032 | <10 |
| 29 | <0.00245 | <0.00625 | <0.0027 | <10 |
| 30 | <0.005 | <0.0125 | <0.0021 | <10 |
| 31 | <0.0032 | <<0.00625 | <0.0021 | <10 |
| 32 | <0.006 | <0.00625 | <0.015 | >10 |
| 33 | >0.03 | >0.03 | >0.03 | >10 |
| 34 | <0.004 | >0.0125 | <0.0047 | >10 |
| 35 | <0.0025 | <0.0025 | <0.0059 | >10 |
| 36 | <0.0055 | >0.1 | <0.0155 | >20 |
| 37 | <0.0057 | >0.025 | <0.0095 | >10 |
| 38 | <0.023 | >0.025 | >0.03 | >10 |
| 39 | <0.006 | <0.025 | <0.0083 | >10 |
| 40 | <0.024 | >0.05 | >0.030 | >10 |
| 41 | <0.009 | >0.05 | <0.004 | >10 |
| 42 | <0.00415 | >0.05 | <0.0075 | >10 |
| 43 | <0.003 | >0.05 | <0.013 | >10 |
| 44 | <0.011 | <0.025 | <0.015 | >10 |
| 45 | <0.016 | <0.025 | <0.016 | >10 |
| 46 | <0.007 | >0.05 | <0.006 | >10 |

TABLE 2c

| EX. NO. | H-Ras $IC_{50}(\mu M)$ | H-Ras $CIC_{50}(\mu M)$ | K-Ras $IC_{50}(\mu M)$ | K-Ras $CIC_{50}(\mu M)$ |
|---|---|---|---|---|
| 47 | <0.015 | <0.0125 | <0.029 | >10 |
| 48 | >0.03 | >0.05 | >0.03 | >10 |
| 49 | <0.03 | >0.05 | >0.03 | >10 |
| 50 | >0.03 | >0.05 | >0.03 | >10 |
| 51 | <0.010 | <0.010 | <0.030 | >10 |
| 52 | <0.010 | <0.010 | <0.030 | >10 |
| 53 | <0.010 | <0.010 | <0.030 | >10 |
| 54 | <0.010 | <0.010 | <0.030 | >10 |
| 55 | <0.010 | <0.010 | <0.030 | >10 |

What is claimed is:
1. A compound represented by the following formula (1):

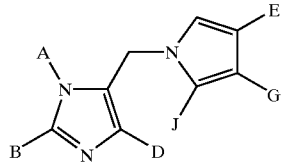

in which
A represents hydrogen, lower alkyl, or a structure selected from the following group:

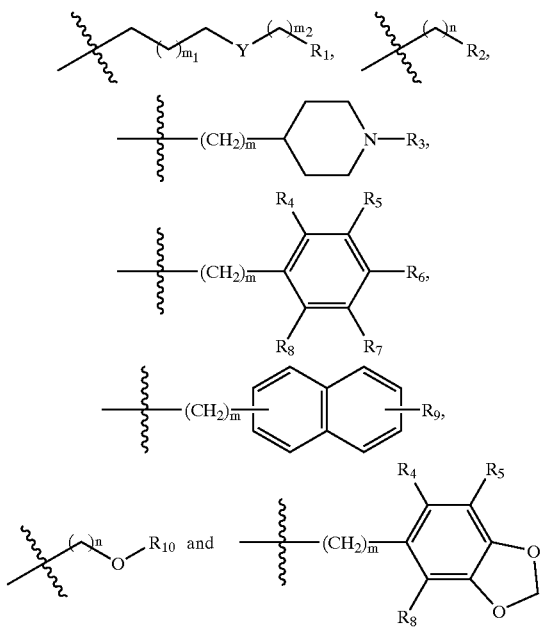

wherein
$m_1$, $m_2$, m and n independently of one another denote an integer of 0 to 5,
Y represents O, S, S=O or $SO_2$,
$R_1$ represents hydrogen, or represents optionally saturated 3- to 6-membered heterocycle or bicyclo 9- to 10-membered aromatic heterocycle, each of which has one or more hetero atoms selected from a group consisting of nitrogen, sulfur and oxygen, or represents a structure selected from the following group:

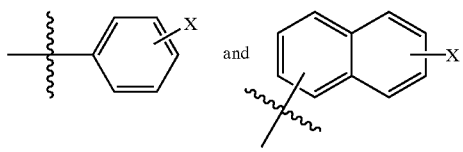

wherein, X represents hydrogen, halogen, lower alkyl, lower alkoxy, nitro, cyano, hydroxy or phenoxy,
$R_2$ represents optionally saturated 3- or 9-membered heterocycle or bicyclo 9- or 10-membered aromatic heterocycle, each of which has one or more hetero atoms selected from a group consisting of nitrogen, sulfur and oxygen, or represents a structure selected from the following group:

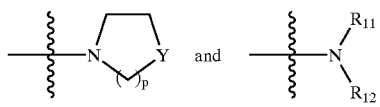

wherein p denotes an integer of 1 to 3, Y is defined as previously described, $R_{11}$ and $R_{12}$ independently of one another represent lower alkyl optionally substituted by phenyl or naphthyl, or represent $C_3$–$C_7$-cycloalkyl, phenyl or naphthyl,
$R_3$ represents lower alkyl, lower alkylcarbonyl, lower alkoxycarbonyl or lower alkylsulfonyl, each of which is optionally substituted by phenyl or naphthyl, or represents sulfonyl substituted by phenyl or naphthyl,
$R_4$ and $R_8$ independently of one another represent hydrogen, lower alkyl, lower alkoxy or halogen,
$R_5$ and $R_7$ independently of one another represent hydrogen, lower alkyl, lower alkoxy, halogen or hydroxy,
$R_6$ represents hydrogen, lower alkyl, lower alkoxy, hydroxy, di(lower alkyl)amine, $C_3$–$C_6$-cycloalkyl, $C_3$–$C_6$-cycloalkyl-lower alkyl, halogen, phenyl or phenoxy,
$R_9$ represents hydrogen or lower alkyl,
$R_{10}$ represents aralkyl optionally substituted by lower alkyl or halogen,
B represents hydrogen, lower alkyl, lower alkylthio or amino,
D represents hydrogen, lower alkyl, halogen, lower alkylthio, nitro or amino,
E represents phenyl, or naphthyl optionally substituted by halogen,
G represents nitro or amino, or represents a structure of

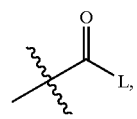

wherein L represents a structure selected from the following group:

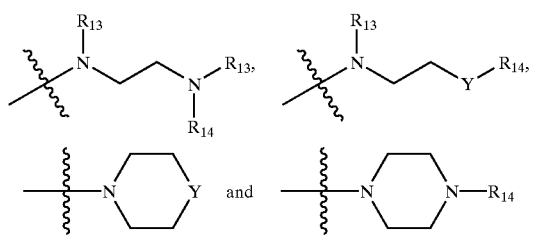

wherein
$R_{13}$ and $R_{14}$ independently of one another represent hydrogen, hydroxy, lower alkyl or lower alkoxy,
Y is defined as previously described,
J represents hydrogen, lower alkyl, lower alkylthio or phenyl,
provided that A does not represent hydrogen, lower alkyl or any one structure selected from the following group:

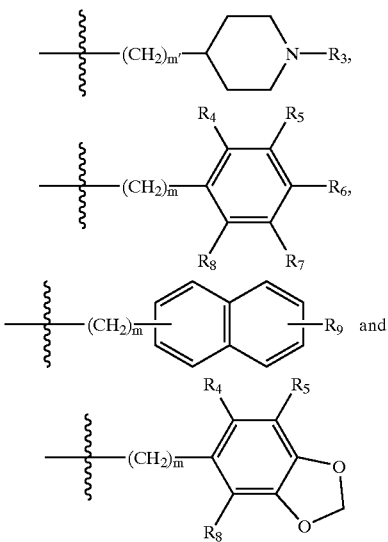

wherein m and $R_3$ to $R_9$ are defined as previously described, m' denotes an integer of 1 to 5, when B, J and D represent hydrogen at the same time and G does not represent nitro or amino, or pharmaceutically acceptable salts or isomers thereof.

2. The compound of claim 1 wherein

A represents lower alkyl or a structure selected from the having one or more hetero atoms selected from a group consisting of nitrogen, sulfur and oxygen, or represents a structure of

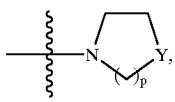

wherein p denotes an integer of 1 or 2 and Y represents O, $R_3$ represents lower alkyl optionally substituted by phenyl or naphthyl, $R_4$ and $R_8$ independently of one another represent hydrogen or lower alkoxy, $R_5$ and $R_7$ independently of one another represent hydrogen, lower alkoxy or halogen, $R_6$ represents hydrogen, lower alkyl, lower alkoxy or halogen, $R_9$ represents hydrogen, $R_{10}$ represents aralkyl optionally substituted by lower alkyl or halogen, B represents hydrogen, lower alkyl, lower alkylthio or amino, D represents hydrogen, lower alkyl, halogen, nitro or amino, E represents naphthyl optionally substituted by halogen, G represents nitro or amino, or represents a structure of

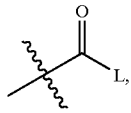

wherein L represents a structure selected from the following group:

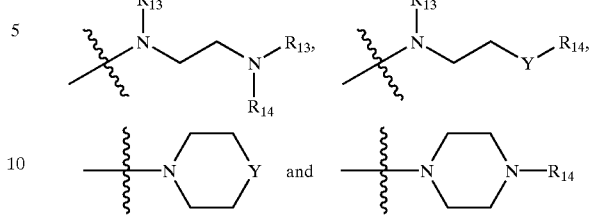

wherein $R_{13}$ and $R_{14}$ independently of one another represent lower alkyl or lower alkoxy, Y represents O or S, J represents hydrogen, lower alkyl or lower alkylthio.

3. The compound of claim 1 which is selected from a group consisting of:

1-[1-(3-benzyloxypropyl)-1H-imidazol-5-yl]methyl-3-[N-(2-methoxy ethyl)-N-methyl]carbamoyl-4-(naphthalen-1-yl)-1H-pyrrole(1);

1-[1-(3-benzyloxypropyl)-1H-imidazol-5-yl]methyl-3-(morpholin-4-yl) carbonyl-4-(naphthalen-1-yl)-1H-pyrrole(2);

1-[1-(3-benzyloxypropyl)-1H-imidazol-5-yl]methyl-3-(4-methylpiperazin-1-yl)carbonyl-4-(naphthalen-1-yl)-1H-pyrrole(3);

3-[N-(2-methoxyethyl)-N-methyl]carbamoyl-4-(naphthalen-1-yl)-1-[1-(3-phenoxypropyl)-1H-imidazol-5-yl]methyl-1H-pyrrole(4);

3-[N-(2-methoxyethyl)-N-methyl]carbamoyl-4-(naphthalen-1-yl)-1-[1-(3-thiophenoxypropyl)-1H-imidazol-5-yl]methyl-1H-pyrrole(5);

3-(morpholin-4-yl)carbonyl-4-(naphthalen-1-yl)-1-[1-(3-phenoxypropyl)-1H-imidazol-5-yl]methyl-1H-pyrrole(6);

3-(4-methylpiperazin-1-yl)carbonyl-4-(naphthalen-1-yl)-1-[1-(3-phenoxypropyl)-1H-imidazol-5-yl]methyl-1H-pyrrole(7);

3-[N-(2-methoxyethyl)-N-methyl]carbamoyl-4-(naphthalen-1-yl)-1-[1-(3-thioethoxypropyl)-1H-imidazol-5-yl]methyl-1H-pyrrole(8);

3-[N-(2-methoxyethyl)-N-methyl]carbamoyl-1-{1-[3-(morpholin-4-yl) propyl]-1H-imidazol-5-yl}methyl-4-(naphthalen-1-yl)-1H-pyrrole(9);

3-[N-(2-methoxyethyl)-N-methyl]carbamoyl-4-(naphthalen-1-yl)-1-{1-[2-(thiophen-2-yl)ethyl]-1H-imidazol-5-yl}methyl-1H-pyrrole(10);

3-(4-methylpiperazin-1-yl)carbonyl-4-(naphthalen-1-yl)-1-{1-[2-(thiophen-2-yl)ethyl]-1H-imidazol-5-yl}methyl-1H-pyrrole(11);

1-[1-(furan-2-yl)methyl-1H-imidazol-5-yl]methyl-3-(4-methylpiperazin-1-yl)carbonyl-4-(naphthalen-1-yl)-1H-pyrrole(12);

1-[1-(1-benzylpiperidin-4-yl)-1H-imidazol-5-yl]methyl-3-[N-(2-methoxyethyl)-N-methyl]carbamoyl-4-(naphthalen-1-yl)-1H-pyrrole(13);

1-[1-(1-benzylpiperidin-4-yl)-1H-imidazol-5-yl]methyl-3-(morpholin-4-yl)carbonyl-4-(naphthalen-1-yl)-1H-pyrrole(14);

1-[2-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(15);

1-[4-methyl-1-(3,4-methylenedioxybenzyl)-1H-imidazol-5-ylmethyl]-3-(4-methylpiperazin-1-yl)carbonyl-4-(naphthalen-1-yl)-1H-pyrrole(16);

1-[2-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(17);

1-[1-(3,4-methylenedioxybenzyl)-2-methylthio-1H-imidazol-5-ylmethyl]-3-(4-methylpiperazin-1-yl)carbonyl-4-(naphthalen-1-yl)-1H-pyrrole(18);

1-[1-(3,4-methylenedioxybenzyl)-1H-imidazol-5-ylmethyl]-3-(4-methyl piperazin-1-yl)carbonyl-2-methylthio-4-(naphthalen-1-yl)-1H-pyrrole(19);

1-[4-iodo-1-(3,4-methylenedioxybenzyl)-1H-imidazol-5-ylmethyl]-3-(4-methylpiperazin-1-yl)carbonyl-4-(naphthalen-1-yl)-1H-pyrrole(20);

1-[1-(3,4-methylenedioxybenzyl)-4-nitro-1H-imidazol-5-ylmethyl]-3-(4-methylpiperazin-1-yl)carbonyl-4-(naphthalen-1-yl)-1H-pyrrole(21);

1-[4-amino-1-(3,4-methylenedioxybenzyl)-1H-imidazol-5-ylmethyl]-3-(4-methylpiperazin-1-yl)carbonyl-4-(naphthalen-1-yl)-1H-pyrrole(22);

3-(4-methoxypiperazin-1-yl)carbonyl-1-[4-methyl-1-(3,4-methylenedioxybenzyl)-1H-imidazol-5-ylmethyl]-4-(naphthalen-1-yl)-1H-pyrrole(23);

2-methyl-1-[1-(3,4-methylenedioxybenzyl)-1H-imidazol-5-ylmethyl]-3-(4-methylpiperazin-1-yl)carbonyl-4-(naphthalen-1-yl)-1H-pyrrole(24);

2-ethylthio-1-[1-(3,4-methylenedioxybenzyl)-1H-imidazol-5-ylmethyl]-3-(4-methylpiperazin-1-yl)carbonyl-4-(naphthalen-1-yl)-1H-pyrrole(25);

1-[1-(2-methoxyphenethyl)-2-methyl-1H-imidazol-5-ylmethyl]-3-(4-methylpiperazin-1-yl)carbonyl-4-(naphthalen-1-yl)-1H-pyrrole(26);

1-[1-(3-ethoxypropyl)-2-methyl-1H-imidazol-5-ylmethyl]-3-(4-methyl piperazin-1-yl)carbonyl-4-(naphthalen-1-yl)-1H-pyrrole(27);

1-[1-(3-ethoxypropyl)-4-methyl-1H-imidazol-5-ylmethyl]-3-(4-methyl piperazin-1-yl)carbonyl-4-(naphthalen-1-yl)-1H-pyrrole(28);

1-[1-(3-benzyloxypropyl)-4-methyl-1H-imidazol-5-ylmethyl]-3-(4-methylpiperazin-1-yl)carbonyl-4-(naphthalen-1-yl)-1H-pyrrole(29);

1-[1-(3-benzyloxypropyl)-4-methyl-1H-imidazol-5-ylmethyl]-3-[N-(2-methoxyethyl)-N-methyl]carbamoyl-4-(naphthalen-1-yl)-1H-pyrrole(30);

1-{1-[3-(2-chlorobenzyloxy)propyl]-4-methyl-1H-imidazol-5-ylmethyl}-3-(4-methylpiperazin-1-yl)carbonyl-4-(naphthalen-1-yl)-1H-pyrrole(31);

1-{1-[3-(2-chlorobenzyloxy)propyl]-4-methyl-1H-imidazol-5-ylmethyl}-3-[N-(2-methoxyethyl)-N-methyl]carbamoyl-4-(naphthalen-1-yl)-1H-pyrrole(32);

1-[1-(3-benzyloxypropyl)-2-methyl-1H-imidazol-5-ylmethyl]-3-(4-methylpiperazin-1-yl)carbonyl-4-(naphthalen-1-yl)-1H-pyrrole(33);

1-[1-(3-benzyloxypropyl)-2-methyl-1H-imidazol-5-ylmethyl]-3-[N-(2-methoxyethyl)-N-methyl]carbamoyl-4-(naphthalen-1-yl)-1H-pyrrole(34);

1-[(phenethyl)-2-methyl-1H-imidazol-5-ylmethyl]-3-(4-methylpiperazin-1-yl)carbonyl-4-(naphthalen-1-yl)-1H-pyrrole(35);

1-[1-(3,4-methylenedioxybenzyl)-1H-imidazol-5-ylmethyl]-4-(naphthalen-1-yl)-3-nitro-1H-pyrrole(36);

1-[1-(4-chlorobenzyl)-1H-imidazol-5-ylmethyl]-4-(naphthalen-1-yl)-3-nitro-1H-pyrrole(37);

1-[1-(4-bromobenzyl)-1H-imidazol-5-ylmethyl]-4-(naphthalen-1-yl)-3-nitro-1H-pyrrole(38);

1-[1-(phenethyl)-1H-imidazol-5-ylmethyl]-4-(naphthalen-1-yl)-3-nitro-1H-pyrrole(39);

1-[1-(4-methylphenethyl)-1H-imidazol-5-ylmethyl]-4-(naphthalen-1-yl)-3-nitro-1H-pyrrole(40);

1-[1-(4-chlorophenethyl)-1H-imidazol-5-ylmethyl]-4-(naphthalen-1-yl)-3-nitro-1H-pyrrole(41);

1-[1-(4-fluorophenethyl)-1H-imidazol-5-ylmethyl]-4-(naphthalen-1-yl)-3-nitro-1H-pyrrole(42);

1-[1-(3-bromophenethyl)-1H-imidazol-5-ylmethyl]-4-(naphthalen-1-yl)-3-nitro-1H-pyrrole(43);

1-[1-(4-methoxyphenethyl)-1H-imidazol-5-ylmethyl]-4-(naphthalen-1-yl)-3-nitro-1H-pyrrole(44);

1-[1-(3-methoxyphenethyl)-1H-imidazol-5-ylmethyl]-4-(naphthalen-1-yl)-3-nitro-1H-pyrrole(45);

1-[1-(naphthalen-1-ylethyl)-1H-imidazol-5-ylmethyl]-4-(naphthalen-1-yl)-3-nitro-1H-pyrrole(46);

1-[1-(3-ethoxypropyl)-1H-imidazol-5-ylmethyl]-4-(naphthalen-1-yl)-3-nitro-1H-pyrrole(47);

1-[1-(methyl)-1H-imidazol-5-ylmethyl]-4-(naphthalen-1-yl)-3-nitro-1H-pyrrole(48);

1-[1-(naphthalen-2-ylmethyl)-1H-imidazol-5-ylmethyl]-4-(naphthalen-1-yl)-3-nitro-1H-pyrrole(49);

3-amino-1-[1-(4-chlorobenzyl)-1H-imidazol-5-ylmethyl]-4-(naphthalen-1-yl)-1H-pyrrole(50);

4-(3-bromonaphthalen-1-yl)-1-[4-methyl-1-(3,4-methylenedioxybenzyl)-1H-imidazol-5-ylmethyl]-3-(4-methylpiperazin-1-yl)carbonyl-1H-pyrrole(51);

4-(3-chloronaphthalen-1-yl)-1-[4-methyl-1-(3,4-methylenedioxybenzyl)-1H-imidazol-5-ylmethyl]-3-(4-methylpiperazin-1-yl)carbonyl-1H-pyrrole(52);

4-(3-bromonaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(53);

4-(3-chloronaphthalen-1-yl)-1-[4-methyl-1-(naphthalen-2-yl)methyl-1H-imidazol-5-ylmethyl]-3-(4-methylpiperazin-1-yl)carbonyl-1H-pyrrole(54); and 1-[4-methyl-1-(naphthalen-2-yl)methyl-1H-imidazol-5-ylmethyl]-3-(4-methylpiperazin-1-yl)carbonyl-4-(naphthalen-1-yl)-1H-pyrrole(55).

4. A pharmaceutical composition for treating cancer comprising a pharmaceutically acceptable carrier and as an active ingredient the compound of formula (1), pharmaceutically acceptable salt or stereoisomers thereof as defined in claim 1.

5. A pharmaceutical composition for treating restenosis comprising a pharmaceutically acceptable carrier and as an active ingredient the compound of formula (1), pharmaceutically acceptable salt or stereoisomers thereof as defined in claim 1.

6. A pharmaceutical composition for treating atherosclerosis comprising a pharmaceutically acceptable carrier and as an active ingredient the compound of formula (1), pharmaceutically acceptable salt or stereoisomers thereof as defined in claim 1.

7. A pharmaceutical composition for treating viral infections comprising a pharmaceutically acceptable carrier and as an active ingredient the compound of formula (1), pharmaceutically acceptable salt or stereoisomers thereof as defined in claim 1.

* * * * *